(12) United States Patent
Jensen et al.

(10) Patent No.: US 11,787,837 B2
(45) Date of Patent: Oct. 17, 2023

(54) DCHBS-ACTIVE ESTERS OF PEG COMPOUNDS AND THEIR USE

(71) Applicant: Novo Nordisk A/S, Bagsvaerd (DK)

(72) Inventors: Kim Birkebaek Jensen, Roedovre (DK); Magnus Bernt Fredrik Gustafsson, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 960 days.

(21) Appl. No.: 16/346,560

(22) PCT Filed: Nov. 7, 2017

(86) PCT No.: PCT/EP2017/078457
§ 371 (c)(1),
(2) Date: May 1, 2019

(87) PCT Pub. No.: WO2018/083335
PCT Pub. Date: May 11, 2018

(65) Prior Publication Data
US 2019/0263854 A1 Aug. 29, 2019

(30) Foreign Application Priority Data

Nov. 7, 2016 (EP) .................................... 16197464
Jul. 17, 2017 (EP) .................................... 17181621

(51) Int. Cl.
| | | |
|---|---|---|
| *A61K 47/60* | (2017.01) | |
| *C07C 309/42* | (2006.01) | |
| *C07C 311/29* | (2006.01) | |
| *C07C 317/22* | (2006.01) | |
| *C08L 71/02* | (2006.01) | |
| *C07K 1/02* | (2006.01) | |
| *C07K 1/113* | (2006.01) | |
| *C07K 1/107* | (2006.01) | |
| *C07K 14/605* | (2006.01) | |
| *C07K 14/62* | (2006.01) | |
| *C08L 71/00* | (2006.01) | |
| *A61K 47/54* | (2017.01) | |

(52) U.S. Cl.
CPC .......... *C07K 1/1077* (2013.01); *A61K 47/542* (2017.08); *A61K 47/60* (2017.08); *C07C 309/42* (2013.01); *C07C 311/29* (2013.01); *C07C 317/22* (2013.01); *C07K 1/023* (2013.01); *C07K 14/605* (2013.01); *C07K 14/62* (2013.01); *C08L 71/00* (2013.01); *C08L 71/02* (2013.01); *C07C 2601/14* (2017.05); *C08L 2203/02* (2013.01)

(58) Field of Classification Search
CPC ...... A61K 38/26; A61K 47/60; C07C 309/42; C07C 311/29; C07C 317/22; C07K 1/026; C07K 1/1077; C08L 71/02
See application file for complete search history.

(56) References Cited

U.S. PATENT DOCUMENTS

| | | | |
|---|---|---|---|
| 6,451,974 B1 | 9/2002 | Hansen | |
| 6,458,924 B2 * | 10/2002 | Knudsen | ................ A61K 38/28 |
| | | | 530/324 |
| 10,005,827 B2 | 6/2018 | Spetzler et al. | |
| 2004/0115759 A1 | 6/2004 | Dunweber et al. | |
| 2010/0317057 A1 | 12/2010 | Lau et al. | |
| 2011/0098439 A1 | 4/2011 | Madsen et al. | |
| 2011/0213131 A1 | 9/2011 | Christensen et al. | |
| 2014/0088005 A1 | 3/2014 | Wieczorek et al. | |
| 2015/0152157 A1 | 6/2015 | Kofoed et al. | |

FOREIGN PATENT DOCUMENTS

| | | |
|---|---|---|
| JP | 2010535849 A | 11/2010 |
| JP | 2011509077 A | 3/2011 |
| JP | 2014511870 A | 5/2014 |
| WO | 96/15803 A1 | 5/1996 |
| WO | 00/55119 | 9/2000 |

(Continued)

OTHER PUBLICATIONS

Cabaret et al., "A low-epimerizing peptide coupling reagent based on the rearrangement of a carboxylic-sulfonic mixed anhydride", Tetrahedron Letters, Dec. 19, 1994, vol. 25, Issue 51, pp. 9561-9564.

Bereznak et al., "Preparation of 2, 4-Bis(Methylsulfonyl)-1-naphthyl (BMSN) Active Esters and Their Potential Utility in Peptide Bond Formation," Synthetic Communications, Dec. 1989, vol. 19, No. 20, pp. 3573-3578.

Cabaret et al., A Low Epimerizing Peptide Coupling Reagent Based on the Rearrangement of a Carboxylic Sulfonic Mixed Anhydride, Tetrahedron Letters, 1994, vol. 35, No. 51, pp. 9561-9564.

(Continued)

*Primary Examiner* — Jeffrey E. Russel
(74) *Attorney, Agent, or Firm* — Rosemarie R. Wilk-Orescan

(57) ABSTRACT

The present invention relates to a novel acylating agent, a method for its preparation, and a method of using it for acylating one or more amino groups of an amino acid, a peptide, or a protein. The novel acylating agent may be a compound which comprises a structural element —HN—(CH2)2-(O—((CH2)2)k-O—(CH2)n-CO—, wherein k is an integer in the range of 1-10, and n is an integer in the range of 1-2, being esterified at its —CO-end to the hydroxy group of 3,5-dichloro-2-hydroxy-benzenesulfonic acid (3,5-DC-2-HBSA). This novel acylating agent has an improved stability. Using this agent the acylation process is improved as regards robustness, as well as improving yield and overall production economy. The novel acylating agent is useful for acylating pharmaceutical peptides and proteins such as GLP-1, insulin, pYY, and amylin. The invention also relates to a number of novel GLP-1 precursor peptides and derivatives in which the two N-terminal amino acids have been deleted.

16 Claims, No Drawings
Specification includes a Sequence Listing.

(56) References Cited

FOREIGN PATENT DOCUMENTS

| WO | 2006097537 A2 | 9/2006 | | |
|---|---|---|---|---|
| WO | 2007079755 A1 | 7/2007 | | |
| WO | 2009/115469 A1 | 9/2009 | | |
| WO | 2010/029159 A1 | 3/2010 | | |
| WO | 2011/080103 A1 | 7/2011 | | |
| WO | 2012140117 A1 | 10/2012 | | |
| WO | 2015000942 A1 | 1/2015 | | |
| WO | 2015/022400 A1 | 2/2015 | | |
| WO | WO-2015091613 A1 * | 6/2015 | ............... | C07K 1/12 |
| WO | 2016083499 A1 | 6/2016 | | |
| WO | 2016097108 A1 | 6/2016 | | |

OTHER PUBLICATIONS

Massah et al., "ZSM-5-SO3H: An Efficient Catalyst for Acylation of Sulfonamides Amines, Alcohols, and Phenols under Solvent-Free Conditions", ISRN Organic Chemistry, Dec. 2013, vol. 2013, Article ID 951749, pp. 1-12.

\* cited by examiner

DCHBS-ACTIVE ESTERS OF PEG COMPOUNDS AND THEIR USE

The present invention relates to novel acylating agents, their preparation, and their use in preparing acylated amino acids, peptides, and proteins.

CROSS-REFERENCE TO RELATED APPLICATIONS

This application is a 35 U.S.C. § 371 National Stage application of International Application PCT/EP2017/078457 (WO 2018/083335), filed Nov. 7, 2017, which claims priority to European Patent Applications 16197464.7, filed Nov. 7, 2016 and 17181621.8, filed Jul. 17, 2017.

In accordance with 37 C.F.R. § 1.52(e)(5), Applicants enclose herewith the Sequence Listing for the above-captioned application entitled "160032US01_SeqList.txt", updated with US application information on Apr. 4, 2019, and updated on Oct. 20, 2022, both of which are incorporated by reference herein. The Sequence Listing is made up of 15 kilobytes, and the information contained in the attached "SEQUENCE LISTING" is identical to the information in the specification as originally filed. No new matter is added.

BACKGROUND

The attachment of one or more substituents to peptides or proteins by acylation of one or more amino groups of the peptide or protein is well-known in the art. For a pharmaceutical peptide or protein this may be an efficient way of achieving a prolonged duration of action in vivo of the pharmaceutical peptide or protein.

Non-limiting examples of pharmaceutical peptides or proteins which have been acylated include, e.g., GLP-1 peptides and insulin peptides.

Various examples of mono-acylated, di-acylated, and tri-acylated GLP-1 peptides are disclosed in, e.g., WO 2006/097537, WO 2011/080103, WO 2012/140117, WO 2015/000942, WO 2015/022400, WO 2016/083499, and WO 2016/097108.

Various examples of acylated insulin peptides are disclosed in, e.g., WO 2009/115469).

Methods for acylating peptides and proteins are disclosed in, e.g., WO 00/55119 and WO 2010/029159.

Tetrahedron Letters, vol. 35, no. 51 pp. 9561-9564 (1994) describes the use of an o-hydroxybenzenesulfonyl chloride as a condensation reagent.

SUMMARY

The present invention relates to a novel acylating agent in the form of an ester of a compound that comprises an element of Chem. 6b:

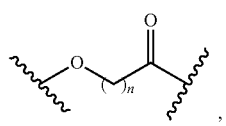

Chem. 6b wherein n is an integer in the range of 1-2, with an activator of Chem. 1c:

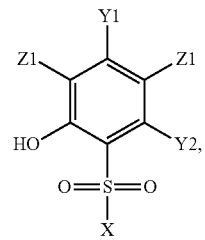

Chem. 1c wherein

—Z1 and —Z2 independently are selected from the group consisting of —Cl, —F, —Br, —NO$_2$, —CN, —SO$_2$X2, —CONH, and —CF$_3$, wherein X2 is selected from the group consisting of —OH, CH$_3$, —CF$_3$, and —N(R$^1$R$^2$) (e.g. —N(CH$_3$)$_2$), —Y1 and —Y2 independently are absent or selected from the group consisting of —Cl and —F, —X is selected from the group consisting of —OH, CH$_3$, —CF$_3$, and —N(R$^1$R$^2$) (e.g. —N(CH$_3$)$_2$), wherein R$^1$ and R$^2$ independently are selected from the group consisting of H and C1-C5 alkyl, wherein C1-C5 alkyl may be linear, branched or cyclic and optionally substituted with a hydrophilic moiety (such as —OH or —COOH).

Thus, the present invention relates to a novel acylating agent in the form a compound which comprises Chem. 7b:

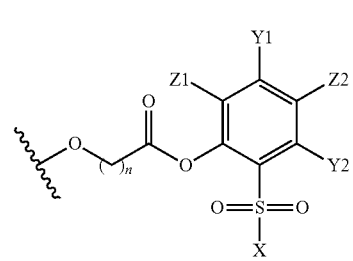

Chem. 7b wherein n is an integer in the range of 1-2,

—Z1 and —Z2 independently are selected from the group consisting of —Cl, —F, —Br, —NO$_2$, —CN, —SO$_2$X2, —CONH, and —CF$_3$, wherein X2 is selected from the group consisting of —OH, CH$_3$, —CF$_3$, and —N(R$^1$R$^2$) (e.g. —N(CH$_3$)$_2$), —Y1 and —Y2 independently are absent or selected from the group consisting of —Cl and —F, —X is selected from the group consisting of —OH, CH$_3$, —CF$_3$, and —N(R$^1$R$^2$) (e.g. —N(CH$_3$)$_2$), wherein R$^1$ and R$^2$ independently are selected from the group consisting of H and C1-C5 alkyl, wherein C1-C5 alkyl may be linear, branched or cyclic and optionally substituted with a hydrophilic moiety (such as —OH or —COOH);

or a salt thereof.

In some embodiments the present invention relates to a novel acylating agent in the form of an ester of a compound that comprises an element of Chem. 6a:

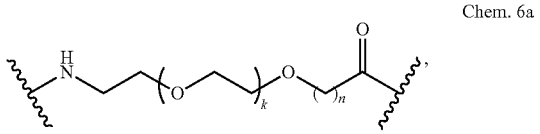

Chem. 6a wherein k is an integer in the range of 1-10, and n is an integer in the range of 1-2, with an activator of Chem. 1b:

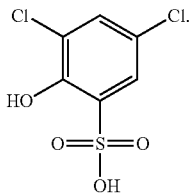

Chem. 1b

Thus, in some embodiments the novel acylating agent of the invention is a compound which comprises Chem. 7:

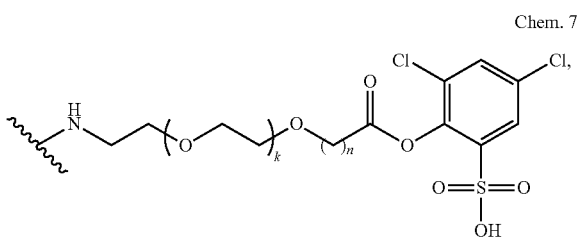

Chem. 7 wherein k is an integer in the range of 1-10, and n is an integer in the range of 1-2; or a salt thereof. This compound may typically be called an activated ester or an activated phenolic ester.

The element of Chem. 6a is often used as a linker or spacer element in substituents acylated to one or more amino groups of pharmaceutical peptides or proteins. These substituents, or side chains, may typically comprise a distal lipophilic moiety often called a protracting moiety and a linker that may typically comprise one or more linker elements including the Chem. 6a linker element. The protracting moiety and the one or more linker elements of the side chain may typically be interconnected via amide bonds. The Chem. 6a element links the entire side chain to the peptide or protein in question, under the formation of an amide bond between the —CO group of Chem. 6a and an amino group of the peptide or protein, resulting in an acylated (N-acylated) peptide or protein. Accordingly, the Chem. 6a linker element is the first linker element of the side chain, it may be said to sit first, right next to, or adjacent to the amino group of the peptide or protein in question. The amino group of the peptide or protein to which the side chain is attached may typically, but not exclusively, be the epsilon-amino groups of a Lys residue of the peptide or protein. See the WO publications referred to above for various non-limiting examples of such acylated pharmaceutical peptides and proteins. This use of Chem. 6a also applies to Chem. 6b and/or Chem. 6c.

The activator of Chem. 1b may briefly be referred to as 3,5-DC-2-HBSA, which stands for 3,5-dichloro-2-hydroxy-benzenesulfonic acid.

The present invention also relates to a method of preparing the acylating agent of the invention by reacting a compound comprising Chem. 6a as defined above with a compound of Chem. 1a:

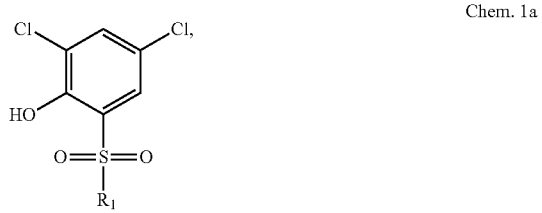

Chem. 1a wherein $R_1$ is OH or a leaving group.

The present invention also relates to a method for acylating an amino group in an amino acid, a peptide, or a protein, the method comprising a step of reacting the amino acid, peptide, or protein with the acylating agent of the invention.

Finally, the present invention also relates to a number of novel GLP-1 peptides and peptide derivatives in which the two N-terminal amino acids of the GLP-1 peptide have been deleted and the preparation of which using the acylation method of the present invention is disclosed herein. These compounds may be referred to as precursors of corresponding peptides and peptide derivatives in which the two N-terminal amino acids are included, which are known from the WO publications referred to above.

Methods for acylating a peptide or protein with a substituent that comprises the Chem. 6a element as a first linker element is described in great detail in, e.g., WO 2010/029159 referred to above, see e.g. p. 12-14 where various activators are listed. The experimental part of WO 2010/029159 reports the preparation of various acylating agents, typically in the form of N-hydroxysuccinimide esters, and the use thereof to prepare a variety of pharmaceutical peptides and proteins. The activator used in activated N-hydroxysuccinimide esters is NHS (N-Hydroxy Succinimide) of Chem. 2:

Chem. 2

In one aspect, the invention provides an alternative activator, the Chem. 1b activator, 3,5-DC-2-HBSA, for use in acylation of an amino group of an amino acid, a peptide, or a protein. In another aspect, the invention provides an alternative activator, 3,5-DC-2-HDMBSA, for use in acylation of an amino group of an amino acid, a peptide, or a protein.

Also or alternatively, in a second aspect, the invention provides an improved acylation process whereby problems in relation to the known acylation process are reduced.

Also or alternatively, in a third aspect, the invention provides an acylating agent of an improved stability.

Also or alternatively, in a fourth aspect, the invention provides a more robust acylation process.

Also or alternatively, in a fifth aspect, the invention provides a more economical acylation process, where the amount used of the acylating agent is reduced, and/or the yield of the desired acylated amino acid, peptide, or protein is improved.

DESCRIPTION

In what follows, Greek letters may be represented by their symbol or the corresponding written name, for example: α=alpha; β=beta; ε=epsilon; γ=gamma; δ=delta; ω=omega; etc. Also, the Greek letter of μ may be represented by "u", e.g. in μl=ul, or in μM=uM.

An asterisk (*) or a waved line in a chemical formula designates i) a point of attachment, ii) a radical, and/or iii) an unshared electron.

The present invention relates to novel acylating agents, methods of their preparation, the use thereof in preparing acylated peptides and proteins, and to novel precursor GLP-1 peptides and derivatives.

Acylating Agent

The present invention relates to a compound which comprises Chem. 7b:

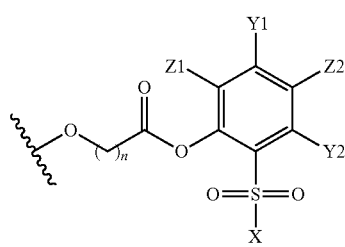

Chem. 7b wherein
n is an integer in the range of 1-2,
—Z1 and —Z2 independently are selected from the group consisting of —Cl, —F, —Br, —NO₂, —CN, —SO₂X2, —CONH, and —CF₃, wherein X2 is selected from the group consisting of —OH, CH₃, —CF₃, and —N(R¹R²) (e.g. —N(CH₃)₂),
—Y1 and —Y2 independently are absent or selected from the group consisting of —Cl and —F,
—X is selected from the group consisting of —OH, CH₃, —CF₃, and —N(R¹R²) (e.g. —N(CH₃)₂),
wherein R¹ and R² independently are selected from the group consisting of H and C1-C5 alkyl, wherein C1-C5 alkyl may be linear, branched or cyclic and optionally substituted with a hydrophilic moiety (such as —OH or —COOH);
or a salt thereof.

In some embodiments the present invention relates to a compound which comprises Chem. 7a:

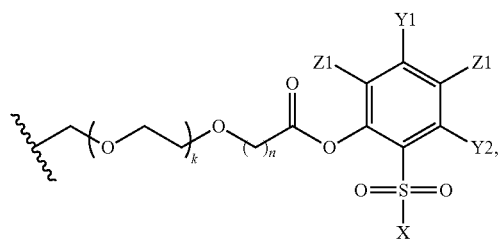

Chem. 7a wherein k is an integer in the range of 1-10, and the remaining substituents are as defined herein.

In some embodiments —Z1 and/or —Z2 are —Cl. In some embodiments —Z1 and —Z2 are —Cl. In some embodiments —Z2 is not —NO₂ or —SO₂X2. In some embodiments —X and/X2 are —OH or —N(CH₃)₂. In some embodiments Y1 and/or Y2 are absent. In some embodiments Y1 and Y2 are absent.

The compound of Chem. 7b or Chem. 7a may also be referred to as an acylating agent or an activated side chain, and it is a phenolic ester of a compound that comprises an element of Chem. 6b or Chem. 6a as defined herein, respectively, with an activator of Chem. 1c as defined herein. The Chem. 6b or Chem. 6a element may be referred to as a linker or spacer element. In some embodiments, the salt of Chem. 7b or Chem. 7a is an alkali metal salt or a tertiary amine salt.

In some embodiments the present invention relates to a compound which comprises Chem. 7:

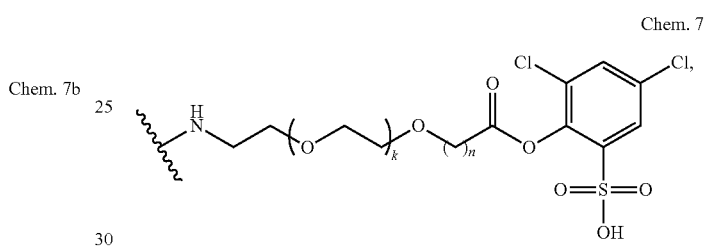

Chem. 7 wherein k is an integer in the range of 1-10, and n is an integer in the range of 1-2; or a salt thereof.

This compound may also be referred to as an acylating agent or an activated side chain, and it is a phenolic ester of a compound that comprises an element of Chem. 6a:

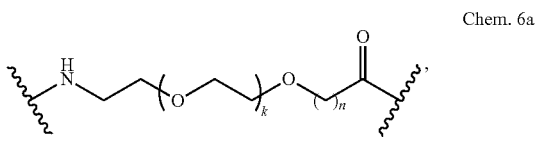

Chem. 6a wherein k is an integer in the range of 1-10, and n is an integer in the range of 1-2, with an activator of Chem. 1b:

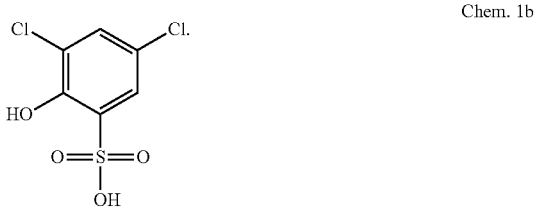 [SMILES: O=S(=O)(O)c1cc(Cl)cc(Cl)c1O]

Chem. 1b

The Chem. 6a element may be referred to as a linker or spacer element.

In some embodiments, when k is 1 and n is 1, Chem. 6a represents 8-amino-3,6-dioxaoctanoic acid, abbreviated Ado.

In some embodiments, the salt of Chem. 7 is a sulfonic acid salt, such as an alkali metal salt or a tertiary amine salt.

In some embodiments, the acylating agent of the invention is a compound which comprises Formula I:

(P-L)$_U$-BL-B-A,  Formula I:

wherein
A is an activator of Chem. 1:

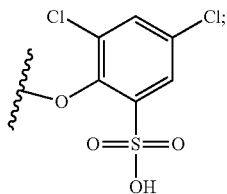 [SMILES: *Oc1c(Cl)cc(Cl)cc1S(=O)(=O)O]

B is a linker element of Chem. 6:

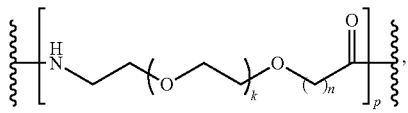

wherein k is an integer in the range of 1-10, n is an integer in the range of 1-2, and p is an integer in the range of 1-5 with the proviso that if k>1 then p is 1;
U represents the number of groups (P-L) in the compound and is 1 or 2;
each group (P-L) comprises
  a protracting moiety (P) independently selected from Chem. 10, Chem. 11, Chem. 12, Chem. 13, and Chem. 14:

Chem. 10

Chem. 11

Chem. 12

Chem. 13

Chem. 14

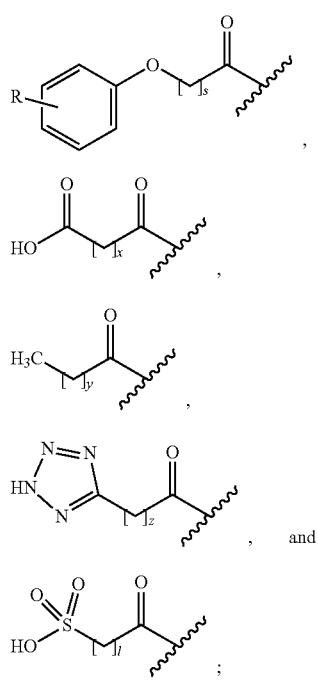

a linker (L) comprising at least one linker element selected from Chem. 15, Chem. 16, Chem. 17, and Chem. 18:

Chem. 15

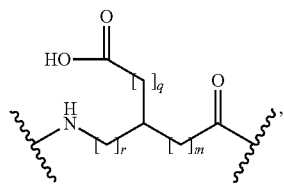

Chem. 16

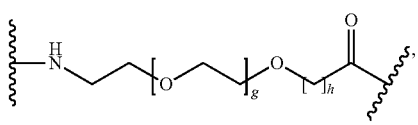

Chem. 17

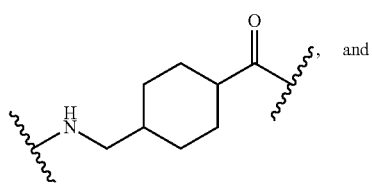

and

Chem. 18

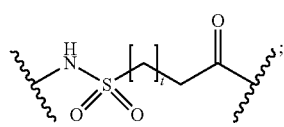

wherein
R is —COOH; each of s, x, y, z, and l independently represents an integer in the range of 8-20; each of r, m, and q independently represents an integer in the range of 0-4; g is an integer in the range of 1-10; h is an integer in the range of 1-2, and t is an integer in the range of 1-5;
BL is an optional branched linker selected from Chem. 19 and Chem. 20:

Chem. 19

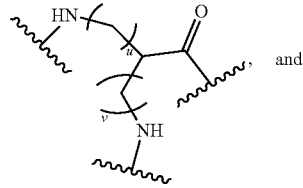

and

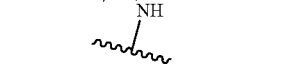

Chem. 20

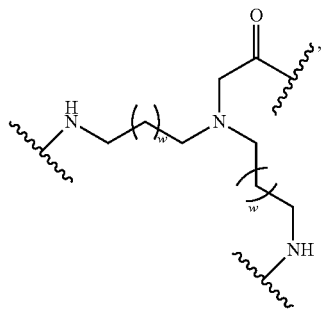

wherein u and v independently represents an integer in the range of 0-5, with the provisos that when u is 0 v is an integer in the range of 1-5, and when v is 0 u is an integer in the range of 1-5; and each w independently represents an integer in the range of 0-2; and
wherein the bond between A and B is an ester bond, the bond between P and L is an amide bond, and if BL is present the bonds between L and BL, and BL and B are amide bonds, or if BL is absent the bond between L and B is an amide bond;

or a salt, amide, or ester thereof.

In some embodiments, when U is 1 and BL is absent, Formula I becomes Formula Ia: P-L-B-A. Examples 1-3 and 8 herein are examples of acylating agents of this type.

In some embodiments, when U is 2 and BL is present, Formula I becomes Formula Ib: (P-L)$_2$-BL-B-A. Examples 4-7 herein are examples of acylating agents of this type. These have a bi-furcated or fork-like structure, where the branched linker, BL, provides the basis of the fork.

In some embodiments, each P in (P-L)$_2$ is substantially identical. In some embodiments, each P in (P-L)$_2$ is identical. In some embodiments, each P in (P-L)$_2$ are different.

In some embodiments, each L in (P-L)$_2$ is substantially identical. In some embodiments, each L in (P-L)$_2$ is identical. In some embodiments, each L in (P-L)$_2$ are different.

In some embodiments, each P-L in (P-L)$_2$ is substantially identical. In some embodiments, each P-L in (P-L)$_2$ is identical. In some embodiments, each P-L in (P-L)$_2$ are different.

In some embodiments, when BL is Chem. 19, and u is 0 and v is 4 (or u is 4 and v is 0), the BL may be referred to as Eps-Lys(Bis) which is a bis-amino tri-radical of lysine. The Chem. 19 element may be in its L- or D-form. In some embodiments, the Chem. 19 element is in the L-form.

In some embodiments, when BL is Chem. 20 and w is 1, the BL may be referred to as. Amino-C3-(Gly(Bis)) which is a bis-amino tri-radical of a derivative of glycine.

In some embodiments, p in Chem. 6 (B) is 1, 2, or 4. In some embodiments, k and n in Chem. 6 are both 1 (Ado).

In some embodiments, P is Chem. 10. In some embodiments, s in Chem. 10 is 8-10, such as 9.

In some embodiments, P is Chem. 11. In some embodiments, x in Chem. 11 is 16 (C18 diacid). In some embodiments, x in Chem. 11 is 18 (C20 diacid).

In some embodiments, L comprises Chem. 15. In some embodiments, when r, m, and q in Chem. 15 are 0, 2, and 1, respectively, Chem. 15 may be referred to as g-Glu (for gamma-Glu). The Chem. 15 element may be in its L- or D-form. In some embodiments, the Chem. 15 element is in the L-form.

In some embodiments, L comprises Chem. 16. In some embodiments, g and h in Chem. 16 are both 1 (Ado). In some embodiments, Chem. 16 is included two times in L. In some embodiments, Chem. 16 is included four times in L. In some embodiments, Chem. 16 is not included in L.

In some embodiments, L comprises Chem. 17, which may be referred to as Trx (tranexamic acid). In some embodiments, Chem. 17 is not included in L.

In some embodiments, L contains from one to six linker elements. In some embodiments, L is selected from gGlu, Trx-gGlu, Trx-gGlu-2×Ado, and Trx-gGlu-4×Ado.

In some embodiments, the acylating agent of the invention is selected from Chem. 21, Chem. 22, Chem. 23, Chem. 24, Chem. 25, Chem. 26, Chem. 27, and Chem. 28; or a pharmaceutically acceptable salt, amide or ester thereof. The structures of Chem. 21-Chem. 28 are shown in Examples 1-8, respectively. In some embodiments, the acylating agent of the invention is selected from Chem. 36, Chem. 37, and Chem. 38; or a pharmaceutically acceptable salt, amide or ester thereof. The structures of Chem. 36-Chem. 38 are shown in Examples 8B-8D, respectively.

Example 9 of the present application compares the hydrolytic stability of activated side chains or acylating agents of the invention with four reference side chains. Example 13 of the present application compares the hydrolytic stability of additional activated side chains or acylating agents of the invention.

In some embodiments, the acylating agent of the invention is hydrolytically more stable than the corresponding NHS-activated acylating agent (NHS is Chem. 2, shown below).

In some embodiments, the acylating agent of the invention is hydrolytically more stable than other chlorine-substituted phenolic activators such as 2,4-DC-phenol and 2,6-DC-phenol (Chem. 3 and Chem. 4, respectively, shown below).

In some embodiments, the acylating agent of the invention is hydrolytically more stable than an acylating agent activated with 3,5-DC-4-HBSA (Chem. 5, shown below), which only differs from the activator for use according to the invention (3,5-DC-2-HBSA, Chem. 1b, shown below) in the position of the hydroxy group on the benzene ring.

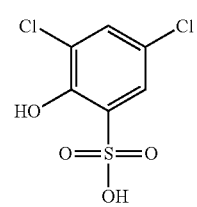

Chem. 1b

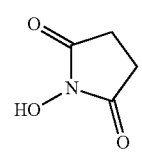

Chem. 2

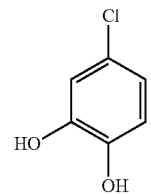

Chem. 3

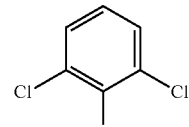

Chem. 4

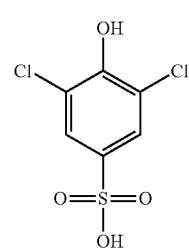

Chem. 5

Additional particular embodiments of the acylating agent of the invention are disclosed below, in the section headed "PARTICULAR EMBODIMENTS".

Method of Preparing the Acylating Agent

The present invention also relates to a method for preparing the acylating agent of the invention.

In some embodiments, the method comprises the step of reacting a compound comprising Chem. 6b or Chem. 6c:

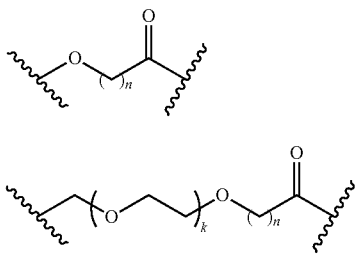

Chem. 6b

Chem. 6c with a compound of Chem. 1c as defined herein.

In some embodiments Chem. 6b may be used as an alternative to Chem. 6a in methods or embodiments herein specifying Chem. 6a. In some embodiments Chem. 6c may be used as an alternative to Chem. 6a in methods or embodiments herein specifying Chem. 6a. In some embodiments Chem. 1c may be used as an alternative to Chem. 1a in methods or embodiments herein specifying Chem. 1a. In some embodiments, the method comprises the step of reacting a compound comprising Chem. 6a:

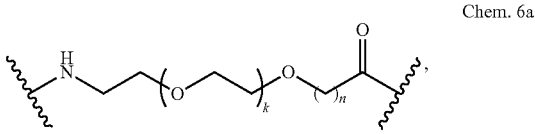

Chem. 6a wherein k is an integer in the range of 1-10, and n is an integer in the range of 1-2; with a compound of Chem. 1a:

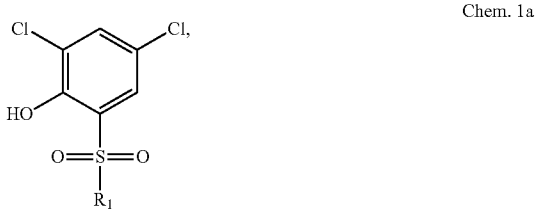

Chem. 1a wherein $R_1$ is OH or a leaving group.

In some embodiments the compound comprising Chem. 6a is a carboxylate of Chem. 6a (carboxylate at the right hand end), which when reacted with Chem. 1a results in a carboxylic-sulfonic mixed anhydride which after a facile intramolecular acyl transfer reaction to the phenolate function results in the acylating agent of the invention.

Alternatively, in some embodiments, the method comprises a one-step esterification reaction between the compound comprising Chem. 6a and the sulfuric acid version of Chem. 1a (Chem. 1a with $R_1$=OH, i.e. Chem. 1b) which results in the acylating agent of the invention. One non-limiting example of a suitable coupling reagent for this reaction is DCC.

In some embodiments of either of these two methods, when the left-hand end of Chem. 6a comprises chemical groups that have been protected (such as carboxylic acid groups protected with, e.g., tBu or Bn), the method also comprises a step of de-protecting the acylating agent.

In some embodiments, the acylating agent prepared by this method is as defined in any of the acylating agent embodiments discussed above and/or in any of the "PARTICULAR EMBODIMENTS" further below.

In some embodiments, the method comprises the step of reacting a compound of Formula Ic: (P-L)$_U$-BL-B, with the compound of Chem. 1a wherein $R_1$ is OH or a leaving group, and wherein P, L, U, BL, and B are as defined in the acylating agent sections above and/or in the "PARTICULAR EMBODIMENTS" further below.

In some embodiments $R_1$ represents halogen. In some embodiments $R_1$ represents Cl. In some embodiments $R_1$ represents OH.

The acylating agent of the invention can be prepared on solid support using procedures of solid phase peptide synthesis well known in the art, or in solution phase as also well known in the art. Non-limiting examples of such preparation methods are included in the Experimental part of the present application.

Additional particular embodiments of the method of preparing the acylating agent of the invention are disclosed below, in the section headed "PARTICULAR EMBODIMENTS".

Method of Using the Acylating Agent

The present invention also relates to a method for acylating an amino group in an amino acid, a peptide, or a protein, the method comprising a step of reacting the amino acid, peptide, or protein with the acylating agent of the invention.

In some embodiments, the acylating agent for use in this method is as defined in any of the acylating agent embodiments discussed above and/or in the "PARTICULAR EMBODIMENTS" further below.

In some embodiments, one or more amino groups in the amino acid, peptide, or protein are acylated. In some embodiments, one, two, or three amino groups are acylated. In some embodiments, one or two amino groups are acylated. In some embodiments, each amino group being acylated is the epsilon-amino group of a Lys residue in the amino acid, peptide, or protein (eps-Lys).

The acylation method of the invention takes place under suitable conditions, which are known by the person skilled in the art. In some embodiments, the acylation reaction takes place in an aqueous reaction medium (a reaction medium that contains water). In some embodiments, the pH in the acylation reaction mixture is in the range of pH 8-14. In some embodiments, the temperature in the reaction mixture is in the range of −5° C. to 50° C. In some embodiments, the acylation reaction is over when the addition of the acylating agent stops. In some embodiments, the method comprises the further step of adjusting pH to pH 6.5-9.0 after addition of acylating agent has stopped.

The acylation method of the present invention is quite robust. For example, it provides great flexibility as regards the addition of the acylating agent of the invention to the amino acid, peptide, or protein to be acylated. Also or alternatively there is no need for the reaction vessel to be of any particular design. Also or alternatively there is no need for the stirring to be optimal or optimised. Example 10 herein demonstrates that the acylating agent of the invention can be added as a solution, and either slowly, fast, or with intermediate speed, or it can be added as a solid—without impacting the yield of the desired product. This is contrary to the known NHS-based acylation method, where the acylating agent has to be added very slowly and under rigorous control due to its hydrolytic instability.

The acylation method of the present invention gives a product of higher purity and/or with a cheaper process as compared to the known NHS-based acylation method. As demonstrated in Examples 10-12 herein, the purity may be at least similar, and/or a smaller amount of the acylating agent (lower surplus or less equivalents of the side chain (Eq SC) relative to the amount of the amino acid, peptide, or protein to be acylated) has to be used.

In some embodiments, the acylation method of the present invention comprises a further step, after the acylation reaction, of purifying the desired product of the acylation reaction. Suitable methods of purifying acylated amino acids, peptides, and proteins are known by the person skilled in the art.

In some embodiments, the acylation method of the present invention comprises a further step, prior to the acylation reaction, of dissolving the amino acid, peptide, or protein to be acylated. In some embodiments, the amino acid, peptide or protein is dissolved in an aqueous solution. Suitable ranges for pH, concentration of amino acid, peptide, or protein, and temperature are known by the person skilled in the art.

The acylation method of the invention refers to "amino acid, peptide, or protein" as it is in principle applicable to any amino acid, peptide, or protein, whatever the size (number of amino acid residues) or other structural parameter.

An amino acid may be defined as a compound which comprises an amine group and a carboxylic acid group. The amine group may, e.g., be a primary or secondary amino group. An amino acid optionally includes one or more additional groups often referred to as an amino acid side chain. Amino acids may be classified in various ways, for example, based on origin, as coded amino acids or non-coded amino acids. Coded amino acids may be defined by reference to IUPAC table 1 in section 3AA-1. Any amino acid can be used in the acylation method of the invention. In some embodiments, the amino acid is a coded amino acid. In some embodiments the amino acid is a non-coded amino acids. One non-limiting example of a non-coded amino acid is Aib (alpa-aminoisobutyric acid).

The distinction between peptide and protein may not always be quite clear. For example, a peptide is sometimes defined so as to contain a maximum of about 50 amino acid residues, a polypeptide sometimes to contain a minimum of about 50 amino acid residues, and a protein sometimes to consist of one or more peptides or polypeptides arranged in a more complex structure which may be required for biological activity. Nevertheless, insulin (which consists of two peptide chains each of a length of less than 50 amino acids, coupled together via Cys-Cys bonds) is traditionally referred to as a peptide.

For the present purpose the following definitions apply: A peptide contains up to a total of 200 amino acid residues, in one or more individual peptide chains; and a protein contains more than 200 amino acids in total, in one or more individual peptide chains.

Non-limiting examples of peptides for use in the method of the invention include Glucagon-Like Peptide-1 (GLP-1) which is a peptide of 31 amino acid residues (native human (GLP-1) in one chain, insulin which is a peptide of 51 amino acid residues in total (native human insulin, 30 amino acids in the B-chain and 21 amino acids in the A-chain), proinsulin which is a peptide of 86 amino acid residues in one chain (native human proinsulin including the A-, B-, and C-peptide), and pre-proinsulin which is a peptide that in addition to the 86 amino acids of proinsulin includes a pre-sequence of 24 amino acid residues in one chain (native human pre-proinsulin).

In some embodiments, the peptide for use in the method of the invention contains a) at least 2 amino acid residues, b) at least 5 amino acid residues, c) at least 20 amino acids; and/or d) a maximum of 150 amino acid residues.

In some embodiments, the protein contains no more than 2000 amino acid residues in total.

In some embodiments, the amino acid, peptide, or protein for use in the acylation method of the invention is an amino acid.

In some embodiments, the amino acid, peptide, or protein for use in the acylation method of the invention is a peptide.

In some embodiments, the amino acid, peptide, or protein for use in the acylation method of the invention is a protein.

The amino acid residues incorporated in the peptide or protein for use in the acylation method of the invention may include coded and/or non-coded amino acid residues. The term "coded amino acids" refers to the 20 "natural" amino acids (see, e.g., IUPAC, table 1, section 3AA-1). One non-limiting example of a non-coded amino acid is Aib, which refers to alpha-aminoisobutyric acid (alternative name alpha-methylalanine). Unless otherwise specified, the amino acid residue(s) in the amino acid, peptide or protein for use in the acylation method of the invention are in the L-form.

In some embodiments, the peptide or protein for use in the acylation method of the invention is a pharmaceutical peptide or protein, which means that the peptide or protein has an effect, demonstrated in vitro or in vivo, which is considered at least potentially relevant for the prophylaxis or treatment of one or more diseases. Non-limiting examples of diseases, include diabetes, obesity, and related diseases and disorders.

Non-limiting examples of peptides or proteins to be acylated using the method of the invention include GLP-1, insulin, pYY, amylin, and analogues thereof.

In some embodiments, the peptide or protein to be acylated is a GLP-1 peptide. The term GLP-1 peptide includes native human GLP-1(7-37) (SEQ ID NO: 1), as well as analogues thereof (GLP-1 analogues). In some embodiments the GLP-1 analogue has a maximum of 10 amino acid changes as compared to GLP-1(7-37) (SEQ ID NO: 1). In some embodiments, the amino acid changes are selected from amino acid substitutions, extensions, and deletions, as compared to GLP-1(7-37) (SEQ ID NO: 1). In some embodiments the GLP-1 analogue comprises an amino acid sequence of Formula III:

Xaa$_7$-Xaa$_8$-Glu-Gly-Thr-Xaa$_{12}$-Thr-Ser-Asp-Xaa$_{16}$-
Ser-Xaa$_{18}$-Xaa$_{19}$-Xaa$_{20}$-Glu-Xaa$_{22}$-Xaa$_{23}$-Ala-
Xaa$_{25}$-Xaa$_{26}$-Xaa$_{27}$-Phe-Ile-Xaa$_{30}$-Xaa$_{31}$-Leu-
Xaa$_{33}$-Xaa$_{34}$-Xaa$_{35}$-Xaa$_{36}$-Xaa$_{37}$-Xaa$_{38}$-Xaa$_{39}$-
Xaa$_{40}$-Xaa$_{41}$-Xaa$_{42}$ (SEQ ID NO: 22);

wherein Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine; Xaa$_8$ is Ala, Gly, Ser, Aib, (1-aminocyclopropyl) carboxylic acid, or (1-aminocyclobutyl) carboxylic acid; Xaa$_{12}$ is Phe or Leu; Xaa$_{16}$ is Val or Leu; Xaa$_{18}$ is Ser, Val, Arg, or Leu; Xaa$_{19}$ is Tyr or Gln; Xaa$_{20}$ is Leu, Lys, or Met; Xaa$_{22}$ is Gly or Glu; Xaa$_{23}$ is Gln, Glu, or Arg; Xaa$_{25}$ is Ala or Val; Xaa$_{26}$ is Lys or Arg; Xaa$_{27}$ is Glu, Lys, or Leu; Xaa$_{30}$ is Ala, Glu, or Arg; Xaa$_{31}$ is Trp or His; Xaa$_{33}$ is Val; Xaa$_{34}$ is Arg, His, Asn, Gly, or Gln; Xaa$_{35}$ is Gly, Ala, or absent; Xaa$_{36}$ is Arg, Lys, Gly, or absent; Xaa$_{37}$ is Gly, Pro, Lys, or absent; Xaa$_{38}$ is Ser, Gly, Ala, Glu, Pro, Lys, or absent; Xaa$_{39}$ is Ser, Gly, Ala, Glu, Pro, or absent; Xaa$_{40}$ is Ser, Gly, Ala, Glu, Pro, or absent; Xaa$_{41}$ is Ser, Gly, Ala, Glu, Pro, or absent; and Xaa$_{42}$ is Lys or absent; wherein at least one of Xaa$_{20}$, Xaa$_{26}$, Xaa$_{27}$, Xaa$_{36}$, Xaa$_{37}$, Xaa$_{38}$, and Xaa$_{42}$ is Lys; with the proviso that if one of Xaa$_{35}$, Xaa$_{36}$, Xaa$_{37}$, Xaa$_{38}$, Xaa$_{39}$, Xaa$_{40}$, or Xaa$_{41}$ is absent, then each of the subsequent amino acids is also absent; or a pharmaceutically acceptable salt, amide, or ester thereof.

In Formula III and similar formulas herein, the numbering of the amino acid residues follows the established practice in the art for native GLP-1, namely that the first (N-terminal) amino acid residue is numbered or accorded position no. 7, and the subsequent amino acid residues downstream towards the C-terminus are numbered 8, 9, 10, and so on, until the last (C-terminal) amino acid residue. In native GLP-1 the C-terminal amino acid residue is Gly, with number 37. However, as it appears from the above formula, in the peptide of Formula III the C-terminal amino acid may be any one of the amino acid residues between Xaa$_{34}$ and Xaa$_{42}$ i.e. have a number of from 34 to 42.

The numbering is done differently in the sequence listing, where the first amino acid residue of SEQ ID NO: 1 (His) is assigned no. 1, and the last (Gly) no. 31. However, herein we follow the established numbering practice in the art, as explained above.

A GLP-1 analogue may be described by reference to i) the number of the amino acid residue in native GLP-1(7-37) which corresponds to the amino acid residue which is changed (i.e., the corresponding position in native GLP-1), and to ii) the actual change.

The "corresponding position" as well as the number and kind of changes, are easily deduced, e.g. by simple handwriting and eyeballing (visual inspection); and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

In some embodiments, the GLP-1 peptide for use in the acylation reaction of the invention is selected from SEQ ID NO: 2, SEQ ID NO: 4, SEQ ID NO: 6, SEQ ID NO: 12, SEQ ID NO:14, SEQ ID NO: 16, and SEQ ID NO: 18; or a pharmaceutically acceptable salt, amide or ester thereof.

In some embodiments, the peptide or protein for use in the acylation reaction of the invention is a precursor of a GLP-1 peptide, wherein the two amino acids corresponding to the amino acid residues at position 7 and 8 of GLP-1(7-37) (SEQ ID NO: 1) have been deleted. The precursor GLP-1 peptide is in all other respects as defined above and in the "PARTICULAR EMBODIMENTS" further below. In some embodiments, the precursor is selected from SEQ ID NO: 3, SEQ ID NO: 5, SEQ ID NO: 7, SEQ ID NO: 13, SEQ ID NO: 15, SEQ ID NO: 17, and SEQ ID NO: 19; or a pharmaceutically acceptable salt, amide, or ester thereof.

In some embodiments, the precursor is prepared by recombinant expression. Suitable recombinant expression methods are known by the person skilled in the art, see e.g. Examples 1-3 of WO 2009/083549. In some embodiments, the precursor is purified prior to being acylated according to the invention. In some embodiments, the acylated precursor, product of the acylation reaction of the invention, is purified in a further step.

In some embodiments, the acylated precursor is reacted (ligated) with a protected (His-Aib) di-peptide of Chem. 8:

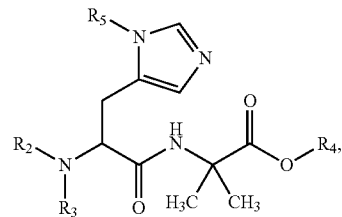

wherein R$_2$ is H or an amino protecting group, and R$_3$ is an amino protecting group; or R$_2$ is a removable alkyl group, and R$_3$ is H or a removable alkyl group; or R$_2$ and R$_3$ are jointly forming a ring; R$_4$ is H, or a secondary ammonium cation, a tertiary ammonium cation or a metal cation forming a salt with the carboxylate group; and R$_5$ is absent or an acidic salt, resulting in the corresponding acylated full-length peptide or protein with protection groups at the N-terminus of the peptide or protein.

Suitable ligation reaction conditions including preferred R groups in Chem. 8, and how to remove the protection groups at the N-terminus are disclosed in WO 2013/098191.

In some embodiments, the acylation method of the invention when applied to a GLP-1 precursor peptide includes one or more of the following additional steps: (i) purifying the acylated precursor, (ii) ligating the Chem. 8 di-peptide to it, (iii) de-protecting the N-terminus, and (iv) purifying the resulting acylated full-length GLP-1 peptide.

In some embodiments, the acylated GLP-1 peptides (excluding the precursors) which are produced using the acylation method of the invention are GLP-1 receptor agonists.

A receptor agonist may be defined as an analogue that binds to a receptor and elicits a response typical of the natural ligand (see e.g. "Principles of Biochemistry", AL Lehninger, DL Nelson, MM Cox, Second Edition, Worth Publishers, 1993, page 763). Thus, for example, a "GLP-1 receptor agonist" may be defined as a compound which is capable of binding to the human GLP-1 receptor and capable of activating it. Suitable GLP-1 receptor binding and GLP-1 receptor activation assays are known in the art. See e.g. Examples 33 and 34 in WO 2016/083499.

In some embodiments, the peptide or protein to be acylated using the method of the invention is an insulin peptide. The term insulin peptide includes human insulin, human proinsulin, human pre-proinsulin, and analogues thereof. The sequences of human insulin, human proinsulin, and human pre-proinsulin are known in the art. In some embodiments, the insulin analogue for use in the acylation method of the invention has a maximum of 10 amino acid changes as compared to human insulin. In some embodiments the maximum of 10 amino acid changes is as compared to human proinsulin. In some embodiments, the insulin analogue comprises at least one of the following amino acid changes: A14E, B16H, B25H, desB27, and/or desB30. The terminology used herein for naming insulin analogues is as usual in the art, as explained in, e.g., WO 2009/115469. Thus, for example, A14E refers to the amino acid corresponding to amino acid residue no. 14 in the A-chain of human insulin having been replaced by Glu (E); B16H refers to the amino acid corresponding to amino acid residue no. 16 in the B-chain of human insulin having been replaced by His (H); and desB30 refers to the amino acid corresponding to amino acid residue no. 30 in the B-chain of human insulin having been deleted. For identifying corresponding residues/position numbers, simple handwriting and visual inspection can be used, and/or an alignment program such as align, as discussed above for GLP-1 analogues. In some embodiments, the insulin analogue for use in the acylation method of the present invention is selected from i) A14E, B25H, desB27, desB30 human insulin (SEQ ID NOs: 8 and 9); ii) A14E, B25H, desB30 human insulin (SEQ ID NOs: 10 and 11); iii) A14E, B16H, B25H, desB30 human insulin (SEQ ID NOs: 20 and 21); or a pharmaceutically acceptable salt, amide, or ester thereof.

In some embodiments the insulin peptide for use in the acylation method of the invention is an analogue of human proinsulin, which can be prepared by recombinant expression. Suitable recombinant expression methods are known by the person skilled in the art, see e.g. WO 2009/115469 referred to above. In some embodiments, the acylation method of the invention when applied to an analogue of human proinsulin includes one or more of the following additional steps: (i) purifying the acylated proinsulin analogue, (ii) cleaving off the C-peptide part (e.g. enzymatically), and (iii) purifying the acylated insulin peptide.

In some embodiments, the final acylated insulin peptide produced by the acylation method of the invention (excluding acylated proinsulin, pre-proinsulin, and analogues thereof) has affinity to an insulin receptor. Suitable insulin receptor affinity assays are known in the art, see e.g. Example 178 of WO 2009/115469. Using this assay with 0% HSA the final acylated insulin peptide produced according to the invention has an affinity of at least 0.10%.

In some embodiments, the peptide or protein to be produced by the method of the invention is a pYY receptor agonist. Non-limiting examples of suitable pYY receptor agonists are disclosed in WO 2015/071355 and WO 2015/071356.

In some embodiments, the peptide or protein being produced by the method of the invention is an amylin receptor agonist. Non-limiting examples of suitable amylin receptor agonists are disclosed in WO 2016/034604, WO 2012/168430, WO 2012/168431, and WO 2012/168432.

In some embodiments, the acylation method of the invention includes a further step of removing a secretory signal sequence from the peptide or protein. The secretory signal sequence may be in the form of an N-terminal and/or C-terminal extension, see e.g. p. 44 of WO 2009/083549.

In some embodiments of the acylation method of the invention, the N-terminal amino acid of the peptide or protein is negatively charged. One non-limiting example of a negatively charged amino acid residue is Glu.

Additional particular embodiments of the method of using the acylating agent of the invention are disclosed below, in the section headed "PARTICULAR EMBODIMENTS".

Novel GLP-1 Precursor Compounds

The present invention also relates to the following novel compounds:

(xi) a compound as shown in Example 3 of WO 2015/000942 in which the two N-terminal amino acids have been deleted, (xii) a compound as shown in Example 11 of WO 2015/000942 in which the two N-terminal amino acids have been deleted, (xiv) a compound as shown in Example 31 of WO 2012/140117 in which the two N-terminal amino acids have been deleted, (xv) a compound as shown in Example 5 of WO 2012/140117 in which the two N-terminal amino acids have been deleted, (xvi) a compound as shown in Example 2 of WO 2011/080103 in which the two N-terminal amino acids have been deleted, (xvii) a compound as shown in Example 14 of WO 2016/097108 in which the two N-terminal amino acids have been deleted, (xiix) a compound as shown in Example 1 of WO 2016/097108 in which the two N-terminal amino acids have been deleted, (xix) a compound as shown in Example 11 of WO 2016/083499 in which the two N-terminal amino acids have been deleted, (xx) a compound as shown in Example 12 of WO 2016/083499 in which the two N-terminal amino acids have been deleted, wherein the relevant Examples of each of the WO publications referred to in (xi)-(xii) and (xiv)-(xx) above are incorporated herein by reference; or a compound having the sequence of SEQ ID NO: 3, SEQ ID NO: 5, SEQ ID NO: 13, SEQ ID NO: 15, SEQ ID NO: 17, or SEQ ID NO: 19; or a pharmaceutically acceptable salt, amide, or ester thereof.

Salts, Amides and Esters

The activated side chain of the invention (the acylating agent), the peptide and protein for use in the acylation method of the invention and the resulting acylated peptide and protein, as well as the novel GLP-1 precursor compound of the invention may be in the form of a salt, amide, or ester. In some embodiments the salt, amide, or ester is pharmaceutically acceptable. In some embodiments, the salt, amide, or ester is formed at one or more chemical groups of the compound in question.

Salts are e.g. formed by a chemical reaction between a base and an acid, e.g.: $2NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts may be formed with added cations or anions between anionic or cationic groups, respectively. These groups may be situated in, e.g., the peptide moiety, and/or in the side chain moiety.

Non-limiting examples of anionic groups include free carboxylic groups and free sulfonic acid groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group.

The ester formation may involve the free carboxylic group at the C-terminus of the peptide, and/or any free carboxylic group in the side chain.

The amide of the derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In some embodiments, the pharmaceutically acceptable salt, amide, or ester is a pharmaceutically acceptable salt. In some embodiments, the pharmaceutically acceptable salt, amide, or ester is a pharmaceutically acceptable amide, preferably with an amide group at the C-terminus of the peptide. In some embodiments, the pharmaceutically acceptable salt, amide, or ester is a pharmaceutically acceptable ester.

Unless otherwise defined herein, the term "a" means "one or more".

Unless otherwise defined herein, the term "about" means +/−10%.

Unless otherwise defined herein, terms presented in singular form also include the plural situation.

Particular Embodiments

The following are particular embodiments of the invention:
1. A compound which comprises Chem. 7:

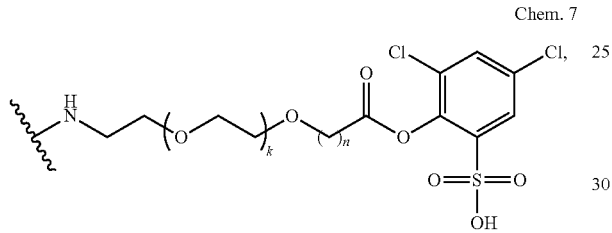

Chem. 7 wherein k is an integer in the range of 1-10, and n is an integer in the range of 1-2; or a salt thereof.
2. The compound of embodiment 1, wherein k is 1.
3. The compound of any of embodiments 1 and 2, wherein n is 1.
4. The compound of any of embodiments 1-3, wherein the salt is a sulfonic acid salt.
5. The compound of embodiment 4, wherein the sulfonic acid salt is a tertiary amine salt such as a TEA salt, or an alkali metal salt such as a K salt, a Na salt, or a Li salt.
6. The compound of any of embodiments 1-5 in the form of the TEA salt.
6a. The compound of any of embodiments 1-6 in the form of an alkali metal salt.
7. The compound of any of embodiments 1-6a, which comprises Formula I:

(P-L)$_U$-BL-B-A,   Formula I:

wherein
A is an activator of Chem. 1:

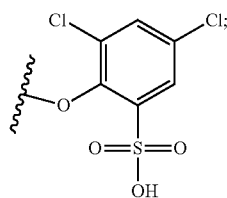 [SMILES: *Oc1c(Cl)cc(Cl)cc1S(=O)(=O)O]

B is a linker element of Chem. 6:

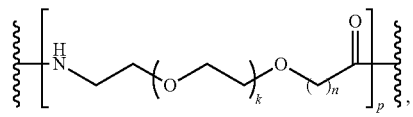

wherein k is an integer in the range of 1-10, n is an integer in the range of 1-2, and p is an integer in the range of 1-5 with the proviso that if k>1 then p is 1;

U represents the number of groups (P-L) in the compound and is 1 or 2; each group (P-L) comprises a protracting moiety (P) independently selected from Chem. 10, Chem. 11, Chem. 12, Chem. 13, and Chem. 14:

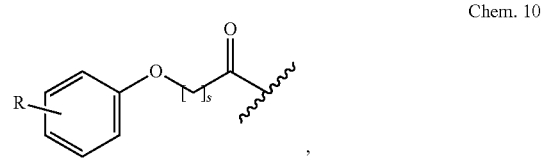

Chem. 10

Chem. 11

Chem. 12

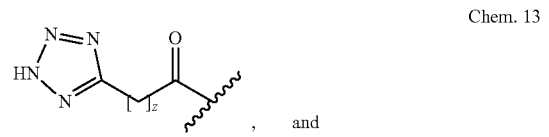

Chem. 13 and

Chem. 14 and a linker (L) comprising at least one linker element selected from Chem. 15, Chem. 16, Chem. 17, and Chem. 18:

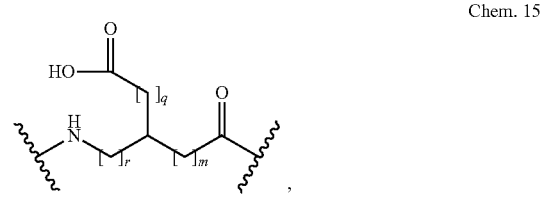

Chem. 15

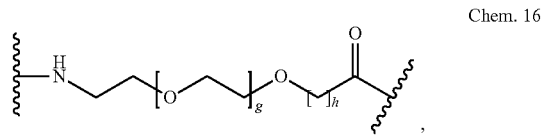

Chem. 16

-continued

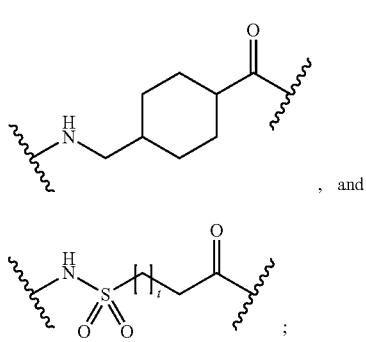

Chem. 17

, and

Chem. 18 wherein
R is —COOH; each of s, x, y, z, and l independently represents an integer in the range of 8-20; each of r, m, and q independently represents an integer in the range of 0-4; g is an integer in the range of 1-10; h is an integer in the range of 1-2, and t is an integer in the range of 1-5;
BL is an optional branched linker selected from Chem. 19 and Chem. 20:

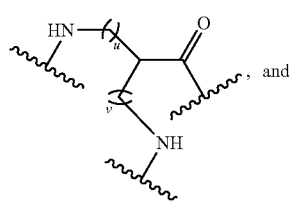

Chem. 19

, and

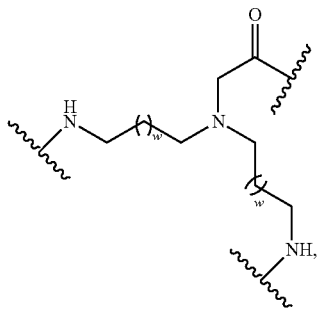

Chem. 20 wherein u and v independently represents an integer in the range of 0-5, with the provisos that when u is 0 v is an integer in the range of 1-5, and when v is 0 u is an integer in the range of 1-5; and each w independently represents an integer in the range of 0-2; and
wherein the bond between A and B is an ester bond, the bond between P and L is an amide bond, and
if BL is present the bonds between L and BL, and BL and B are amide bonds, or if BL is absent the bond between L and B is an amide bond;
or a salt, amide, or ester thereof.

8. The compound of embodiment 7, wherein the salt, amide, or ester is a salt of A, and/or a carboxylic acid salt, a carboxylic acid amide, a carboxylic acid ester, a sulfonic acid salt, a sulfonic acid amide, and/or a sulfonic acid ester of P-L.
9. The compound of any of embodiments 7-8, wherein A is an activator of Chem. 1, or a salt thereof.
10. The compound of embodiment 9, wherein the salt of A is a sulfonic acid salt.
11. The compound of embodiment 10, wherein the sulfonic acid salt of A is a tertiary amine salt such as a TEA salt or an alkali metal salt such as a K salt, a Na salt, or a Li salt.
11a. The compound of any of embodiments 7-11 in the form of its TEA salt of A.
11b. The compound of any of embodiments 7-11 in the form of its alkali metal salt of A.
11c. The compound of any of embodiments 7-11b, wherein the salt, amide, or ester is a carboxylic acid salt, a carboxylic acid amide, a carboxylic acid ester, a sulfonic acid salt, a sulfonic acid amide, and/or a sulfonic acid ester of P-L.
11d. The compound of embodiment 11c, wherein P is Chem. 10 or a carboxylic acid salt, a carboxylic acid amide, or a carboxylic acid ester thereof.
11e. The compound of embodiment 11c, wherein P is Chem. 11 or a carboxylic acid salt, a carboxylic acid amide, or a carboxylic acid ester thereof.
11f. The compound of embodiment 11c, wherein P is Chem. 14 or a sulfonic acid salt, a sulfonic acid amide, or a sulfonic acid ester thereof.
11g. The compound of any of embodiments 7-11f, wherein L is Chem. 15 or a carboxylic acid salt, a carboxylic acid amide, or a carboxylic acid ester thereof.
11h. The compound of any of embodiments 7-11g, wherein the salt, amide or ester is pharmaceutically acceptable.
11i. The compound of any of embodiments 7-11h, wherein the salt, amide or ester is a salt.
12. The compound of any of embodiments 7-11a, which has Formula I.
13. The compound of any of embodiments 7-12, wherein k is 1.
14. The compound of any of embodiments 7-13, wherein n is 1.
15. The compound of any of embodiments 7-14, wherein p is 1, 2, or 4.
16. The compound of any of embodiments 7-15, wherein p is 1.
17. The compound of any of embodiments 7-15, wherein p is 2.
18. The compound of any of embodiments 7-15, wherein p is 4.
19. The compound of any of embodiments 7-18, wherein P is Chem. 10.
20. The compound of any of embodiments 7-19, wherein R is at position 3 of the benzene ring (m).
21. The compound of any of embodiments 7-20, wherein R is at position 4 of the benzene ring (p).
22. The compound of any of embodiments 7-21, wherein s is 8-20.
23. The compound of any of embodiments 7-22, wherein s is 8-10.
24. The compound of any of embodiments 7-23 wherein s is 9.
25. The compound of any of embodiments 7-18, wherein P is Chem. 11.
26. The compound of any of embodiments 7-18 and 25, wherein x is 8-20.
27. The compound of any of embodiments 7-18 and 25-26, wherein x is 12-20.
28. The compound of any of embodiments 7-18 and 25-27, wherein x is 16.

29. The compound of any of embodiments 7-18 and 25-28, wherein x is 18.
30. The compound of any of embodiments 7-18, wherein P is Chem. 12.
31. The compound of any of embodiments 7-18 and 30, wherein y is 8-20.
32. The compound of any of embodiments 7-18 and 30-31, wherein y is 12-20.
33. The compound of any of embodiments 7-18 and 30-32, wherein y is 14.
34. The compound of any of embodiments 7-18, wherein P is Chem. 13.
35. The compound of any of embodiments 7-18 and 34, wherein z is 8-20.
36. The compound of any of embodiments 7-18 and 34-35, wherein z is 13-17.
37. The compound of any of embodiments 7-18 and 34-36, wherein z is 15.
38. The compound of any of embodiments 7-18, wherein P is Chem. 14.
39. The compound of any of embodiments 7-18 and 38, wherein l is 8-20.
40. The compound of any of embodiments 7-18 and 38-39, wherein l is 13-17.
41. The compound of any of embodiments 7-18 and 38-40, wherein l is 15.
41a. The compound of any of embodiments 7-41, wherein P is selected from
i) Chem. 10 wherein y is 9;
ii) Chem. 11 wherein x is 16; and
iii) Chem. 11 wherein x is 18.
41b. The compound of embodiment 41a i).
41c. The compound of embodiment 41a ii).
41d. The compound of embodiment 41a iii).
42. The compound of any of embodiments 7-41d, wherein L comprises linker element Chem. 15.
43. The compound of any of embodiments 7-42, wherein each of r, m, and q, independently, is 0-4.
44. The compound of any of embodiments 7-43, wherein r is 0, m is 2, and q is 1.
45. The compound of any of embodiments 7-44, wherein L comprises from 0 to 6 times of linker element Chem. 16.
46. The compound of any of embodiments 7-45, wherein g is an integer in the range of 1-10.
47. The compound of any of embodiments 7-46, wherein h is an integer in the range of 1-2.
48. The compound of any of embodiments 7-47, wherein g is 1.
49. The compound of any of embodiments 7-48, wherein h is 1.
50. The compound of any of embodiments 7-49, wherein each of g and h is 1.
51. The compound of any of embodiments 7-50, wherein L comprises 0 times Chem. 16, viz. does not comprise Chem. 16.
52. The compound of any of embodiments 7-50, wherein L comprises 2 times Chem. 16.
53. The compound of any of embodiments 7-50, wherein L comprises 4 times Chem. 16.
54. The compound of any of embodiments 7-53, wherein L comprises from 0 to 1 times of linker element Chem. 17.
55. The compound of any of embodiments 7-54, wherein L comprises 0 times Chem. 17, viz. does not comprise Chem. 17.
56. The compound of any of embodiments 7-54, wherein L comprises Chem. 17.
57. The compound of any of embodiments 7-56, wherein L comprises from 0 to 1 time of linker element Chem. 18.
58. The compound of any of embodiments 7-57, wherein t is 1-5.
59. The compound of any of embodiments 7-58, wherein t is 2.
60. The compound of any of embodiments 7-59, wherein L comprises 0 times Chem. 18, viz. does not comprise Chem. 18.
61. The compound of any of embodiments 7-59, wherein L comprises Chem. 18.
62. The compound of any of embodiments 7-61, wherein if there is more than one linker element the linker elements are interconnected via amide bonds.
63. The compound of any of embodiments 7-62, wherein
a) if there is more than one linker element these are interconnected and together constitute the linker, L; or
b) if there is only one linker element this element constitutes the linker L.
64. The compound of any of embodiments 7-63, wherein at least one linker element means a number of linker elements in the (each) group (P-L) in the range of 1-8.
65. The compound of any of embodiments 7-64, which contains from 1 to 6 linker elements in the (each) group (P-L).
66. The compound of any of embodiments 7-65, wherein the (each) linker L is selected from the following:
a) one linker element Chem. 15 wherein r is 0, m is 2, and q is 1 (Chem. 15);
b) one linker element Chem. 17 and one linker element Chem. 15 wherein r is 0 m is 2 and q is 1, interconnected via amide bonds and in the sequence indicated (Chem. 17 Chem. 15);
c) one linker element Chem. 17, one linker element Chem. 15 wherein r is 0 m is 2 and q is 1, and two linker elements Chem. 16 wherein g is 1 and h is 1, interconnected via amide bonds and in the sequence indicated (Chem. 17-Chem. 15-2×Chem. 16); and
d) one linker element Chem. 17, one linker element Chem. 15 wherein r is 0 m is 2 and q is 1, and four linker elements Chem. 16 wherein g is 1 and h is 1, interconnected via amide bonds and in the sequence indicated (Chem. 17-Chem. 15-4×Chem.16).
67. The compound of embodiment 66 a).
68. The compound of embodiment 66 b).
69. The compound of embodiment 66 c).
70. The compound of embodiment 66 d).
71. The compound of any of embodiments 7-70, wherein the (each) group (P-L) consists of a protracting moiety (P) and a linker (L) as defined in any of embodiments 19-41d and 42-70, respectively.
72. The compound of any of embodiments 7-71, wherein the (each) group (P-L) consists of a protracting moiety (P) and a linker (L) as defined in any of embodiments 41a-41d and 66-70, respectively.
73. The compound of any of embodiments 7-72, wherein U is 1.
74. The compound of embodiment 73, wherein BL is absent.
75. The compound of any of embodiments 7-74, which comprises Formula Ia:

P-L-B-A.                               Formula Ia:

76. The compound of any of embodiments 7-75, which has Formula Ia.
77. The compound of any of embodiments 7-72, wherein U is 2.
78. The compound of embodiment 77, wherein BL is present.
79. The compound of any of embodiments 7-72 and 77-78, which comprises Formula Ib:

(P-L)₂-BL-B-A.  Formula Ib:

80. The compound of any of embodiments 7-72 and 77-79, which has Formula Ib.
81. The compound of any of embodiments 7-72 and 77-80, wherein BL is Chem. 19.
82. The compound of any of embodiments 7-72 and 77-81, wherein u and v independently represents an integer in the range of 0-5, with the provisos that when u is 0 v is 1-5, and when v is 0 u is 1-5.
83. The compound of any of embodiments 7-72 and 77-82, wherein u is 0 and v is 4.
84. The compound of any of embodiments 7-72 and 77-82, wherein u is 4 and v is 0.
85. The compound of any of embodiments 7-72 and 77-80, wherein BL is Chem. 20.
86. The compound of any of embodiments 7-72, 77-80, and 85, wherein each w, independently, is 0-2.
87. The compound of any of embodiments 7-72, 77-80, and 85-86, wherein each w is 1.
88. A compound selected from Chem. 21, Chem. 22, Chem. 23, Chem. 24, and Chem. 25, Chem. 26, Chem. 27, and Chem. 28; or a pharmaceutically acceptable salt, amide, or ester thereof.
89. The compound of embodiment 88, which is a compound of any of embodiments 1-87.
89a. The compound of any of embodiments 1-6b which is hydrolytically more stable than a comparative compound which is identical to said compound except for the fact that Chem. 7 has been replaced by Chem. 7a:

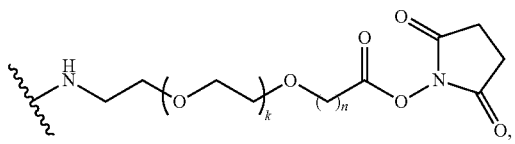

Chem. 7a wherein k and n are as defined in any of embodiments 1-3.
89b. The compound of any of embodiments 7-89 which is hydrolytically more stable than a comparative compound which is identical to said compound except for the fact that activator A of Chem. 1 has been replaced by the following activator of Chem. 2a:

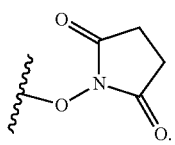

Chem. 2a

89c. The compound of any of embodiments 89a-89b, wherein the hydrolytic stability is determined on a 0.1 M solution of the compound and the comparative compound, respectively, dissolved in NMP, in a suitable buffer solution at a pH of about 10.3, and at room temperature, the reaction mixtures being analysed at a desired point in time by UPLC, and the respective hydrolysis percentages being estimated by area comparison in UV detection at 210 nm.
89d. The compound of any of embodiments 89a-89c, wherein hydrolytic stability is determined generally as described in Example 9.
90. A method for preparing the compound of embodiment 1, which comprises the step of reacting a compound comprising Chem. 6a:

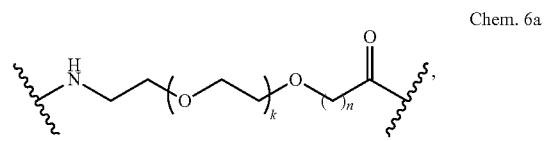

Chem. 6a wherein k is an integer in the range of 1-10, and n is an integer in the range of 1-2; with a compound of Chem. 1a:

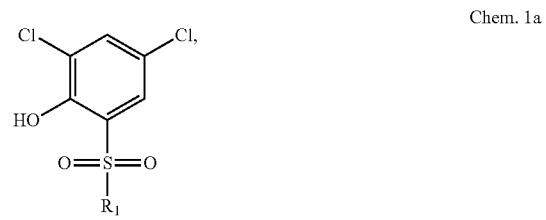

Chem. 1a wherein R₁ is OH or a leaving group.
91. The method of embodiment 90, which is for preparing the compound of any of embodiments 1-6a and wherein each of k and n is correspondingly defined.
92. The method of any of embodiments 90-91, which is for preparing the compound of any of embodiments 1-89d.
93. The method of any of embodiments 90-92, which is for preparing the compound of any of embodiments 88-89d.
94. The method of any of embodiments 90-93, which takes place under suitable conditions.
95. The method of any of embodiments 90-94, which comprises a step of purifying the desired compound.
96. The method of any of embodiments 90-95, wherein R₁ represents halogen.
97. The method of any of embodiments 90-96, wherein R₁ represents Cl.
97a. The method of any of embodiments 90-95, wherein R₁ represents OH.
98. A method for preparing a compound of embodiment 7, which comprises the step of reacting a compound of Formula Ic:

(P-L)_U-BL-B,  Formula Ic:

wherein P, L, U, BL, and B are as defined in embodiment 7, with a compound of Chem. 1a:

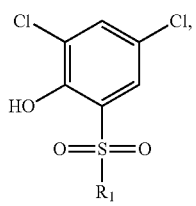

Chem. 1a wherein $R_1$ is OH or a leaving group.

99. The method of embodiment 98, which is for preparing the compound of any of embodiments 7-89d, and wherein each of P, L, U, BL, and B is correspondingly defined.
100. The method of any of embodiments 98-99, which is for preparing the compound of any of embodiments 88-89d, and wherein each of P, L, U, BL, and B is correspondingly defined.
101. The method of any of embodiments 98-100, which takes place under suitable conditions.
102. The method of any of embodiments 98-101, wherein relevant reactive groups, if any, in Formula Ic are suitably protected.
103. The method of any of embodiments 98-101, which comprises a step of purifying the desired compound.
104. The method of any of embodiments 98-103, wherein $R_1$ represents halogen.
105. The method of any of embodiments 98-104, wherein $R_1$ represents Cl.
105a. The method of any of embodiments 98-103, wherein $R_1$ represents OH.
106. A method for acylating an amino group in an amino acid, a peptide, or a protein, the method comprising a step of reacting the amino acid, peptide, or protein with a compound as defined in any of embodiments 1-89d.
107. A method for acylating an amino group in an amino acid, a peptide, or a protein, the method comprising a step of reacting the amino acid, peptide, or protein with a compound as defined in any of embodiments 1-6a.
108. A method for acylating an amino group in an amino acid, a peptide, or a protein, the method comprising a step of reacting the amino acid, peptide, or protein with a compound as defined in any of embodiments 7-89d.
109. A method for acylating an amino group in an amino acid, a peptide, or a protein, the method comprising a step of reacting the amino acid, peptide, or protein with a compound as defined in any of embodiments 88-89d.
110. The method of any of embodiments 106-109, wherein the amino acid, peptide or protein has two or more reactive nucleophilic functional groups.
111. The method of any of embodiments 106-110, wherein the amino group of the amino acid, peptide, or protein is selectively acylated.
112. The method of any of embodiments 106-111, wherein the resulting acylated amino acid, peptide, or protein comprises at least one reactive nucleophilic functional group which is not or only partially acylated.
113. The method of any of embodiments 106-112, for acylating one or more amino groups in the amino acid, peptide, or protein.
114. The method of any of embodiments 106-113, for acylating up to five amino groups in the amino acid, peptide, or protein.
114a. The method of any of embodiments 106-114, for acylating one, two, or three amino groups in the amino acid, peptide, or protein.
114b. The method of any of embodiments 106-114a, for acylating one or two amino groups in the amino acid, peptide, or protein.
115. The method of any of embodiments 106-114b, for acylating one amino group in the amino acid, peptide, or protein.
116. The method of any of embodiments 106-115, for acylating two amino groups in the amino acid, peptide, or protein.
117. The method of any of embodiments 106-116, wherein the/each amino group is the epsilon amino group of a Lys residue of the amino acid, peptide, or protein.
117a. The method of any of embodiments 106-112, wherein the amino acid, peptide, or protein is a peptide or a protein.
118. The method of any of embodiments 106-117a, wherein relevant reactive groups if any are suitably protected.
119. The method of any of embodiments 106-118, which takes place under suitable conditions.
120. The method of any of embodiments 106-119, wherein the compound as defined in any of embodiments 1-89d, 1-6a, 7-89d, and 88-89d is an acylating agent.
121. The method of embodiment 120, wherein the reaction between the amino group of the amino acid, peptide, or protein with the acylating agent is an acylation reaction.
122. The method of embodiment 121, wherein the acylation reaction takes place in a reaction mixture which is an aqueous medium.
123. The method of any of embodiments 121-122, wherein the pH in the reaction mixture is in the range of pH 8-14.
124. The method of any of embodiments 121-123, wherein the pH in the reaction mixture is in the range of pH 9-13.
125. The method of any of embodiments 121-124, wherein the pH in the reaction mixture is in the range of pH 10-12.
126. The method of any of embodiments 121-125, wherein the pH in the reaction mixture is in the range of pH 10.5-12.0.
127. The method of any of embodiments 121-126, wherein the pH in the reaction mixture is in the range of pH 11.0-12.0.
128. The method of any of embodiments 121-127, wherein the pH in the reaction mixture is in the range of pH 11.2-11.8.
129. The method of any of embodiments 121-128, wherein the pH in the reaction mixture is in the range of pH 11.2-11.5.
130. The method of any of embodiments 121-128, wherein the pH in the reaction mixture is in the range of pH 11.5-11.8.
131. The method of any of embodiments 121-130, wherein the temperature in the reaction mixture is in the range of −5 (minus 5)–50° C.
132. The method of any of embodiments 121-131, wherein the temperature in the reaction mixture is in the range of 0-50° C.

133. The method of any of embodiments 121-132, wherein the temperature in the reaction mixture is in the range of 10-30° C.
134. The method of any of embodiments 121-133, wherein the temperature in the reaction mixture is about 20° C.
135. The method of any of embodiments 121-134, wherein the temperature in the reaction mixture is RT (room temperature).
136. The method of any of embodiments 121-132, wherein the temperature in the reaction mixture is in the range of 0-7° C.
137. The method of any of embodiments 121-132 and 136, wherein the temperature in the reaction mixture is in the range of 2-6° C.
138. The method of any of embodiments 121-132 and 136-137, wherein the temperature in the reaction mixture is about 5° C.
139. The method of any of embodiments 121-138, wherein the reaction mixture comprises a buffer.
140. The method of embodiment 139, wherein the buffer is selected from Phosphate buffer, Sodium carbonate buffer, Bicine buffer (N,N-Bis(2-hydroxyethyl)glycine buffer), HEPPS buffer (3-[4-(2-Hydroxyethyl)-1-piperazinyl]propanesulfonic acid buffer), HEPES buffer (4-(2-Hydroxyethyl)-1-piperazineethanesulfonic acid buffer), MOPS buffer (3-(N-Morpholino)propanesulfonic acid buffer), Tris buffer (2-Amino-2-(hydroxymethyl)propane-1,3-diol), and TEA solution.
141. The method of any of embodiments 121-140, wherein the reaction takes from 0-24 hours, counted from the point in time where the addition of the acylating agent starts.
142. The method of any of embodiments 121-141, wherein the reaction takes from 0-12 hours, counted from the point in time where the addition of the acylating agent starts.
143. The method of any of embodiments 121-142, wherein the reaction takes from 0-6 hours, counted from the point in time where the addition of the acylating agent starts.
144. The method of any of embodiments 121-143, wherein the reaction takes from 0-3 hours, counted from the point in time where the addition of acylating agent starts.
145. The method of any of embodiments 121-144, wherein the reaction takes from 0-1.5 hours, counted from the point in time where the addition of acylating agent starts.
146. The method of any of embodiments 121-145, wherein the reaction time is the time used for addition of the acylating agent.
147. The method of any of embodiments 121-146, wherein the acylation reaction is over when the addition of the acylating agent stops.
148. The method of any of embodiments 121-147, comprising the further step of adjusting the pH to pH 6.5-9.0 after addition of the acylating agent has stopped.
149. The method of embodiment 148, wherein the pH is adjusted to pH 7.5-8.0.
150. The method of any of embodiments 148-149, wherein the pH is adjusted immediately after addition of acylating agent has stopped.
151. The method of any of embodiments 121-150, wherein the acylating agent is added as a solution or in solid form to a solution of the amino acid, peptide, or protein.
152. The method of any of embodiments 121-151, wherein the acylating agent is added as a solution.
153. The method of any of embodiments 121-152, wherein the acylating agent is dissolved in a solvent.
154. The method of embodiment 153, wherein the solvent is selected from ethanol, isopropanol, N-methylpyrrolidinone (NMP), N,N-dimethylformamide (DMF), and acetonitril ($CH_3CN$).
155. The method of any of embodiments 121-154, wherein the concentration of the acylating agent is in the range of 10-1000 mg/mL.
156. The method of any of embodiments 121-155, wherein the concentration of the acylating agent is in the range of 10-500 mg/mL.
157. The method of any of embodiments 121-156, wherein the concentration of the acylating agent is in the range of 10-250 mg/mL.
158. The method of any of embodiments 121-157, wherein the concentration of the acylating agent is in the range of 50-250 mg/mL.
159. The method of any of embodiments 121-158, wherein the concentration of the acylating agent is in the range of 100-200 mg/mL.
160. The method of any of embodiments 151-159, wherein the dissolved acylating agent is added to the reaction mixture over a period of between 0 and 480 minutes.
161. The method of any of embodiments 151-160, wherein the dissolved acylating agent is added over a period of between 30 and 60 minutes.
162. The method of any of embodiments 151-161, wherein the dissolved acylating agent is added over a period of between 10 and 45 minutes.
163. The method of embodiment 151, wherein the acylating agent is added in solid form.
164. The method of embodiment 163, wherein the solid acylating agent is added to the reaction mixture over a period of between 0 and 240 minutes.
165. The method of any of embodiments 163-164, wherein the solid acylating agent is added over a period of between 0 and 60 minutes.
166. The method of any of embodiments 163-165, wherein the solid acylating agent is added to the reaction mixture over a period of between 0 and 30 minutes.
167. The method of any of embodiments 121-166, which is with stirring or agitation.
168. The method of any of embodiments 121-167, wherein the number of moles of acylating agent used for each mole of the amino acid, peptide, or protein is in the range of 1.0-10.0.
169. The method of any of embodiments 121-168, wherein the number of moles of acylating agent used for each mole of the amino acid, peptide, or protein is in the range of 1.0-7.5.
170. The method of any of embodiments 121-169, wherein the number of moles of acylating agent used for each mole of the amino acid, peptide, or protein is in the range of 1.0-5.0.
171. The method of any of embodiments 121-170, which is for acylating one or two amino groups in the amino acid, peptide, or protein, wherein the number of moles of acylating agent used for each mole of the amino acid, peptide, or protein is in the range of 1.0-5.0.
172. The method of embodiment 171, wherein the number of moles of acylating agent used for each mole of the amino acid, peptide, or protein is in the range of 1.0-4.0.
173. The method of any of embodiments 171-172, wherein the number of moles of acylating agent used for each mole of the amino acid, peptide, or protein is in the range of 1.0-3.0.
174. The method of any of embodiments 121-170, which is for acylating one amino group in the amino acid, peptide, or protein, wherein the number of moles of acylating agent used for each mole of the amino acid, peptide, or protein is in the range of 1.0-3.0.
175. The method of embodiment 174, wherein the number of moles of acylating agent used for each mole of the amino acid, peptide, or protein is in the range of 1.0-2.0.
176. The method of any of embodiments 174-175, wherein the number of moles of acylating agent used for each mole of the amino acid, peptide, or protein is in the range of 1.0-1.5.
177. The method of any of embodiments 174-176, wherein the number of moles of acylating agent used for each mole of the amino acid, peptide, or protein is in the range of 1.0-1.2.
178. The method of any of embodiments 174-177, wherein the number of moles of acylating agent used for each mole of the amino acid, peptide, or protein is in the range of 1.0-1.1.
179. The method of any of embodiments 121-170, which is for acylating two amino groups in the amino acid, peptide, or protein, wherein the number of moles of acylating agent used for each mole of the amino acid, peptide, or protein is in the range of 2.0-5.0.
180. The method of embodiment 179, wherein the number of moles of acylating agent used for each mole of the amino acid, peptide, or protein is in the range of 2.0-4.0.
181. The method of any of embodiments 179-180, wherein the number of moles of acylating agent used for each mole of the amino acid, peptide, or protein is in the range of 2.0-3.5.
182. The method of any of embodiments 179-181, wherein the number of moles of acylating agent used for each mole of the amino acid, peptide, or protein is in the range of 2.0-3.0.
183. The method of any of embodiments 179-182, wherein the number of moles of acylating agent used for each mole of the amino acid, peptide, or protein is in the range of 2.0-2.6.
184. The method of any of embodiments 121-170, which is for acylating three amino groups in the amino acid, peptide, or protein, wherein the number of moles of acylating agent used for each mole of the amino acid, peptide, or protein is in the range of 3.0-10.0.
185. The method of embodiment 184, wherein the number of moles of acylating agent used for each mole of the amino acid, peptide, or protein is in the range of 3.0-7.5.
186. The method of any of embodiments 184-185, wherein the number of moles of acylating agent used for each mole of the amino acid, peptide, or protein is in the range of 3.0-5.0.
187. The method of any of embodiments 184-186, wherein the number of moles of acylating agent used for each mole of the amino acid, peptide, or protein is in the range of 3.0-4.0.
188. The method of any of embodiments 168-187, wherein the number of moles of acylating agent used for each mole of the amino acid, peptide, or protein is referred to as Eq. SC.
189. The method of embodiment 188, wherein Eq. SC is the inverse of the molar ratio of the amino acid, peptide, or protein and the acylating agent ((moles of amino acid, peptide, or protein):(moles of acylating agent)).
190. The method of any of embodiments 121-189, which comprises a step, prior to the acylation reaction step, of dissolving the amino acid, peptide, or protein in an aqueous solution.
191. The method of embodiment 190, wherein the amino acid, peptide, or protein is dissolved at a temperature of −10 (minus 10) to 30° C.
192. The method of any of embodiments 190-191, wherein the amino acid, peptide, or protein is dissolved at a temperature of about 5° C.
193. The method of any of embodiments 190-191, wherein the amino acid, peptide, or protein is dissolved at a temperature of about RT (room temperature).
194. The method of any of embodiments 190-193, wherein the pH of the solution of the amino acid, peptide, or protein is adjusted to a desired level.
195. The method of embodiment 194, wherein the desired level is in the range of pH 8-12.
196. The method of any of embodiments 194-195, wherein the desired level is in the range of pH 9-12.
197. The method of any of embodiments 194-196, wherein an alkalimetal hydroxide, an alkali carbonate, and/or a tertiary amine base is used for the pH adjustment.
198. The method of any of embodiments 190-197, wherein the solution of the amino acid, peptide, or protein comprises the amino acid, peptide, or protein in a concentration of at least 5.0 mg/mL.
199. The method of embodiment 198, wherein the concentration is in the range of 5.0-500 mg/mL.
200. The method of any of embodiments 198-199, wherein the concentration is in the range of 5.0-250 mg/mL.
201. The method of any of embodiments 198-200, wherein the concentration is in the range of 5.0-150 mg/mL.
202. The method of any of embodiments 198-201, wherein the concentration is in the range of 5.0-100 mg/mL.
203. The method of any of embodiments 198-202, wherein the concentration is in the range of 10-60 mg/mL.
204. The method of any of embodiments 198-203, wherein the concentration is in the range of 15-45 mg/mL.
205. The method of any of embodiments 198-201, wherein the concentration is in the range of 10-250 mg/mL.
206. The method of any of embodiments 198-201 and 205, wherein the concentration is in the range of 20-150 mg/mL.
206a. The method of any of embodiments 198-201 and 206, wherein the concentration is in the range of 50-150 mg/mL.

207. The method of any of embodiments 198-201 and 205-206, wherein the concentration is in the range of 25-125 mg/mL.
208. The method of any of embodiments 121-207, wherein the product of the acylation reaction has a purity of at least 50%, wherein the purity is determined after UPLC or HPLC analysis and using UV at 210 nm as the area under the curve (AUC) for the peak that represents the desired product relative to the combined areas under the curve (AUC's) for the peaks representing other products of the reaction.
209. The method of embodiment 208, wherein the purity is at least 55%.
210. The method of any of embodiments 208-209, wherein the purity is at least 60%.
211. The method of any of embodiments 208-210, wherein the purity is at least 65%.
212. The method of any of embodiments 208-211, wherein the relevant product is the desired product.
213. The method of any of embodiments 208-212, wherein the UPLC and/or HPLC analysis is substantially as described in the experimental part (A2. General Methods of Detection, Analysis and Characterisation, part 2).
214. The method of embodiment 213, wherein the UPLC method is method UPLC_A_1.
215. The method of embodiment 213, wherein the HPLC method is method HPLC_A_1.
216. The method of embodiment 213, wherein the UPLC method is method UPLC_A_3.
217. The method of any of embodiments 208-216, wherein the desired product is a mono-acylated GLP-1 peptide.
218. The method of embodiment 217, wherein the other products of the reaction consist of the non-acylated peptide and di-acylated variants thereof.
219. The method of any of embodiments 217-218, wherein the purity is at least 70%.
220. The method of any of embodiments 217-219, wherein the purity is at least 75%.
221. The method of any of embodiments 217-220, wherein the purity is at least 80%.
222. The method of any of embodiments 217-221, wherein the purity is at least 85%.
223. The method of any of embodiments 217-222, wherein the purity is at least 90%.
224. The method of any of embodiments 217-223, wherein the purity is at least 93%.
225. The method of any of embodiments 217-224, wherein the purity is at least 95%.
226. The method of any of embodiments 217-225, wherein the purity is at least 96%.
227. The method of any of embodiments 217-226, wherein the purity is at least 97%.
228. The method of any of embodiments 217-227, wherein the purity is at least 98% %.
229. The method of any of embodiments 208-216, wherein the desired product is a di-acylated GLP-1 peptide.
230. The method of embodiment 217, wherein the other products of the reaction consist of the non-acylated peptide, mono-acylated peptide, and other by-products, if any.
231. The method of any of embodiments 229-230, wherein the purity is at least 70%.
232. The method of any of embodiments 229-231, wherein the purity is at least 75%.
233. The method of any of embodiments 229-232, wherein the purity is at least 80%.
234. The method of any of embodiments 229-233, wherein the purity is at least 85%.
235. The method of any of embodiments 229-234, wherein the purity is at least 90%.
236. The method of any of embodiments 229-235, wherein the purity is at least 93%.
237. The method of any of embodiments 229-236, wherein the purity is at least 95%.
238. The method of any of embodiments 229-237, wherein the purity is at least 96%.
239. The method of any of embodiments 229-238, wherein the purity is at least 97%.
240. The method of any of embodiments 229-239, wherein the purity is at least 98%.
241. The method of any of embodiments 208-216, wherein the desired product is a mono acylated insulin peptide.
242. The method of embodiment 217, wherein the other products of the reaction consist of the non-acylated peptide and di-acylated variants thereof.
243. The method of any of embodiments 241-242, wherein the purity is at least 70%.
244. The method of any of embodiments 241-243, wherein the purity is at least 75%.
245. The method of any of embodiments 241-244, wherein the purity is at least 80%.
246. The method of any of embodiments 241-245, wherein the purity is at least 85%.
247. The method of any of embodiments 241-246, wherein the purity is at least 90%.
248. The method of any of embodiments 241-247, wherein the purity is at least 93%.
249. The method of any of embodiments 241-248, wherein the purity is at least 95%.
250. The method of any of embodiments 241-249, wherein the purity is at least 96%.
251. The method of any of embodiments 241-250, wherein the purity is at least 97%.
252. The method of any of embodiments 241-251, wherein the purity is at least 98%.
253. The method of any of embodiments 121-252, which comprises a further step of purifying the desired product of the acylation reaction.
254. The method of embodiment 253, wherein the desired product of the acylation reaction is the amino acid, peptide, or protein in which an amino group is acylated.
255. The method of embodiment 254, wherein the desired product is the amino acid, peptide, or protein in which an amino group of the amino acid, peptide, or protein has a side chain attached to it, via an amide bond, wherein the side chain comprises Formula H:

$$(P-L)_U\text{-BL-B,} \qquad \text{Formula Ic:}$$

wherein P, L, U, BL, and B are as defined in any of embodiments 7-88, and the attachment of the side chain is at B.

256. The method of any of embodiments 253-255, wherein one or more amino groups are acylated.
257. The method of any of embodiments 253-256, wherein up to five amino groups are acylated.
258. The method of any of embodiments 253-257, wherein one, two, or three amino groups are acylated.
259. The method of any of embodiments 253-258, wherein one or two amino groups are acylated.

260. The method of any of embodiments 253-259, wherein one amino group is acylated.
261. The method of any of embodiments 253-260, wherein two amino groups are acylated.
262. The method of any of embodiments 253-261, wherein the/each amino group being acylated is the epsilon amino group of a Lys residue of the amino acid, peptide, or protein.
263. The method of any of embodiments 106-262, wherein the amino acid, peptide, or protein is a pharmaceutical peptide or protein.
264. The method of embodiment 263, wherein the pharmaceutical peptide or protein is suitable for the treatment of diabetes or obesity.
265. The method of any of embodiments 263-264, wherein the pharmaceutical peptide or protein is selected from GLP-1, insulin, pYY, amylin, and analogues thereof.
266. The method of any of embodiments 106-265, wherein the peptide or protein is a GLP-1 peptide.
267. The method of embodiment 266, wherein the GLP-1 peptide is native human GLP-1(7-37) (SEQ ID NO: 1) or an analogue thereof (a GLP-1 analogue).
268. The method of embodiment 266, wherein the analogue has a maximum of 10 amino acid changes as compared to GLP-1(7-37) (SEQ ID NO: 1).
269. The method of embodiment 267, wherein the analogue has a maximum of 9 amino acid changes as compared to GLP-1(7-37) (SEQ ID NO: 1).
270. The method of embodiment 267, wherein the analogue has a maximum of 8 amino acid changes as compared to GLP-1(7-37) (SEQ ID NO: 1).
271. The method of embodiment 267, wherein the analogue has a maximum of 7 amino acid changes as compared to GLP-1(7-37) (SEQ ID NO: 1).
272. The method of embodiment 267, wherein the analogue has a maximum of 6 amino acid changes as compared to GLP-1(7-37) (SEQ ID NO: 1).
273. The method of embodiment 267, wherein the analogue has a maximum of 5 amino acid changes as compared to GLP-1(7-37) (SEQ ID NO: 1).
274. The method of embodiment 267, wherein the analogue has a maximum of 4 amino acid changes as compared to GLP-1(7-37) (SEQ ID NO: 1).
275. The method of embodiment 267, wherein the analogue has a maximum of 3 amino acid changes as compared to GLP-1(7-37) (SEQ ID NO: 1).
276. The method of embodiment 267, wherein the analogue has a maximum of 2 amino acid changes as compared to GLP-1(7-37) (SEQ ID NO: 1).
277. The method of embodiment 267, wherein the analogue has a maximum of 1 amino acid change as compared to GLP-1(7-37) (SEQ ID NO: 1).
278. The method of any of embodiments 266-277, wherein the GLP-1 analogue comprises an amino acid sequence of Formula III:

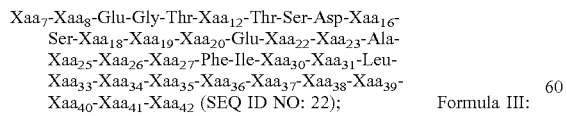

wherein $Xaa_7$ is L-histidine, (S)-2-Hydroxy-3-(1H-imidazol-4-yl)-propionic acid, D-histidine, deamino-histidine, homo-histidine, $N^\alpha$-acetyl-histidine, $N^\alpha$-formyl-histidine, $N^\alpha$-methyl-histidine, 3-pyridylalanine, 2-pyridylalanine, or 4-pyridylalanine;

$Xaa_8$ is Ala, Gly, Ser, Aib, (1-aminocyclopropyl) carboxylic acid, or (1-aminocyclobutyl) carboxylic acid;
$Xaa_{12}$ is Phe or Leu;
$Xaa_{16}$ is Val or Leu;
$Xaa_{18}$ is Ser, Val, Arg, or Leu;
$Xaa_{19}$ is Tyr or Gln;
$Xaa_{20}$ is Leu, Lys, or Met;
$Xaa_{22}$ is Gly or Glu;
$Xaa_{23}$ is Gln, Glu, or Arg;
$Xaa_{25}$ is Ala or Val;
$Xaa_{26}$ is Lys or Arg;
$Xaa_{27}$ is Glu, Lys, or Leu;
$Xaa_{30}$ is Ala, Glu, or Arg;
$Xaa_{31}$ is Trp or His;
$Xaa_{33}$ is Val;
$Xaa_{34}$ is Arg, His, Asn, Gly, or Gln;
$Xaa_{35}$ is Gly, Ala, or absent;
$Xaa_{36}$ is Arg, Lys, Gly, or absent;
$Xaa_{37}$ is Gly, Pro, Lys, or absent;
$Xaa_{38}$ is Ser, Gly, Ala, Glu, Pro, Lys, or absent;
$Xaa_{39}$ is Ser, Gly, Ala, Glu, Pro, or absent;
$Xaa_{40}$ is Ser, Gly, Ala, Glu, Pro, or absent;
$Xaa_{41}$ is Ser, Gly, Ala, Glu, Pro, or absent; and
$Xaa_{42}$ is Lys or absent;

wherein at least one of $Xaa_{20}$, $Xaa_{26}$, $Xaa_{27}$, $Xaa_{36}$, $Xaa_{37}$, $Xaa_{38}$, and $Xaa_{42}$ is Lys; with the proviso that if one of $Xaa_{35}$, $Xaa_{36}$, $Xaa_{37}$, $Xaa_{38}$, $Xaa_{39}$, $Xaa_{40}$, or $Xaa_{41}$ is absent, then each of the subsequent amino acids is also absent;

or a pharmaceutically acceptable salt, amide, or ester thereof.

279. The method of embodiment 278, wherein
$Xaa_7$ is L-histidine; $Xaa_8$ is Aib; $Xaa_{12}$ is Phe; $Xaa_{16}$ is Val; $Xaa_{18}$ is Ser; $Xaa_{19}$ is Tyr; $Xaa_{20}$ is Leu or Lys; $Xaa_{22}$ is Gly or Glu; $Xaa_{23}$ is Gln; $Xaa_{25}$ is Ala; $Xaa_{26}$ is Lys or Arg; $Xaa_{27}$ is Glu or Lys; $Xaa_{30}$ is Ala or Glu; $Xaa_{31}$ is Trp; $Xaa_{33}$ is Val; $Xaa_{34}$ is Arg or Gly; $Xaa_{35}$ is Gly or absent; $Xaa_{36}$ is Arg, Lys, or absent; $Xaa_{37}$ is Gly, Lys, or absent; $Xaa_{38}$ is Glu, Lys, or absent; $Xaa_{39}$ is Ser, Gly, or absent; $Xaa_{40}$ is Gly, Pro, or absent; $Xaa_{41}$ is Ser, Glu, or absent; and $Xaa_{42}$ is Lys or absent.

280. The method of any of embodiments 278-279, wherein up to five of $Xaa_{20}$, $Xaa_{26}$, $Xaa_{27}$, $Xaa_{36}$, $Xaa_{37}$, $Xaa_{38}$, and $Xaa_{42}$ is/are Lys.
281. The method of any of embodiments 278-280, wherein one, two, or three of $Xaa_{20}$, $Xaa_{26}$, $Xaa_{27}$, $Xaa_{36}$, $Xaa_{37}$, $Xaa_{38}$, and $Xaa_{42}$ is/are Lys.
282. The method of any of embodiments 278-281, wherein one or two of $Xaa_{20}$, $Xaa_{26}$, $Xaa_{27}$, $Xaa_{36}$, $Xaa_{37}$, $Xaa_{38}$, and $Xaa_{42}$ is/are Lys.
283. The method of any of embodiments 278-282, wherein one of $Xaa_{20}$, $Xaa_{26}$, $Xaa_{27}$, $Xaa_{36}$, $Xaa_{37}$, $Xaa_{38}$, and $Xaa_{42}$ is Lys.
284. The method of any of embodiments 278-282, wherein two of $Xaa_{20}$, $Xaa_{26}$, $Xaa_{27}$, $Xaa_{36}$, $Xaa_{37}$, $Xaa_{38}$, and $Xaa_{42}$ is Lys.
285. The method of any of embodiments 278-284, wherein
(i) $Xaa_{38}$ and $Xaa_{42}$ are Lys,
(ii) $Xaa_{26}$ is Lys,
(iii) $Xaa_{27}$ and $Xaa_{36}$ are Lys,
(iv) $Xaa_{20}$ and $Xaa_{27}$ are Lys,
(v) $Xaa_{26}$ and $Xaa_{37}$ are Lys, or
(vi) $Xaa_{37}$ is Lys.
285a. The method of embodiment 285, wherein acylation takes place at the indicated Lys residue(s).

286. The method of any of embodiments 278-285a, wherein the GLP-1 analogue has the amino acid sequence of Formula III.
287. The method of any of embodiments 278-286, wherein the GLP-1 analogue is selected from SEQ ID NO: 2, SEQ ID NO: 4, SEQ ID NO: 6, SEQ ID NO: 12, SEQ ID NO: 14, SEQ ID NO: 16, and SEQ ID NO: 18; or a pharmaceutically acceptable salt, amide, or ester thereof.
288. The method of any of embodiments 106-265, wherein the peptide or protein is an N-terminally truncated GLP-1 peptide (referred to as precursor).
289. The method of embodiment 288, wherein in said precursor the two amino acids corresponding to the amino acid residues at position 7 and 8 of GLP-1(7-37) (SEQ ID NO: 1) have been deleted.
290. The method of any of embodiments 288-289, wherein in all other respects (other than the N-terminal truncation), the precursor is as defined in any of embodiments 268-287.
291. The method of any of embodiments 288-290, wherein the precursor comprises Formula IIIa:

Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$ (SEQ ID NO: 23),  Formula IIIa:

wherein each amino acid residue is as defined in any of embodiments 278-287; or a pharmaceutically acceptable salt, amide, or ester thereof.
292. The method of any of embodiments 288-291, wherein the precursor has the amino acid sequence of Formula IIIa; or a pharmaceutically acceptable salt, amide, or ester thereof.
293. The method of any of embodiments 288-292, wherein the precursor is selected from SEQ ID NO: 3, SEQ ID NO: 5, SEQ ID NO: 7, SEQ ID NO: 13, SEQ ID NO: 15, SEQ ID NO: 17, and SEQ ID NO: 19; or a pharmaceutically acceptable salt, amide, or ester thereof.
294. The method of any of embodiments 288-293, wherein the precursor is prepared by recombinant expression.
295. The method of any of embodiments 288-294, which comprises a further step of purifying the acylated precursor, product of the acylation reaction.
296. The method of embodiment 295, wherein the acylated precursor is as defined in any of embodiments 254-262.
297. The method of any of embodiments 121-265 and 288-296, which comprises a step (referred to as ligation) of reacting the acylated precursor with a protected di-peptide of Chem. 8:

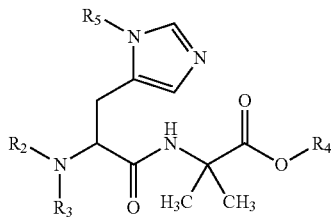

Chem. 8 wherein
R$_2$ is H or an amino protecting group, and R$_3$ is an amino protecting group; or
R$_2$ is a removable alkyl group, and R$_3$ is H or a removable alkyl group; or R$_2$ and R$_3$ are jointly forming a ring;
R$_4$ is H, or a secondary ammonium cation, a tertiary ammonium cation or a metal cation forming a salt with the carboxylate group; and
R$_5$ is absent or an acidic salt, resulting in the corresponding acylated full-length peptide or protein with protection groups at the N-terminus of the peptide or protein.
298. The method of embodiment 297, wherein the ligation step is conducted under suitable conditions.
299. The method of any of embodiments 297-298, which comprises a further step of removing the protecting groups R$_1$ and/or R$_2$ (referred to as de-protection).
300. The method of embodiment 299, wherein the de-protection step is conducted under suitable conditions.
301. The method of any of embodiments 297-300, which comprises a further step of purifying the de-protected acylated full-length peptide or protein.
302. The method of any of embodiments 266-287 and embodiment 301, wherein the acylated peptide or protein is a GLP-1 receptor agonist.
303. The method of any of embodiments 106-265, wherein the peptide or protein is an insulin peptide.
304. The method of embodiment 303, wherein the insulin peptide is human insulin, human proinsulin, human pre-proinsulin, and analogues thereof.
305. The method of any of embodiments 303-304, wherein the analogue has a maximum of 10 amino acid changes as compared to human insulin.
306. The method of any of embodiments 303-305, wherein the analogue has a maximum of 9 amino acid changes as compared to human insulin.
307. The method of any of embodiments 303-306, wherein the analogue has a maximum of 8 amino acid changes as compared to human insulin.
308. The method of any of embodiments 303-307, wherein the analogue has a maximum of 7 amino acid changes as compared to human insulin.
309. The method of any of embodiments 303-308, wherein the analogue has a maximum of 6 amino acid changes as compared to human insulin.
310. The method of any of embodiments 303-309, wherein the analogue has a maximum of 5 amino acid changes as compared to human insulin.
311. The method of any of embodiments 303-310, wherein the analogue has a maximum of 4 amino acid changes as compared to human insulin.
312. The method of any of embodiments 303-311, wherein the analogue has a maximum of 3 amino acid changes as compared to human insulin.
313. The method of any of embodiments 303-312, wherein the analogue has a maximum of 2 amino acid changes as compared to human insulin.
314. The method of any of embodiments 303-313, wherein the analogue has a maximum of 1 amino acid change as compared to human insulin.
315. The method of any of embodiments 303-314, wherein the analogue has a maximum of 10 amino acid changes as compared to human proinsulin.
316. The method of any of embodiments 303-315, wherein the analogue has a maximum of 9 amino acid changes as compared to human proinsulin.

317. The method of any of embodiments 303-316, wherein the analogue has a maximum of 8 amino acid changes as compared to human proinsulin.

318. The method of any of embodiments 303-317, wherein the analogue has a maximum of 7 amino acid changes as compared to human proinsulin.

319. The method of any of embodiments 303-318, wherein the analogue has a maximum of 6 amino acid changes as compared to human proinsulin.

320. The method of any of embodiments 303-319, wherein the analogue has a maximum of 5 amino acid changes as compared to human proinsulin.

321. The method of any of embodiments 303-320, wherein the analogue has a maximum of 4 amino acid changes as compared to human proinsulin.

322. The method of any of embodiments 303-321, wherein the analogue has a maximum of 3 amino acid changes as compared to human proinsulin.

323. The method of any of embodiments 303-322, wherein the analogue has a maximum of 2 amino acid changes as compared to human proinsulin.

324. The method of any of embodiments 303-323, wherein the analogue has a maximum of 1 amino acid change as compared to human proinsulin.

325. The method of any of embodiments 303-324, wherein the analogue comprises at least one of the following amino acid changes: A14E, B16H, B25H, desB27, and/or desB30.

326. The method of any of embodiments 303-325, wherein the analogue comprises the amino acid change A14E.

327. The method of any of embodiments 303-326, wherein the analogue comprises the amino acid change B16H.

328. The method of any of embodiments 303-327, wherein the analogue comprises the amino acid change B25H.

329. The method of any of embodiments 303-328, wherein the analogue comprises the amino acid change desB27.

330. The method of any of embodiments 303-329, wherein the analogue comprises the amino acid change desB30.

331. The method of any of embodiments 303-330, wherein the analogue is selected from the following:
i) A14E, B25H, desB27, desB30 human insulin (SEQ ID NOs: 8 and 9);
ii) A14E, B25H, desB30 human insulin (SEQ ID NOs: 10 and 11); and
iii) A14E, B16H, B25H, desB30 human insulin (SEQ ID NOs: 20 and 21); or a pharmaceutically acceptable salt, amide, or ester thereof.

332. The method of any of embodiments 303-331, wherein the analogue is A14E, B25H, desB27, desB30 human insulin (SEQ ID NOs: 8 and 9); or a pharmaceutically acceptable salt, amide, or ester thereof.

333. The method of any of embodiments 303-331, wherein the analogue is A14E, B25H, desB30 human insulin (SEQ ID NOs: 10 and 11); or a pharmaceutically acceptable salt, amide, or ester thereof.

334. The method of any of embodiments 303-331, wherein the analogue is A14E, B16H, B25H, desB30 human insulin (SEQ ID NOs: 20 and 21); or a pharmaceutically acceptable salt, amide, or ester thereof.

335. The method of any of embodiments 303-334, wherein the insulin peptide is acylated at B29K.

336. The method of any of embodiments 303-335, wherein the insulin peptide is an analogue of human insulin.

337. The method of any of embodiments 303-335, wherein the insulin peptide is an analogue of human proinsulin.

338. The method of embodiment 337, wherein the analogue of human proinsulin is prepared as a precursor by recombinant expression.

339. The method of any of embodiments 337-3388, wherein the C-peptide is cleaved off.

340. The method of embodiment 339, wherein the cleavage is enzymatic.

341. The method of any of embodiments 303-340, which comprises a further step of purifying the acylated insulin peptide.

342. The method of any of embodiments 303-341, wherein the acylated insulin peptide (excluding acylated proinsulin, pre-proinsulin, and analogues thereof) has insulin receptor affinity.

342a. The method of embodiment 342, wherein the affinity is determined using the assay of Example 178 of WO 2009/115469 at 0% HSA.

342b. The method of embodiment 342a, wherein the affinity is at least 0.10%.

343. The method of any of embodiments 106-265, wherein the peptide or protein is a pYY receptor agonist.

344. The method of embodiment 343, wherein the pYY receptor agonist is native human pYY or an analogue thereof (a pYY analogue).

345. The method of any of embodiments 106-265, wherein the peptide or protein is an amylin receptor agonist.

346. The method of embodiment 345, wherein the amylin receptor agonist is native human amylin or an analogue thereof (an amylin analogue).

347. The method of any of embodiments 121-346, which further comprises a step of removing a secretory signal sequence from the peptide or protein.

348. The method of any of embodiments 121-347, wherein the N-terminal amino acid residue of the peptide or protein is an acidic amino acid residue.

348a. The method of embodiment 348, wherein the N-terminal amino acid residue is Glu.

349. The method of any of embodiments 253-342, wherein the desired product of the acylation reaction is selected from the following compounds, all specifically incorporated herein by reference:

(i) Example 3 of WO 2015/000942, structure Chem. 41,
(ii) Example 11 of WO 2015/000942, structure Chem. 42,
(iii) Example 4 of WO 2006/097537, structure Chem. 43, preferably Chem. 43a

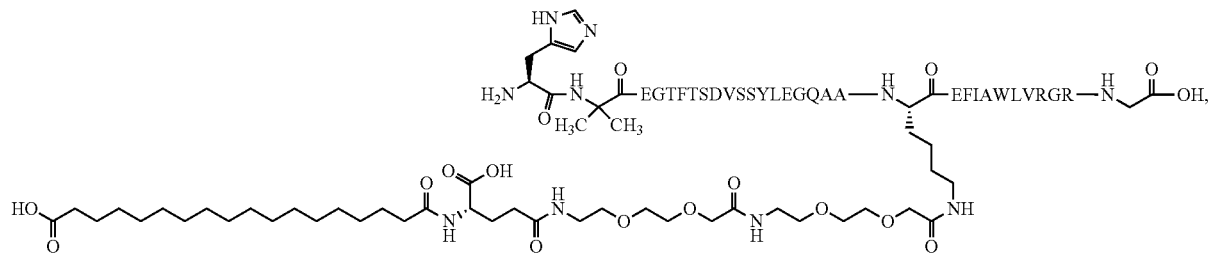

Chem. 43a (SEQ ID NO: 24)

(iv) Example 31 of WO 2012/140117, structure Chem. 44,
(v) Example 5 of WO 2012/140117, structure Chem. 45,
(vi) Example 2 of WO 2011/080103, structure Chem. 46,
(vii) Example 14 of WO 2016/097108, structure Chem. 47,
(iix) Example 1 of WO 2016/097108, structure Chem. 48,
(ix) Example 11 of WO 2016/083499, structure Chem. 49,
(x) Example 12 of WO 2016/083499, structure Chem. 50,
(xi)-(xx) the precursor molecules corresponding to each of (i)-(x), respectively, in which the two N-terminal amino acids have been deleted,
(xxi) Example 57 of WO 2009/115469, structure Chem. 51,
(xxii) Example 9 of WO 2009/115469, structure Chem. 52,
(xxiii) Example 33 of WO 2009/115469, structure Chem. 53, and
(xxiv) Example 1 of WO 2015/052088, structure Chem. 54;
or a pharmaceutically acceptable salt, amide, or ester thereof.

350. A compound selected from each of the compounds (xi)-(xii) and (xiv)-(xx) of embodiment 349, SEQ ID NO: 3, SEQ ID NO: 5, SEQ ID NO: 13, SEQ ID NO: 15, SEQ ID NO: 17, and SEQ ID NO: 19; or a pharmaceutically acceptable salt, amide, or ester thereof.

351. A compound which comprises Chem. 7b:

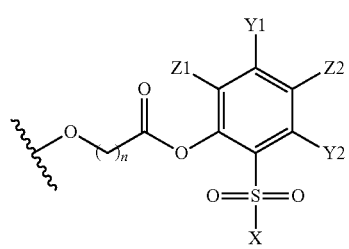

Chem. 7b wherein
n is an integer in the range of 1-2,
—Z1 and —Z2 independently are selected from the group consisting of —Cl, —F, —Br, —NO₂, —CN, —SO₂X2, —CONH, and —CF₃, wherein X2 is selected from the group consisting of —OH, CH₃, —CF₃, and —N(R¹R²) (e.g. —N(CH₃)₂),
—Y1 and —Y2 independently are absent or selected from the group consisting of —Cl and —F,
—X and X2 independently are selected from the group consisting of —OH, CH₃, —CF₃, and —N(R¹R²) (e.g. —N(CH₃)₂), wherein $R^1$ and $R^2$ independently are selected from the group consisting of H and C1-C5 alkyl, wherein C1-C5 alkyl may be linear, branched or cyclic and optionally substituted with a hydrophilic moiety (such as —OH or —COOH);
or a salt thereof.

352. The compound according to the preceding embodiment wherein said compound comprises Chem. 7a:

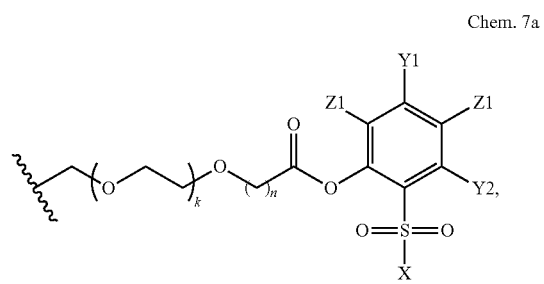

Chem. 7a wherein k is an integer in the range of 1-10, and the remaining substituents are as defined in the preceding embodiments.

353. The compound according to any one of embodiments 351-352 wherein —Z1 and/or —Z2 are —Cl.
354. The compound according to any one of embodiments 351-353 wherein —Z1 and —Z2 are —Cl.
355. The compound according to any one of embodiments 351-354 wherein —Z2 is not —NO₂ or —SO₂X2.
356. The compound according to any one of embodiments 351-355 wherein —X and/X2 are —OH or —N(CH₃)₂.
357. The compound according to any one of embodiments 351-356 wherein Y1 and/or Y2 are absent.
358. The compound according to any one of embodiments 351-357 wherein Y1 and Y2 are absent.
359. The method according to any one of embodiments 90-349 wherein Chem. 1a is replaced with Chem. 1c.
360. The method according to any one of embodiments 90-349 or 359 wherein Chem. 6a is replaced with Chem. 6b or Chem. 6c.
361. The method according to any one of embodiments 90-349 or 359-360 wherein Chem. 7 is replaced with Chem. 7a or Chem. 7b, such as 7a or Chem. 7b as defined in any one of embodiments 351-358.

Examples

This experimental part starts with a list of abbreviations, and is followed by a section including general methods for synthesising and characterising peptide analogues and derivatives of the invention. Then follows a number of examples which relate to the preparation of specific activated side chains, and at the end a number of examples have been included relating to the properties of these activated side chains and their use in acylating peptide or protein analogues to produce desired derivatives thereof. The examples serve to illustrate the invention.

Abbreviations Used

The following abbreviations are used in the rest of this experimental part.
AcOH: Acetic acid
Ado: 8-Amino-3,6-dioxaoctanoic acid
Backbone: Peptide or peptide analogue (GLP-1, insulin)
Boc: tert Butyloxycarbonyl
Bn: Benzyl
Bz: Benzoyl
$CH_3CN$: Acetonitrile
DCC: N,N'-Dicyclohexylcarbodiimide
DCM: Dichloromethane
DIC: Diisopropylcarbodiimide
DIPEA: Diisopropylethylamine
DMAP: 4-Dimethylaminopyridine
DMF: N,N-Dimethylformamide
EDC: 1-Ethyl-3-(3-dimethylaminopropyl)carbodiimide
EtOAc: Ethylacetate
$Et_2O$: Diethylether
Eq: Equivalent
Fmoc: 9H-fluoren-9-ylmethoxycarbonyl
HFIP: Hexafluoroisopropanol
$H_2O$: Water
HOBt: 1-Hydroxybenzotriazole
i-PrOH Isopropanol
MeOH Methanol
MeTHF Methyl tetrahydrofurane
$MgSO_4$: Magnesium Sulphate
MW: Molecular weight
NaOH: Sodium hydroxide
NHS: N-Hydroxysuccinimide
NMP: 1-Methyl-pyrrolidin-2-one
OEG: Oligo Ethylene Glycol, alternative name to Ado, see above
OtBu: tert Butyl ester
Oxyma Pure®: Cyano-hydroxyimino-acetic acid ethyl ester
RT: Room temperature
OSu: N-Hydroxysuccinimide ester
Pd/C: Palladium on carbon
Pt/C: Platinum on carbon
PTFE: Polytetrafluoroethylene
qNMR: Quantitative nuclear magnetic resonance
SC: Side chain
tBu: tert-Butyl
TEA: Triethylamine
TFA: Trifluoroacetic acid
THF: Tetrahydrofurane
TIPS: Triisopropylsilane
Trx: Tranexamic acid (trans-4-(aminomethyl)cyclohexanecarboxylic acid)
Vol: Volume A. Materials and General Methods for Preparation, Detection and Characterisation This section relates to methods for solid phase peptide synthesis (SPPS methods, including methods for de-protection of amino acids, methods for cleaving the peptide from resin, and for its purification), as well as methods for detecting and characterising the resulting side chains (LCMS and UPLC methods and NMR). $^1H$ and $^{13}C$ NMR spectra were recorded at 400 MHz and 100 MHz, respectively, on a Bruker Aeon 400 instrument. For qNMR 1,3-benzodioxole was used as the standard reference. Chemical shifts are reported in ppm on the δ scale relatively to the chemical shift of the deuterated solvent. Kaiser-test (presence of free amines in SPPS) and Chloranil-test (test of piperidine in NMP) was performed according to "Fmoc solid phase peptide synthesis a practical approach" Edited by W. C. Chan and P. D. White, Oxford 2000 (2004), University Press page 61-62.

A1. Methods of Preparation and Modification

1. Synthesis of Protected Side Chain

The resin bound protected side chains were prepared on a 2-chlorotritylchloride resin using standard Fmoc chemistry. The first Fmoc protected amino carboxylic acid (2 eq) (linker element) was dissolved in DCM and added to a DCM washed and drained resin. A tertiary amine base such as DIPEA or TEA (4 Eq) was added and the resin mixture was agitated for a period of time between 12 and 17 hours at RT. The resin was allowed to react with MeOH (0.79 mL/g resin) to cap free chloride sites at RT for 1 hour. The resin was drained and flow washed three times with NMP or DMF (about 5.2 mL/g resin). Fmoc deprotection was achieved using piperidine in NMP preferably 20% piperidine (1.05 mL/g resin) in NMP (4.15 mL/g resin), at RT for 15 to 45 min, typically 30 min, before the resin was washed thoroughly with NMP or DMF. The step was repeated until complete deprotection was obtained, typically two times or more. The resin was drained and flow washed three times or more with NMP or DMF (ca 5.2 mL/g resin) until the Chloranil test gave a negative result.

Coupling of the sequential Fmoc protected amino carboxylic acids (linker) and the final mono-protected carboxylic diacid (such as 18-benzyloxy-18-oxo-octadecanoic acid) or phenoxy carboxylic diacid (such as 10-(4-benzyloxycarbonylphenoxy)decanoic acid), (protractor) was achieved using conventional coupling conditions as described below.

To a solution of Fmoc protected amino carboxylic acid (2-3 eq.) in a solvent like NMP or DMF and Oxyma Pure® (2-3 eq.) was added DIC (2-3 eq). The mixture was agitated for 15 to 60 min before the mixture was added to the resin. The mixture was agitated at RT for 1 to 18 hours, typically 17 hours. Alternatively, if the coupling was not completed judged by the Kaiser test, the step was repeated until a negative test was achieved.

After synthesis, the resin was washed by DCM and the protected side chain was cleaved off from the resin by treatment with 1% TFA in DCM for 1-3 hours. The cleavage solution was evaporated under vacuum to dryness, and the crude material was used without further purification in the activation step described in the next section.

2. Activation of Protected Side Chain

Activation of the protected side chain obtained from the procedure 1 was made using standard conditions known in the art.

NHS esters were made by one of following procedures: The carboxylic acid (protected side chain from procedure 1) was dissolved in an appropriate solvent such as DCM. NHS and EDC were added to the solution together with a tertiary amine base such as DIPEA or TEA. The mixture was stirred at RT until the reaction was complete, typically from 3 to 16 hours. Alternatively the carboxylic acid was dissolved together with NHS and treated with DIC. The organic phase was washed with a 1:1 mixture of 0.5 M HCl (aq) and saturated NaCl. After separation of the phases, the organic phase was dried over MgSO$_4$. Filtration and evaporation of the solvent yielded a crude material which was used directly in the next step.

Phenolic esters (such as esters of 2,4-DC-phenol and 2,6-DC-phenol) were made by the following procedure: The carboxylic acid (protected side chain from procedure 1) was dissolved in an appropriate solvent such as THF, DCM, NMP or DMF. The relevant substituted phenol derivative, DMAP and EDC were added to the solution. The mixture was stirred at RT until the reaction was complete, typically from 2 to 16 hours. The product mixture was subjected to the same work up procedure described for the NHS case with one difference. After separation of the phases, the organic phase was washed with a 1:1 mixture of 5% (vol/vol) NaHCO$_3$ (aq) and saturated NaCl followed by another wash with a 1:1 mixture of 10% (vol/vol) NaHSO$_4$ and saturated NaCl. The organic phase was dried over MgSO$_4$, filtered and the solvent was removed in vacuo. The crude material was used directly in the next step.

3. Methods for Removal of tBu or Bn Protection Groups

Deprotection of the tBu or Bn esters was achieved using standard procedures described in the literature (Greene's Protective Group in Organic Synthesis, 4$^{th}$ addition, ISBN-13:978-0471697541).

Method: Mod_Bz_1

Benzyl ester deprotection was made by the following procedure; the activated side chain from previous procedure 2, was dissolved in a suitable solvent such as THF, EtOAc, acetone, i-PrOH, AcOH, NMP, DMF, or HFIP. A heterogeneous catalyst such as Pd/C or Pt/C was added, and the resulting mixture was stirred under an atmosphere of hydrogen gas until the reaction was complete. Reaction time was typically one to 16 hours. The reaction mixture was filtered to remove the catalyst and the activated side chain was isolated by precipitation in appropriate solvent such as diethyl ether, MeTHF, EtOAc, or heptane. An alternative isolation procedure was to extract the product from a 1:1 mixture of EtOAc and water. After separation of the phases, the organic phase was dried over MgSO$_4$, filtered and the solvent was evaporated under reduced pressure to yield crude material.

Method: Mod_$^t$Bu_1

Tert-butyl ester deprotection was made by following procedure; the activated side chain from previous procedure 2 was dissolved in a mixture of TFA with 1-3% of water. The mixture was stirred at RT until the reaction was complete typically from 1 to 3 hours. Alternatively concentrated hydro chloric acid or TFA or a 1:1 mixture of TFA and a suitable solvent such as THF or DCM could be used instead. The product mixture was subjected to evaporation under vacuum to yield a crude oil. Precipitation of the oil in an appropriate solvent such as diethyl ether, isopropyl ether, tert-butyl methyl ether or heptane followed by filtration gave crude material.

The activated side chains were dried under vacuum, analysed by UPLC, MS or NMR and used in the examples described in section C without further purification.

A2. General Methods of Detection. Analysis and Characterisation

1. LC-MS Methods

Method: LC-MS_A_1

Analysis was performed on a setup consisting of Waters H-Class UPLC system fitted with a QDa mass spectrometer. The instrument control and data acquisition were done by the Empower 3 Build 3471 SPs software.

The UPLC pump was connected to two eluent reservoirs containing:

A: 0.1% (vol/vol) Formic acid in water

B: 0.1% (vol/vol) Formic acid in acetonitrile

The analysis was performed at RT by injecting an appropriate volume of the sample (preferably 2-10 μl) onto the column which was eluted with a gradient of A and B.

The UPLC conditions, detector settings and mass spectrometer settings were:

Column: Acquity UPLC® H Waters BEH C-18, 1.7 μm, 2.1 mm×50 mm.

Gradient: 10%-90% (vol/vol) acetonitrile linear during 9 min at 0.40 ml/min

Detection: 214 nm (analogue output from TUV (Tunable UV detector))

MS ionisation mode: API-ES (positive or negative).

Scan: 250-1250 amu) in step 0.1 of amu.

Method: LC-MS_A_2

RP-analysis was performed using Waters Acquity UPLC system. UV detection at 214 and 280 nm. Column: Waters Acquity BEH C18, 1.7 um, 2.1×150 mm. Column own temperature=40° C.

A: water

B: acetonitrile

D: 50 mM ammonium formate pH 9 in water

Gradient: 95 to 0% (vol/vol) A, 0 to 95% (vol/vol) B and 5% (vol/vol) D, 4 min, 0.4 ml/min Detector: Waters Xevo G2-XS Qtof negative scan 50-4000

Method: LC-MS_A_3

RP-analysis was performed using Waters Acquity UPLC system. UV detection at 214 and 280 nm. Column: Waters Acquity BEH C18, 1.7 um, 2.1×150 mm. Column own temperature=40° C.

A: 0.10% (vol/vol) formic acid in water

B: 0.10% (vol/vol) formic acid in acetonitrile

Gradient: 5 to 95% (vol/vol) B, over 4 min 0.4 ml/min

Detector: Waters Xevo G2-XS Qtof positive scan 50-4000

2. UPLC and HPLC Methods

Method: UPLC_A_1

RP-analysis was performed using Waters Acquity UPLC system fitted TUV analytical flow cell detector. UV detection at 210 nm. Column: Waters C18 BEH, 1.7 μm, 100 Å, 50 mm×2.1 mm. Column own temperature=35° C.

Eluent:A 10% (vol/vol) acetonitrile+0.1% (vol/vol) TFA in water.

Eluent:B 95% (vol/vol) acetonitrile+0.1% TFA (vol/vol) in water.

Flow 0.5 mL/min, gradient: 70%-40% A (vol/vol) over 1.5 min, 40% (vol/vol) A for 1.2 min, 40-0% (vol/vol) A over 0.05 min, 0% A for 1.25 min.

Method: UPLC_A_2

RP-analysis was performed using Waters Acquity UPLC system fitted with Waters Acquity PDA detector. UV detection at 214, 254 and 280 nm. Column: Kinetex C18, 1.7 μm, 100 Å, 50 mm×2.1 mm. Column own temperature=35° C. Linear gradient of 10-90% (vol/vol) acetonitrile+0.1% (vol/vol) TFA in water. Flow 0.6 mL/min.

Method: UPLC_A_3

RP-analysis was performed using Waters Acquity UPLC system. UV detection at 214 nm. Column: Waters C18 BEH, 1.7 um, 2.1×150 mm. Column own temperature=40° C.
- A: 0.05% (vol/vol) TFA in water
- B: 0.05% (vol/vol) TFA in acetonitrile Gradient: 5 to 60% (vol/vol) B, 16 min, 0.4 ml/min Method: UPLC_A_4

RP-analysis was performed using Waters Acquity UPLC system. UV detection at 214 nm. Column: Waters C18 BEH, 1.7 um, 2.1×150 mm. Column own temperature=40° C.
- A: 0.05% (vol/vol) TFA in water
- B: 0.05% (vol/vol) TFA in acetonitrile
- Gradient: 5 to 95% (vol/vol) B, 12 min, 0.4 ml/min Method: UPLC_A_5

RP-analysis was performed using Waters Acquity UPLC system. UV detection at 214 nm. Column: Waters C18 BEH, 1.7 um, 2.1×50 mm. Column own temperature=40° C.
- A: 0.05% (vol/vol) TFA in water
- B: 0.05% (vol/vol) TFA in acetonitrile
- Gradient: 5 to 95% (vol/vol) B, 4 min, 0.45 ml/min
- QDA detector positive scan 100-1250

Method: UPLC-MS_A_6

RP-analysis was performed using Waters Acquity UPLC system. UV detection at 214 nm. Column: Waters C18 BEH, 1.7 um, 2.1×150 mm. Column own temperature=40° C.
- A: 0.05% (vol/vol) TFA in water
- B: 0.05% (vol/vol) TFA in acetonitrile
- Gradient: 5 to 60% (vol/vol) B, 16 min, 0.4 ml/min
- QDA detector positive scan 100-1250

Method: UPLC_A_7

RP-analysis was performed using Waters Acquity UPLC system. UV detection at 214 nm. Column: Waters C18 BEH, 1.7 um, 2.1×150 mm. Column own temperature=40° C.
- A: 0.05% (vol/vol) TFA in water
- B: 0.05% (vol/vol) TFA in acetonitrile
- Gradient: 5 to 95% (vol/vol) B, 16 min, 0.4 ml/min Method: HPLC_A_1

RP-analysis was performed using a Dionex Ultimate 3000 system fitted with a Kinetex C18 2.6 μm, 100 Å, 150 mm×4.6 mm column. UV detection at 210 nm.
- Eluent A: 10% acetonitrile+0.1% TFA in water
- Eluent B: 90% acetonitrile, 0.1% TFA in water
- Flow 1.5 mL/min, linear gradient of 40-100% (vol/vol) B over 9 min.

B. Synthesis of Activated Side Chains of the Invention and Reference Side Chains Examples 1-8 describe the synthesis of eight activated side chains of the invention, all with activator group 3,5-DC-2-HBSA (Chem. 1). Examples 8B-8D describe the synthesis of additional activated side chains of the invention, with activator group 3,5-DC-2-HBSA or 3,5-DC-2-HDMBSA (3,5-dichloro-2-hydroxy-N,N-dimethyl-benzenesulfonamide).

Examples A-E describe the synthesis of five activated reference side chains where the activator group is selected from four different activators (NHS, 2,4-DC-phenol, 2,6-DC-phenol, and 3,5-DC-4-HBSA (Chem. 2 to Chem. 5, respectively)).

Example 1: Preparation of 3,5-DC-2-HBSA ester: 20-[[4-[[(1S)-1-carboxy-4-[2-[2-[2-[2-[2-(2,4-dichloro-6-sulfo-phenoxy)-2-oxo-ethoxy]ethoxy]ethylamino]-2-oxo-ethoxy]ethoxy]ethylamino]-4-oxo-butyl]carbamoyl]cyclohexyl]methylamino]-20-oxo-icosanoic acid Chem. 21

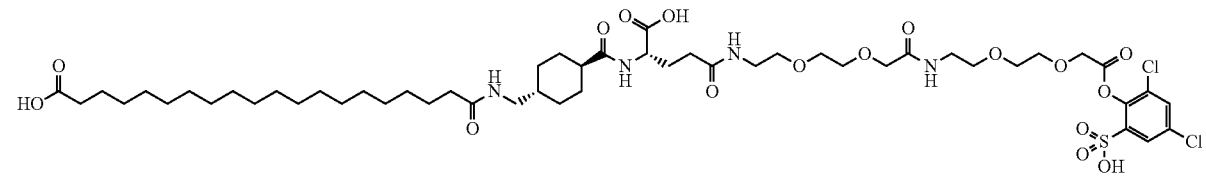

Bn protected side chain was prepared as described in section A. After TFA scavenging the DCM filtered solution was added TEA until pH 9.5 (tested with wet pH paper) followed by 3,5-dichloro-2-hydroxybenzene sulfonyl chloride (0.62g, 2.37 mmol, 1.1eq) and stirred for 4 hours at room temperature. The solution was washed with 5% (vol/vol) aq. $NaHCO_3$, 20 mL×3 or 0.5M $KHSO_4$, followed by saturated solution of sodium chloride (20 mL×3). The organic phase was dried over $MgSO_4$, followed by solvent removal in vacuo resulting in a sticky oil.

The oil was dissolved in HFIP (10 ml) and added 5% (w/vol) Pd/C (298 mg, 10% w/w, (Escat™ 1431, Strem Chemicals)). The atmosphere in the reaction flask was exchanged to nitrogen, followed by exchange to hydrogen.

The reaction was stirred under a hydrogen atmosphere (1 bar) for 3.5 hours. The atmosphere was then exchanged to nitrogen before being changed back to atmospheric air. Reaction solution was filtered through 0.4 μm PTFE filter. The Pd/C was washed with HFIP (4 mL) in total. After the HFIP solution was cooled on ice bath to below 5° C., diethyl ether (14 mL), was added to give a white suspension. The precipitate was collected by filtration and washed with cold diethyl ether twice. The precipitate was then dried under vacuum for 3 days, yielding the ester as a white powder in 1.62 g. Active content of material from 1H qNMR is 75.8% w/w. Yield 46%.

The compound was analysed by $^1$H NMR and LC-MS.

$^1$H NMR (400 MHz, DMSO-d6) δ ppm 1.20-1.35 (m, 32H) 1.42-1.55 (m, 4H) 1.68-1.83 (m, 5H) 1.89-2.01 (m, 1H) 2.05 (t, 2H) 2.11-2.23 (m, 5H) 2.89 (d, 2H) 3.21 (q, 2H) 3.30 (q, 2H) 3.42 (t, 2H) 3.47 (t, 2H) 3.51-3.62 (m, 7H) 3.67-3.74 (m, 2H) 3.89 (s, 2H) 4.09-4.18 (m, 1H) 4.41 (br. s., 2H) 7.65-7.78 (m, 4H) 7.89 (t, 1H) 7.94 (d, 1H)

LC-MS_A_1: Rt=4.9 min m/z=1125.6=[M+1]$^+$

Example 2: Preparation of 3,5-DC-2-HBSA ester: 18-[[(1S)-1-carboxy-4-[2-[2-[2-[2-[2-[2-(2,4-dichloro-6-sulfo-phenoxy)-2-oxo-ethoxy]ethoxy]ethylamino]-2-oxo-ethoxy]ethoxy]ethylamino]-4-oxo-butyl]amino]-18-oxo-octadecanoic acid

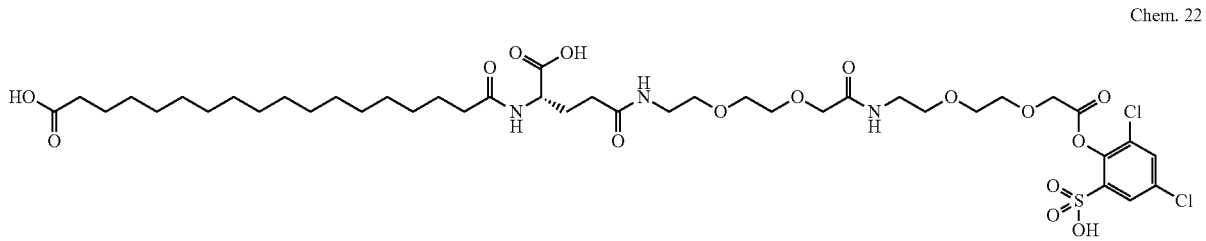 [SMILES: O=C(O)CCCCCCCCCCCCCCCCC(=O)N[C@@H](CCC(=O)NCCOCCOCC(=O)NCCOCCOCC(=O)Oc1c(Cl)cc(Cl)cc1S(=O)(=O)O)C(=O)O]

Chem. 22

Bn protected side chain was prepared as described in section A, and the side chain was activated with the same procedure used in Example 1. Isopropanol was used for the hydrogenation and tert-butyl methyl ether was used for the precipitation. The compound was characterised by LC-MS and $^1$H NMR.

$^1$H NMR (400 MHz, DMSO-d6) δ ppm 1.22-1.23 (m, 24H) 1.41-1.54 (m, 4H) 1.70-1.82 (m, 1H) 1.88-2.01 (m, 1H) 2.05-2.22 (m, 6H) 3.20 (q, 2H) 3.28 (q, 2H) 3.40 (t, 2H) 3.46 (t, 2H) 3.50-3.61 (m, 6H) 3.69-3.69 (m, 2H) 3.88 (s, 2H) 4.09-4.19 (m, 1H) 4.40 (s, 2H) 7.63-7.71 (m, 2H) 7.75 (s, 1H) 7.89 (t, 1H) 8.03 (d, 1H)

LC-MS_A_1: Rt=3.6 min m/z=958.5=[M+1]$^+$

Example 3: Preparation of 3,5-DC-2-HBSA ester: 4-[10-[[(1S)-1-carboxy-4-[2-[2-[2-[2-[2-[2-(2,4-dichloro-6-sulfo-phenoxy)-2-oxo-ethoxy]ethoxy]ethylamino]-2-oxo-ethoxy]ethoxy]ethylamino]-4-oxo-butyl]amino]-10-oxo-decoxy]benzoic acid

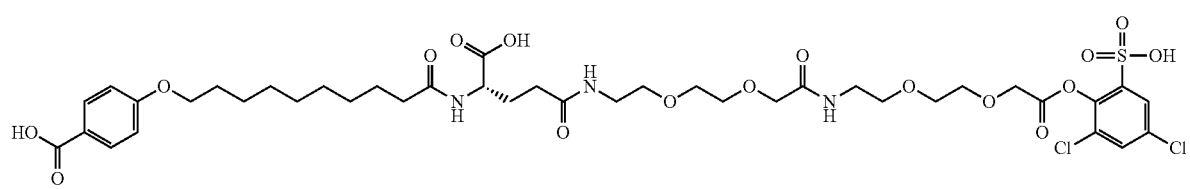

Chem. 23

Bn protected side chain is prepared as described in section A, and the side chain is activated with the same procedure used in Example 1.

Example 4: Preparation of 3,5-DC-2-HBSA ester: 20-[[4-[[(1S)-1-carboxy-4-[2-[2-[2-[2-[2-[2-[2-[2-[2-[2-[2-[[(5S)-5-[[2-[2-[2-[[2-[2-[2-[[2-[2-[2-[[2-[2-[2-[[(4S)-4-carboxy-4-[[4-[(19-carboxynonade-canoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]-6-[2-[2-[2-[2-[2-[2-(2,4-dichloro-6-sulfo-phenoxy)-2-oxo-ethoxy]ethoxy]ethylamino]-2-oxo-ethoxy]ethoxy]ethylamino]-6-oxo-hexyl]amino]-2-oxo-ethoxy]ethoxy]ethylamino]-2-oxo-ethoxy]ethoxy]ethylamino]-2-oxo-ethoxy]ethoxy]ethylamino]-2-oxo-ethoxy]ethoxy]ethylamino]-4-oxo-butyl]carbamoyl]cyclohexyl]methylamino]-20-oxo-icosanoic acid

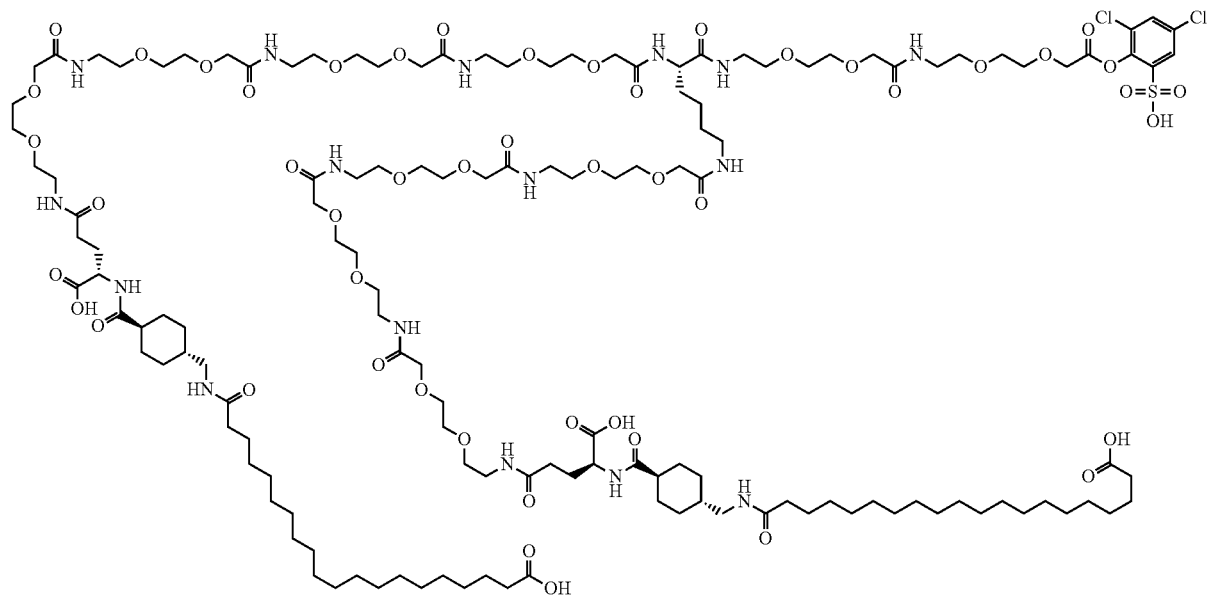

Chem. 24

Bn protected side chain is prepared as described in section A, and the side chain is activated with the same procedure used in Example 1.

Example 5: Preparation of 3,5-DC-2-HBSA ester: 20-[[4-[[(1S)-1-carboxy-4-[2-[2-[2-[2-[2-[2-[[(5S)-5-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]-6-[2-[2-[2-(2,4-dichloro-6-sulfo-phenoxy)-2-oxo-ethoxy]ethoxy]ethylamino]-6-oxo-hexyl]amino]-2-oxo-ethoxy]ethoxy]ethylamino]-2-oxo-ethoxy]ethoxy]ethylamino]-4-oxo-butyl]carbamoyl]cyclohexyl]methylamino]-20-oxo-icosanoic acid

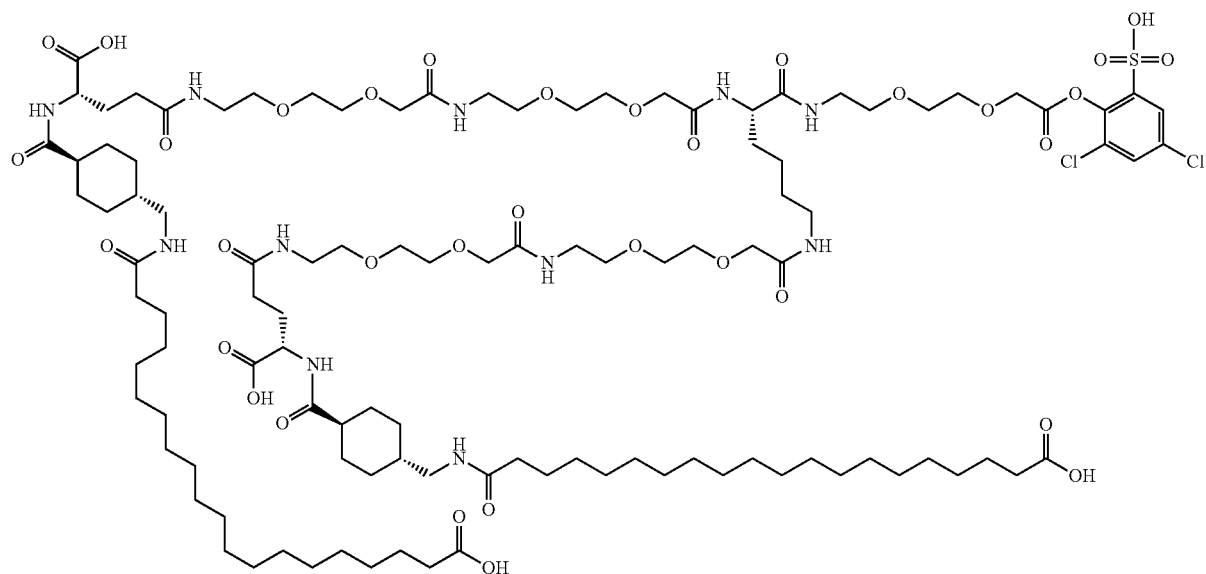

Chem. 25

Bn protected side chain is prepared as described in section A, and the side chain is activated with the same procedure used in Example 1.

Example 6: Preparation of 3,5-DC-2-BSA ester: 20-[[4-[[(1S)-1-carboxy-4-[2-[2-[2-[2-[2-[2-[2-[2-[2-[2-[2-[2-[3-[3-[[2-[2-[2-[[2-[2-[2-[[2-[2-[2-[[2- [2-[2-[[(4S)-4-carboxy-4-[[4-[(19-carboxynonade-canoylamino)methyl]cyclohexanecarbonyl]amino] butanoyl]amino]ethoxy]ethoxy]acetyl]amino] ethoxy]ethoxy]acetyl]amino]ethoxy]ethoxy]acetyl] amino]ethoxy]ethoxy]acetyl]amino]propyl-[2-[2-[2-[2-[2-[2-[2-(2,4-dichloro-6-sulfo-phenoxy)-2-oxo-ethoxy]ethoxy]ethylamino]-2-oxo-ethoxy]ethoxy] ethylamino]-2-oxo-ethyl]amino]propylamino]-2-oxo-ethoxy]ethoxy]ethylamino]-2-oxo-ethoxy] ethoxy]ethylamino]-2-oxo-ethoxy]ethoxy] ethylamino]-2-oxo-ethoxy]ethoxy]ethylamino]-4-oxo-butyl]carbamoyl]cyclohexyl]methylamino]-20-oxo-icosanoic acid

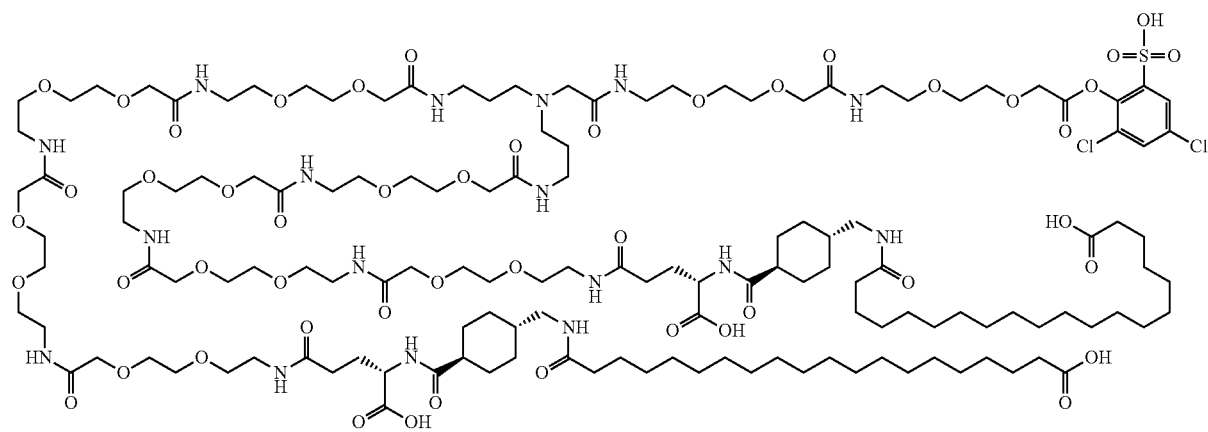

Chem. 26

Bn protected side chain is prepared as described in section A, and the side chain is activated with the same procedure used in Example 1.

Example 7: Preparation of 3,5-DC-2-BSA ester: 20-[[4-[[(1S')-1-carboxy-4-[2-[2-[2-[2-[2-[2-[3-[3-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]propyl-[2-[2-[2-[2-[2-[2-[2-[2-[2-[2-[2-(2,4-dichloro-6-sulfo-phenoxy)-2-oxo-ethoxy]ethoxy]ethylamino]-2-oxo-ethoxy]ethoxy]ethylamino]-2-oxo-ethoxy]ethoxy]ethylamino]-2-oxo-ethoxy]ethoxy]ethylamino]-2-oxo-ethyl]amino]propylamino]-2-oxo-ethoxy]ethoxy]ethylamino]-2-oxo-ethoxy]ethoxy]ethylamino]-4-oxo-butyl]carbamoyl]cyclohexyl]methylamino]-20-oxo-icosanoic acid; formic acid

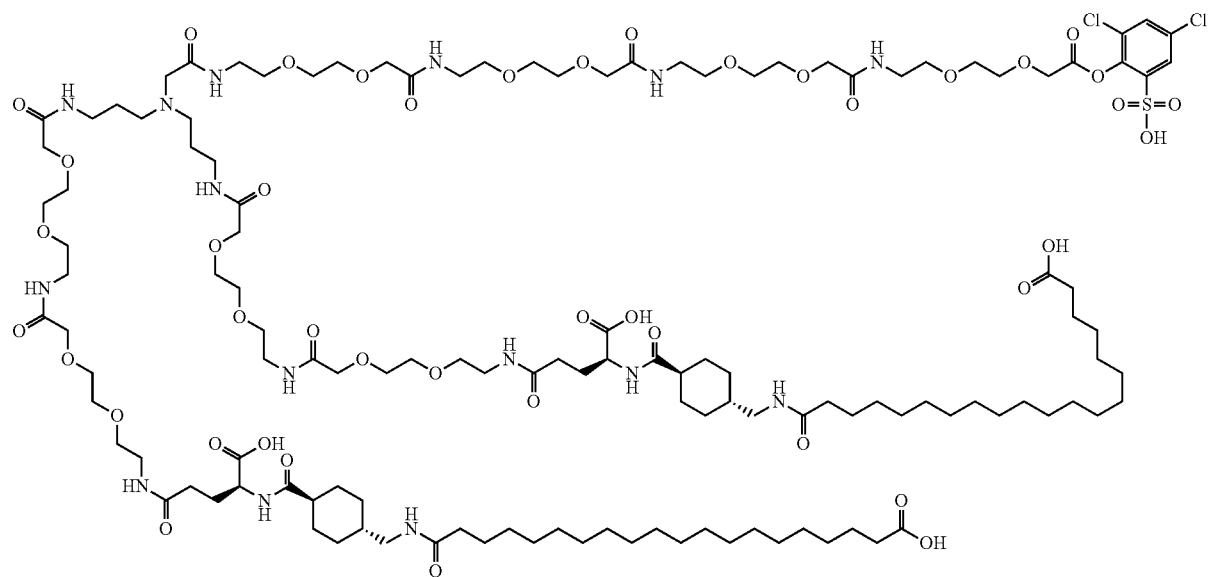

Chem. 27

Bn protected side chain is prepared as described in section A, and the side chain is activated with the same procedure used in Example 1.

Example 8: Preparation of 3,5-DC-2-HBSA ester: 20-[[(1S)-1-carboxy-4-[2-[2-[2-[2-[2-[2-(2,4-dichloro-6-sulfo-phenoxy)-2-oxo-ethoxy]ethoxy]ethylamino]-2-oxo-ethoxy]ethoxy]ethylamino]-4-oxo-butyl]amino]-20-oxo-icosanoic acid

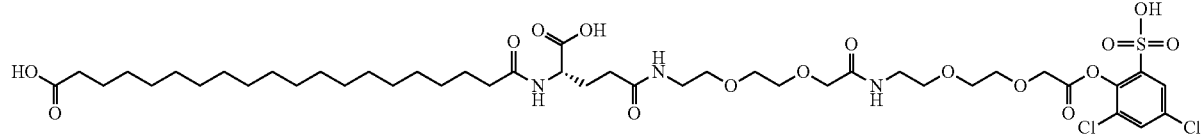

Chem. 28

Bn protected side chain is prepared as described in section A, and the side chain is activated with the same procedure used in Example 1. Isopropanol is used for the hydrogenation and tert-butyl methyl ether is used for the precipitation.

Example 8B: Preparation of 3,5-dichloro-2-(2-methoxyacetyl)oxy-benzenesulfonic acid

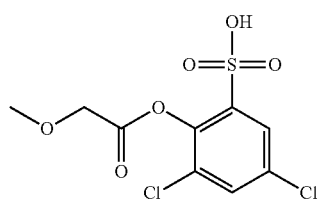

Chem. 36

Methoxyacetic acid (92 µL, 1.20 mmol, 1.0eq) was dissolved in DCM (2 mL). Triethyl amine (352 µL, 2.53 mmol, 2.1eq) was added to the stirred solution at RT. 3,5-dichloro-2-hydroxybenzene sulfonyl chloride (0.331g, 1.26 mmol, 1.0eq) was dissolved in DCM (1 mL) and added over 5 min to the methoxyacetic acid solution. The solution was stirred for 1 hour at room temperature. The solvent was removed under reduced pressure. The crude was dissolved in EtOAc (10 mL) and the solution was washed with a mixture of 5% (vol/vol) aq. $KHSO_4$ and brine (5 mL/5 mL). The aqueous phase was extracted with EtOAc (10 mL). The combined organic phases were dried over $MgSO_4$, followed by solvent removal in vacuo. The crude was dissolved in $CH_3CN$ and water 1/10 (50 mL) and freeze dried.

Yield of product (0.16 g, 42%). Active content of material from 1H qNMR is 70% w/w.

The compound was characterised by $^1$H NMR and LC-MS.

$^1$H NMR (400 MHz, DMSO-d6) δ ppm 3.39 (s, 3H) 4.31 (s, 2H) 7.7.65 (s, 1H) 7.77 (s, 1H)

LC-MS_A_2: Rt=2.06 min m/z=313=[M−1]$^−$

Example 8C: Preparation of 3,5-DC-2-HDMBSA-ester: 18-[[(1S)-1-carboxy-4-[2-[2-[2-[2-[2-[2,4-dichloro-6-(dimethylsulfamoyl)phenoxyl-2-oxo-ethoxy]ethoxy]ethylamino]-2-oxo-ethoxy]ethoxy] ethylamino]-4-oxo-butyl]amino]-18-oxo-octadecanoic acid t-Bu protected C18-diacid-γGlu-Ado-Ado-OH (0.461 mmol, 0.390g), 3,5-dichloro-2-hydroxy-N,N-dimethyl-benzenesulfonamide (0.507 mmol, 0.137g, 1.1eq) and DCC (0.553 mmol, 0.114g, 1.2eq) was dissolved in 1.5 mL DCM. Solution was stirred at RT for 18 hours. The reaction mixtures were analysed by UPLC_A_7. Extra DCC (0.340 mmol, 0.07g, 0.7eq) was added and the reaction was stirred at RT for another 18 hours. The conversion was ~57% when the DCU was removed by filtration. The supernatant was washed with brine and dried over $Mg_2SO_4$. The crude was purified using silicagel column chromatography with a gradient eluent from DCM to 5% MeOH in DCM. After evaporation the product yield was 307 mg (61%).

Method Mod_$^t$Bu_1 was used to cleave the tBu-esters for 1.5 hours. The cleavage mixture was evaporated under reduced pressure. The compound was twice dissolved in MeCN and evaporated. The sticky oil was triturated in diethyl ether. A white precipitate was obtained. Yield of product (0.198g, 72%). Active content of material from 1H qNMR is 92% w/w The compound was characterised by LC-MS and $^1$H NMR.

$^1$H NMR (400 MHz, DMSO-d6) δ ppm 1.22-1.23 (m, 24H) 1.41-1.54 (m, 4H) 1.70-1.82 (m, 1H) 1.88-2.01 (m, 1H) 2.05-2.22 (m, 6H) 2.70 (s, 6H) 3.20 (q, 2H) 3.28 (q, 2H) 3.40 (t, 2H) 3.46 (t, 2H) 3.50-3.61 (m, 6H) 3.69-3.69 (m, 2H) 3.88 (s, 2H) 4.09-4.19 (m, 1H) 4.40 (s, 2H) 7.67 (t, 1H) 7.83 (d, 1H) 7.89 (t, 1H) 8.04 (d, 1H) 8.24 (d, 1H)

LC-MS_A_3: Rt=3.79 min m/z=986.4=[M+1]$^+$

Example 8D: Preparation of 3,5-DC-2-HBSA-ester: 3,5-dichloro-2-[3-[2-[2-(2-prop-2-ynoxyethoxy) ethoxy]ethoxy]propanoyloxy]benzenesulfonic acid

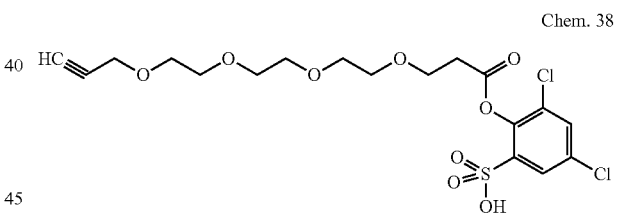

Chem. 38

The compound was prepared using the procedure described in Example 8B using 3-[2-[2-(2-prop-2-ynoxy-ethoxy)ethoxy]ethoxy]propanoic acid and 3,5-dichloro-2-hydroxybenzene sulfonyl chloride. Yield of product (294 mg). Active content of material from 1H qNMR is 77% w/w.

The compound was analysed by $^1$H NMR and LC-MS.

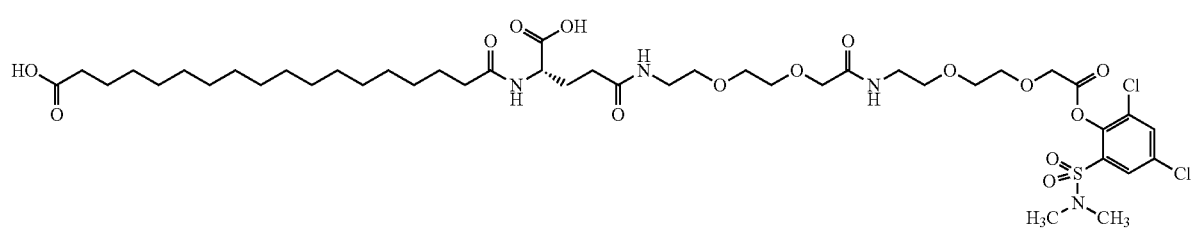

Chem. 37

$^1$H NMR (400 MHz, DMSO-d6) δ ppm 1.78-1.82 (m, 2H) 2.79 (br s, 2H) 3.44 (t, 1H) 3.52-3.55 (m, 12H) 3.73 (t, 2H) 4.15 (d, 2H) 7.63 (d, 1H) 7.75 (d, 1H)

UPLC_A_5: Rt=2.73 min m/z=485=[M+1]$^+$

Example A: Preparation of NHS ester: 18-[[(1S)-1-carboxy-4-[2-[2-[2-[2-[2-[2-(2,5-dioxopyrrolidin-1-yl)oxy-2-oxo-ethoxy]ethoxy]ethylamino]-2-oxo-ethoxy]ethoxy]ethylamino]-4-oxo-butyl]amino]-18-oxo-octadecanoic acid Bn protected C20-diacid-Trx-γGlu-Ado-Ado-OH (1.36 mmol, 1.466g), 2.4-dichlorophenol (2.69 mmol, 0.438g, 2eq) and DMAP (1.41 mmol, 0.172g, 1eq) was dissolved in 30 mL DCM. To this solution was added EDC (2.02 mmol, 0.388g, 1.5eq). Solution was stirred for 2 hours.

Solution was extracted with 0.5M NaOH (15 mL×3), followed by extraction with 0.5M HCl in 10% NaCl solution (15 mL×3). The organic phase was then dried over MgSO$_4$, filtered and the solvent removed in vacuo. The product was used without further purification. The product yield was 1.30g.

Chem. 31

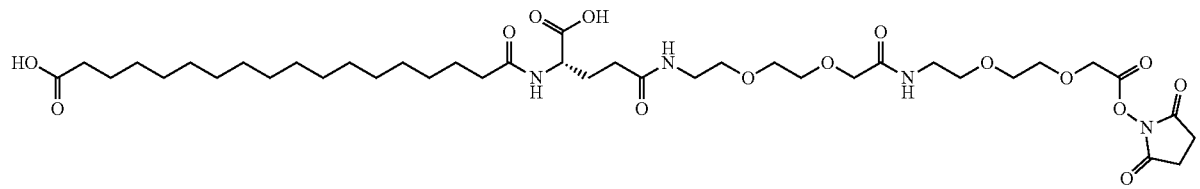

The compound was prepared as described in WO2010/029159.

Example B: Preparation of NHS ester: 20-[[4-[[(1S)-1-carboxy-4-[2-[2-[2-[2-[2-[2-(2,5-dioxopyrrolidin-1-yl)oxy-2-oxo-ethoxy]ethoxy]ethylamino]-2-oxo-ethoxy]ethoxy]ethylamino]-4-oxo-butyl]carbamoyl]cyclohexyl]methylamino]-20-oxo-icosanoic acid 5% (w/vol) Pd/C (10% w/w, 0.132g, (Escat™ 1431, Strem Chemicals)) was added to a stirring HFIP solution (9 mL) with the activated material (1.30g). The atmosphere in the reaction flask was exchanged to nitrogen, followed by hydrogen exchange. The reaction was stirred under a hydrogen atmosphere (1 bar) for 5 hours. The atmosphere was then exchanged to nitrogen before being changed back to atmospheric air. The reaction solution was then filtered through 0.45 μm PTFE filter. The Pd(0) on charcoal was washed with HFIP (3 mL). The solution was cooled to below Chem. 32

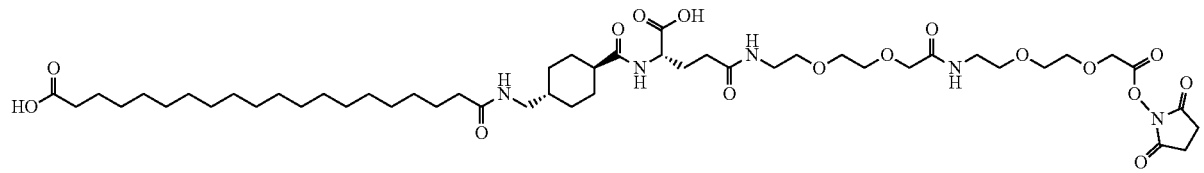

The compound was prepared as described in WO2015/000942.

Example C: Preparation of 2,4-DC-phenol ester: 20-[[4-[[(1S)-1-carboxy-4-[2-[2-[2-[2-[2-[2-(2,4-dichlorophenoxy)-2-oxo-ethoxy]ethoxy]ethylamino]-2-oxo-ethoxy]ethoxy]ethylamino]-4-oxo-butyl]carbamoyl]cyclohexyl]methylamino]-20-oxo-icosanoic acid 5° C. and added diethyl ether (20 mL) resulting in a white precipitate. The precipitate was collected by filtration and washed with diethyl ether (10 mL). The product was dried under vacuum for 4 days.

Yield of product (0.8326g, 45.6%). Active content of material from 1H qNMR is 84% w/w.

The compound was analysed by $^1$H NMR and LCMS.

$^1$H NMR (400 MHz, DMSO-d6) δ ppm 1.15-1.36 (m, 32H) 1.41-1.53 (m, 4H) 1.67-1.82 (m, 5H) 1.90-2.00 (m, 1H) 2.05 (t, 2H) 2.09-2.22 (m, 5H) 2.89 (t, 2H) 3.20 (q, 2H)

Chem. 33

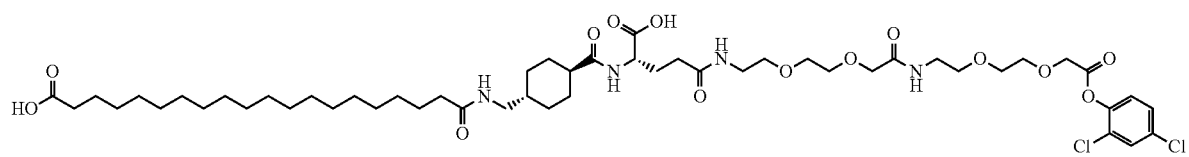

3.29 (q, 2H) 3.41 (t, 2H) 3.47 (t, 2H) 3.50-3.62 (m, 7H) 3.67-3.74 (m, 2H) 3.88 (s, 2H) 4.10-4.18 (m, 1H) 4.51 (s, 2H) 7.41 (d, 1H) 7.50 (d, 1H) 7.66 (t, 1H) 7.72 (t, 1H) 7.78 (s, 1H) 7.89 (t, 1H) 7.96 (d, 1H)

LC-MS_A_1: Rt=5.9 min m/z=1045.6=[M+1]$^+$

Example D: Preparation of 2,6-DC phenol ester: 20-[[4-[[(1S)-1-carboxy-4-[2-[2-[2-[2-[2-[2-(2,6-dichlorophenoxy)-2-oxo-ethoxy]ethoxy]ethyl-amino]-2-oxo-ethoxy]ethoxy]ethylamino]-4-oxo-butyl]carbamoyl]cyclohexyl]methylamino]-20-oxo-icosanoic acid

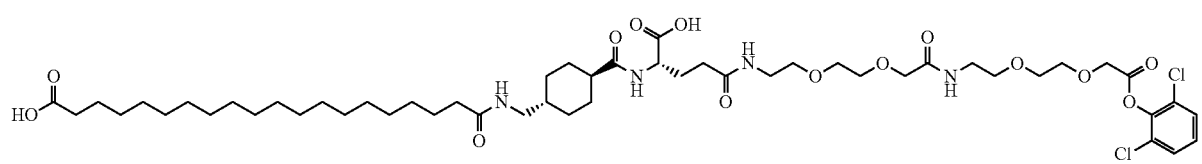

Chem. 34

The compound was prepared using the procedure described in Example C using 2,6-dichloro phenol and analysed by $^1$H NMR and LC-MS.

$^1$H NMR (400 MHz, DMSO-d6) δ ppm 1.16-1.35 (m, 32H) 1.41-1.54 (m, 4H) 1.67-1.82 (m, 5H) 1.89-2.01 (m, 1H) 2.06 (t, 2H) 2.10-2.23 (m, 5H) 2.89 (t, 2H) 3.21 (q, 2H) 3.30 (q, 2H) 3.41 (t, 2H) 3.48 (t, 2H) 3.51-3.63 (m, 7H) 3.70-3.76 (m, 2H) 3.89 (s, 2H) 4.10-4.18 (m, 1H) 4.61 (s, 2H) 7.38 (t, 1H) 7.63 (d, 2H) 7.68 (t, 1H) 7.74 (t, 1H) 7.91 (t, 1H) 7.97 (d, 1H)

LC-MS_A_1: Rt=5.7 m/z=1045.6=[M+1]$^+$

Example E: Preparation of 3,5-DC-4-HBSA ester: 18-[[(1S)-1-carboxy-4-[2-[2-[2-[2-[2-[2-(2,6-di-chloro-4-sulfo-phenoxy)-2-oxo-ethoxy]ethoxy]ethyl-amino]-2-oxo-ethoxy]ethoxy]ethylamino]-4-oxo-butyl]amino]-18-oxo-octadecanoic acid The compound was prepared using the procedure described in Example C using 2,6-dichloro-4-sulfo phenol and characterised by $^1$H NMR and LC-MS.

$^1$H NMR (400 MHz, DMSO-d6) δ ppm 1.22-1.23 (m, 24H) 1.41-1.54 (m, 4H) 1.70-1.82 (m, 1H) 1.88-2.01 (m, 1H) 2.05-2.22 (m, 6H) 3.20 (q, 2H) 3.28 (q, 2H) 3.40 (t, 2H) 3.46 (t, 2H) 3.50-3.61 (m, 6H) 3.69-3.69 (m, 2H) 3.88 (s, 2H) 4.09-4.19 (m, 1H) 4.40 (s, 2H) 7.63-7.71 (m, 3H) 7.89 (t, 1H) 8.03 (d, 1H)

LC-MS_A_1: Rt=3.3 min m/z=958.5=[M+1]$^+$

C. Hydrolytic Stability of the Activated Side Chains of the Invention and their Use in Acylation Reactions Example 9: Hydrolytic Stability of Activated Side Chains The purpose of this example is to test the hydrolytic stability of activated side chains of the invention. More in particular, the hydrolytic stability of the activated side chains of Examples 1 and 2 (both activated with 3,5-DC-2-HBSA (Chem. 1b)) is compared to the hydrolytic stability of four reference side chains (Examples B, C, D, and E activated with four different activators NHS, 2,4-DC-phenol, 2,6-DC-phenol, and 3,5-DC-4-HBSA (Chem. 2, 3, 4, 5, respectively)).

Procedure 0.1 mmol of each activated side chain was dissolved in 1.0 mL NMP. To this solution was added 5 mL 1M NaHCO$_3$ buffer solution adjusted to pH 10.0 with NaOH. Solution was stirred (pH ~10.3) with aliquots being taken at different time intervals to determine to which extent the various activated side chains were hydrolysed.

The reaction mixtures were analysed by UPLC (Example no. 2 and E—UPLC_A_1) and HPLC (Example no. 1, B, C, and D—HPLC_A_1), and the percent of hydrolysis for the various side chains was estimated by area comparison in UV detection at 210 nm. In each example, the combined areas for released activation group (peak A) and non-activated side chain (peak B), was compared to area for activated side chain (peak C). The retention times (rt-A, rt-B, and rt-C for the various peaks (peak A, peak B, and peak C) for each side chain are summarised as follows; 1 (rt-A=1.94 min,

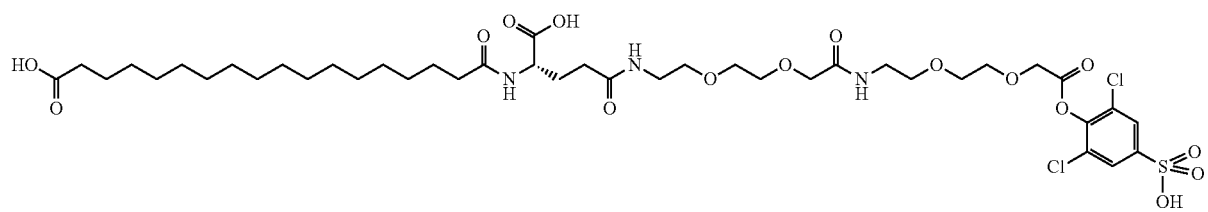

Chem. 35 rt-B=7.18-7.25 min, rt-C=7.48 min, HPLC_A_1), 2 (rt-A=0.48 min, rt-B=2.11 min, rt-C=2.29 min, UPLC_A_1), B (only rt-B detected at time point for analysis), C (rt-A=4.40 min, rt-B=7.25 min, HPLC_A_1), D (rt-A=4.01 min, rt-B=7.25 min, rt-C=10.16 min, HPLC_A_1), E (rt-A=2.08 min, rt-B=2.10 min, rt-C=2.10 min, UPLC_A_1).

The hydrolysis data is summarised in Table 1. "Hydrolysis time" indicates the time point at which the aliquot was taken for analysis of % hydrolysis, and "Hydrolysis (%) at pH 10.3" shows the result of the determination of side chain hydrolysed at that time.

TABLE 1

Hydrolysis of activated side chains

| Example no. | Activator | Hydrolysis time (min) | Hydrolysis (%) at pH 10.3 |
|---|---|---|---|
| 1 | 3,5-DC-2-HBSA | 1269 | 88.1 |
| 2 | 3,5-DC-2-HBSA | 1070 | 88.1 |
| B | NHS | 0 | Quantitative |
| C | 2,4-DC-phenol | 0.16 | Quantitative |
| D | 2,6-DC-phenol | 2 | 93.4 |
| E | 3,5-DC-4-HBSA | 2.5 | Quantitative |

The results in Table 1 show that the activated side chain of Example B (with state of the art activator NHS) is hydrolytically very unstable as it was quantitatively hydrolysed within a minute (hydrolysis time=0). Contrary to this approximately 12% of the activated side chains of the invention (Examples 1 and 2) still remained even after prolonged exposure to the basic conditions (hydrolysis times around 1100-1300 minutes). The two tested activated side chains of the invention show a similar and very good hydrolytic stability which indicates that structural variation in the distal part of the side chain (distal to the point of attachment of the activator) does not appear to influence the hydrolytic stability of the activated side chain. In Table 1 the result "Quantitative" refers to more than 99% of the side chain being hydrolysed.

The results in Table 1 also show that the activated side chains of the invention (Examples 1 and 2) are much more stable against hydrolysis than side chains activated with three different activators of somewhat similar or very similar structure (Examples C, D, and E). More in particular, the activated side chains of Examples C and D (with activator 2,4- and 2,6-DC-phenol, respectively) also hydrolyse very fast and almost quantitatively. Furthermore, a comparison of the results for the activated side chains of Examples 1 and 2 of the invention (3,5-DC-2-HBSA) with those for the activated side chain of Example E (3,5-DC-4-HBSA) makes it clear that the position of the sulfonic acid group on the phenyl ring makes a great difference (the sulfonic acid should be in the ortho position relative to the ester bond rather than in the para position).

Example 10: Preparation of a mono-acylated GLP-1 analogue N{Epsilon-26}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Arg34]-GLP-1-(9-37)-peptide The purpose of this example is to study the use of the activated side chain of the invention in an acylation reaction for producing a mono-acylated GLP-1 analogue. The activated side chain of the invention used in this example is that of Example 2, and it is tested along with the activated side chains of Example A, for comparison. Process robustness is in focus in this example, viz. alternative ways of adding the activated side chain of the invention to the GLP-1 analogue in question (slow, intermediate, or fast addition of the side chain in solution, or addition as a solid). The purity of the desired acylated end product (the yield) and the surplus that is needed of the activated side chain for the acylation reaction to proceed as desired are also determined.

The GLP-1 analogue being acylated in this example is (R34)GLP-1(9-37) (SEQ ID NO: 7), which may be prepared, e.g., as described in Example 2 of WO 2009/083549. The side chain which is to be attached to the lysine at position 26 of this analogue consists of a C18 diacid protractor and a gGlu-2×Ado linker.

Acylation Procedure

The GLP-1 analogue (2.03 g) was added 23 mL demineralised water and then added TEA until pH 9.5. A sample was taken out for concentration determination when the mixture was completely dissolved (10 mins). 20 μL solution dissolved in 980 μL 50/25/25 (vol/vol/vol) acetic acid/water/MeCN (dilution 1:40). The concentration was 25.1 g/L.

To 16.0 mL of the GLP-1 analogue solution (0.40 g of the analogue) was added 4.0 mL demineralised water to give a concentration of 20.1 g/L. This solution was adjusted to pH 11.3 with TEA.

The activated side chain of Example 2 containing 181.2 mg of active material, 1.49 eq., was dissolved in 890 μL NMP. Total volume=1070 μL.

For "intermediate" addition thereof a syringe with D=5 mm was used, addition speed set to 1.15eq./10 min. A total of 0.83 mL was added, to give a total added eq. of 1.16 over 11.5 minutes. The pH was manually adjusted during acylation using 1M NaOH. The pH was kept in 11.28-11.32 interval during addition. After addition was stopped the pH was kept between 11.26-11.35 for the rest of the reaction time. The temperature during the acylation was 23.7-24.3° C.

For "fast" addition, the procedure described above was followed with the difference that the side chain was added over a period of 3.3 min.

For "slow" addition, the procedure described above was followed with the difference that the side chain was added over a period of about 30 min.

For addition as a solid, the procedure described above was followed with the difference that all of the non-dissolved side chain was added directly.

Activated Side Chain of Example A, Slow Addition

The acylation reaction with the activated side chain of Example A was conducted in the same way as described above.

Results

The following parameters were determined for each of these experiments, and the results are shown in Table 2 below:

"Eq. SC" which refers to the number of equivalents used of the activated side chain relative to the peptide.

"Backbone %", "Product %" and "Di-acylated %" which are indicative of the purity of the final product. Product refers to the desired end-product which is the mono-acylated compound, the backbone refers to the non-acylated analogue, and di-acylated refers to an undesired by-product of the reaction. The reactions were analysed by UPLC or HPLC methods as indicated below, and the efficiency in the acylation process was estimated by area comparison in UV at 210 nm. For clarity in comparison, the combined area of "Backbone", "Product", and "Di-acylated" was normalized to 100%. The retention times for the peaks of parameter of interest were as follows; "Backbone"—around 1.5-1.6 min (UPLC_A_1) or 3.6 min (HPLC_A_1), "Product"—around 2.1 to 2.3 min (UPLC_A_1) or 5.9 min (HPLC_A_1), "Di-acylated"—around 2.70-3.00 min (UPLC_A_1) or 8.0 min (HPLC_A_1). The analytical samples were taken from the reaction mixtures between 80 and 107 minutes after initial side chain addition.

TABLE 2

Process variations, surplus needed of activated side chain, and purity

| Side chain Example no. | Addition | Eq. SC | Product % | Backbone % | Diacylated % |
|---|---|---|---|---|---|
| A | Solution, slow | 1.10 | 95.6 | 2.2 | 2.2 |
| 2 | Solution, slow | 1.15 | 98.0 | 0.5 | 1.5 |
| 2 | Solution, intermediate | 1.16 | 97.1 | 0.2 | 1.7 |
| 2 | Solution, fast | 1.14 | 93.3 | 0 | 4.7 |
| 2 | Solid | 1.16 | 97.5 | 0.1 | 2.4 |

The results of Table 2 show that, overall, the activated side chain of the invention (Example 2) results in a product of about the same or a better purity as compared to the state of the art activated side chain (Example A), and also a similar surplus of activated side chain is used. The results also show that the activated side chain of the invention provides great process flexibility as the purity of the product and the surplus needed does not depend on the speed of addition, and in fact it can be added as a solid. This is a big advantage as it is an established fact that the known activated side chain (Example A) has to be added very slowly and under rigorous control due to its hydrolytic instability under the acylation reaction conditions.

Thus, these results indicate that the activated side chain of the invention gives a product of similar purity as the known process but with a much more robust acylation process.

Example 11: Preparation of a di-acylated GLP-1 analoque N{Alpha}([Glu22,Arg26,Arg34]-GLP-1-(9-37)-peptidyl)-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys-Gly-Gly-Ser-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys The purpose of this example is to study the use of the activated side chain of the invention in an acylation reaction for producing a di-acylated GLP-1 analogue. Focus is on the purity of the desired di-acylated end product (the yield), and on the surplus that is needed of the activated side chain for the acylation reaction to proceed as desired. The activated side chain of the invention used in this example is that of Example 1, and it is tested along with the activated side chains of Examples B, C, and D, for comparison.

The GLP-1 analogue used in this example is (22E,26R,34R)GLP-1(9-37)(38K,39G,40G,41S,42K) (SEQ ID NO: 3), viz. a C-terminally extended GLP-1 analogue (extended by 5 amino acids) where furthermore two N-terminal amino acids have been deleted and three amino acids substituted, all relative to native GLP-1(7-37) (SEQ ID NO: 1). This analogue is identical to the GLP-1 analogue disclosed in Example 3 of WO 2015/000942 except for the deleted two N-terminal amino acids, and it may be prepared as described in this reference or using any other method known in the art.

Two side chains are to be attached to this analogue, more in particular to the lysines at position 38 and 42. Each side chain consists of a C20 diacid protractor and a Trx-gGlu-2xAdo linker.

Acylation Procedure

To the GLP-1 analogue (2.94g) was added demineralised water (40 mL). The pH of the suspension was adjusted with TEA (100 µL) to pH 10.6 and stirred until all material was dissolved, and by then pH was 9.6. Sample was taken for concentration determination of the GLP-1 analogue in solution. Concentration was 21.5 g/L. 18 mL of this solution (0.43 g, 0.12 mmol) was added demineralised water (2 mL) and adjusted to pH 11.0 with TEA followed by adjustment to pH 11.3 with NaOH (1M).

Activated Side Chain of Example 1

The TEA salt of the activated side chain of Example 1 (399 mg, 0.32 mmol, 2.81 eq of the analogue in question) was dissolved in NMP (2.6 mL). Total volume was estimated to be 3.1 mL which equals 0.96 eq/mL.

The solution was added to the solution of the GLP-1 analogue with a speed of 3.1 mL/h at room temperature. Samples were taken from the reaction during addition, namely at the following points (IPC) after addition of the following number of equivalents (eq) of the activated side chain (SC):

IPC1: 1.50 eq SC added;
IPC2: 2.52 eq SC added.

Due to the slow reactivity of the activated side chain (additionally 100 µL aliquot was taken, stirred separately for 130 min before it was analysed):

IPC3: 2.8 eq SC added.

pH was kept in the 11.27-11.33 interval during addition using 1M NaOH.

Activated Side Chain of Examples B, C, and D

The acylation of the GLP-1 analogue with the activated side chains of Examples B, C, and D was done with the same protocol but due to the fast hydrolysis more equivalents were used (see Table 3 below).

Results

The following parameters were determined for each of these experiments, and the results are shown in Table 3 below:

"Eq. SC" which refers to the number of equivalents used of the activated side chain relative to the peptide.

"Backbone %", "Mono-acylated %", "Di-acylated %", and "By-products %" which are indicative of the purity of the final product. The desired end product is here the di-acylated compound, the backbone refers to the non-acylated analogue, mono-acylated refers to the undesired mono-acylated product, and by-product refers to other by-products of the reaction. The reactions were analysed by HPLC_A_1, and the efficiency in the acylation process was estimated by area comparison in UV at 210 nm. For clarity in comparison, the combined area of "Backbone", "Mono-acylated", "Di-acylated", and "By-products" was normalized to 100%, and only the largest "By-product" was included. The retention times for the peaks of parameter of interest were as follows; "Backbone"—around 2.6 min, "Mono-acylated"—around 5.5 min, "Di-acylated"—around 8.3 min, and "By-products"-around 10.9 min.

TABLE 3

Surplus needed of activated side chain (SC) - and purity[a]

| SC Ex. no. | Eq. SC | Diacylated % | Mono-acylated % | Backbone % | By-products % |
|---|---|---|---|---|---|
| 1 | 2.5 | 97.5 | 0 | 0 | 2.5 |
| B | 3.2 | 88.0 | 5.5 | 0.3 | 6.2 |
| C | 3.4 | 49.3 | 44.6 | 6.0 | 0 |
| D | 3.3 | 97.3 | 2.7 | 0 | 1.0 |

[a]Analysis of the reactions were made after 130 min.

As regards purity, i.e. yield of the desired di-acylated end product, the results of Table 3 show that the activated side chain of the invention (Example 1) results in a product of better purity as compared to the state of the art activated side chain of Example B (NHS). Also the purity is much better as compared to the activated side chain of Example C. But the purity using the activated side chain of Example D is at the same high level as for the side chain of the invention (Example 1), however this is at the expense of having to use a surplus of equivalents of the activated side chain.

Turning to the surplus needed of the activated side chain the Table 3 results show that for the Example 1 side chain of the invention substantially less equivalents are needed as compared to all the other side chains.

In conclusion, these results indicate that the activated side chain of the invention gives a product of higher purity as the known process and with a cheaper acylation process.

Example 12: Preparation of acylated insulin analoque N{Epsilon-B29}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[GluA14,HisB25],des-ThrB27, ThrB30-Insulin Alternative name A14E, B25H, B29K(N$^\varepsilon$Icosanedioyl-γGlu-(3-(2-{2-[2-(2-aminoethoxy)ethoxy]ethoxy}ethoxy)propionyl), desB30 human insulin The purpose of this example is to study the use of the activated side chain of the invention to prepare an acylated insulin analogue. Focus is on the purity of the desired end product (the yield), and on the surplus that is needed of the activated side chain for the acylation reaction to proceed as desired. The activated side chain of the invention used in this example is that of Example 2, and it is tested along with the activated side chain of Example A, for comparison (the Example A side chain is known from, e.g., Example 4 of WO 2010/029159).

The insulin analogue used in this example is A14E, B25H, desB27, desB30 human insulin which is an analogue of human insulin wherein the amino acid at position 14 of the A chain has been replaced with glutamic acid, the amino acid at position 25 of the B chain has been replaced with histidine, and the B27 as well as the B30 amino acids have been deleted. The sequence and the preparation of this analogue is described in WO 2008/0343881 (SEQ ID NO: 8).

The side chain is to be attached to B29K of this analogue. B29K refers to the lysine residue at position 29 of the B chain. The side chain consists of a C18 diacid protractor and a gGlu-2×Ado linker. The resulting derivative is identical to the compound of Example 76 of WO 2009/1154699.

Acylation Procedure

Solid insulin analogue was weighed out (240 mg of compound of interest, 43.2 μmol) and transferred to the titrate vessel and mixed with 1.00 ml water for about 15 min. The peptide slowly dissolved. The pH was close to 9.

The auto-titrator vessel was connected to a cooling system and cooled at 5° C. and the pH was raised to 10.5 by adding NaOH (0.2 M, 400 μL) drop wise. The mixture was clear and colourless. 400 μL water was added manually to give a total volume of 1.80 mL. Just before addition of the activated side chain the insulin analogue solution was titrated to pH 11.7 with NaOH (0.5 M, 185 μL). The total volume and concentration of the peptide solution was 2.0 mL and 120 mg/mL.

Activated Side Chain of Example A

The activated side chain of Example A (52 mg of compound of interest, 1.5 eq.) was dissolved in 0.44 ml NMP to give a total volume of 0.50 ml.

Titrator: Titrando/Dosino®

Samples from the reaction were analysed by UPLC_A_3.

The acylation of the insulin analogue was controlled by the Titrando®. The apparatus was set op to add 1.5 eq. of sidechain in 19 min. Samples were withdrawn at 0 eq., 1 eq., and 1.5 eq. The samples were quenched in R-320: 50 mM Di-sodium hydrogen phosphate, di-hydrate with 0.1 mg/mL Tween® at pH 8 before the samples were analysed.

Activated Side Chain of Example 2

The same protocol as described above for "Activated side chain of Example A" was used for the activated side chain of Example 2.

Results

The following parameters were determined for each of these experiments, and the results are shown in Table 4 below:

"Eq. SC" which refers to the number of equivalents used of the activated side chain relative to the peptide.

"Backbone %", "Product %", and "Di-acylated %" which are indicative of the purity of the final product. The desired end product is the mono-acylated compound, the backbone refers to the non-acylated analogue, di-acylated refers to undesired by-products of the reaction. The reactions were analysed by UPLC_A_3, and the efficiency in the acylation process was estimated by area comparison in UV at 210 nm. For clarity in comparison, the combined area of "Backbone", "Product", and "Di-acylated" was normalized to 100%. The retention times for the peaks of parameter of interest were as follows; "Backbone"—around 9.4 min, "Product"—around 12.2 min, and "Di-acylated"—around 14.9 min.

TABLE 4

Surplus needed of activated side chain (SC) - and purity

| Activated side chain of Example no. | Eq. SC | Product % | Backbone % | Diacylated % |
|---|---|---|---|---|
| 2 | 1.0 | 66.0 | 18.0 | 16.0 |
| A | 1.0 | 58.0 | 36.0 | 5.0 |
| A | 1.5 | 67.0 | 16.0 | 17.0 |

As regards purity, i.e. yield of the desired product, the results of Table 4 show that the activated side chain of the invention (Example 2) results in a product of much higher purity as compared to the state of the art activated side chain of Example A (NHS) when the same number of equivalents is used (1 equivalent). However, when 1.5 equivalents of the Example A activated side chain is used the same purity is obtained as with 1 equivalent of the activated side chain of the invention (Example 2).

In conclusion, these results indicate that the activated side chain of the invention gives a product of as high purity as with the known process but one has to use less surplus of the activated side chain, thus with a cheaper acylation process.

Example 13: Hydrolytic Stability of Additional Activated Side Chains

The purpose of this example is to test the hydrolytic stability of additional activated side chains of the invention. More in particular, the hydrolytic stability of the activated side chains of Example 1 and three additional side chains of Examples 8B, 8C, and 8D as well as the additional activator 3,5-DC-2-HDMBSA.

Hydrolytic Stability

The hydrolytic stability of the activated side chains of Examples 1 and 8B to 8D was tested. The hydrolysis protocol from Example 9 was used for the stability test. The results are shown in Table 5.

TABLE 5

Hydrolysis of different activated side chains (changing activator and side chain)

| Example no. | Activator | Hydrolysis time (min) | Hydrolysis (%) at pH 10.3 | Method |
|---|---|---|---|---|
| 1 | 3,5-DC-2-HBSA | 1269 | 88.1 | UPLC_A_1 |
| 8B | 3,5-DC-2-HBSA | 1380 | 96 | UPLC_A_4 |
| 8C | 3,5-DC-2-HDMBSA | 1380 | 60 | UPLC_A_4 |
| 8D | 3,5-DC-2-HBSA | 1440 | 67 | UPLC_A_5 |

Acylation Reactions

The purpose of these acylation reactions was to study the structural scope of the invention by reacting different activated side chains of the invention with the GLP-1 analogue from Example 10. The GLP-1 analogue undergoing acylation in the present Example is (R34)GLP-1(9-37) (SEQ ID NO: 7), which may be prepared, e.g., as described in Example 2 of WO 2009/083549. The side chain was attached to the lysine at position 26. The activated side chains of the invention used in this Example were that of Example 8B, 8C, and 8D, and were tested along with the activated side chains of Example 1, for comparison.

The acylation procedure was as for Example 10, except the side chain (1.15 eq in NMP, 200 mg/mL) was added manually over 2 minutes to the alkaline aqueous solution of the GLP-1(9-37) analogue (200 mg, 20 mg/mL, pH 11.3). The pH of the solution was kept constant at pH 11.3 during the time of the reaction using a Tritrino/Dosino autotitrator. Samples from the reaction were quenched at different time with AcOH/MeCN/H$_2$O (2/1/1) and analysed using method UPLC-MS_A_6. Table 6 lists results of conversion after reaction times between 5 min and 2 hours.

TABLE 6

Acylation reaction of additional activated side chains

| Time of reaction (min) | Example 1 (Product %) | Example 8B (Product %) | Example 8C (Product %) | Example 8D (Product %) |
|---|---|---|---|---|
| 5 | 94 | — | 98.4 | 14 |
| 15 | 98 | 94 | Quantitative | 30 |
| 30 | Quantitative | 97 | Quantitative | 43 |
| 60 | Quantitative | Quantitative | Quantitative | 59 |
| 120 | Quantitative | Quantitative | Quantitative | 73 |

The results in Table 5 and 6 show that both the hydrolysis and the acylation reactions were surprisingly good for the activated side chains of the invention. Specifically, the tested activated side chains showed a very good hydrolytic stability and a product of high purity was obtained following acylation reaction.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A compound which comprises Chem. 7b:

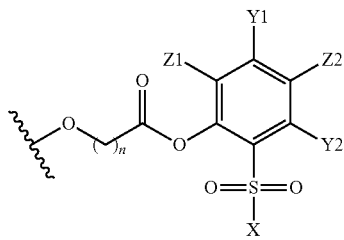

Chem. 7b wherein
n is an integer in the range of 1-2,
—Z1 and —Z2 independently are selected from the group consisting of —Cl, —F, —Br, —NO$_2$, —CN, —SO$_2$X2, —CONH, and —CF$_3$, wherein X2 is selected from the group consisting of —OH, CH$_3$, —CF$_3$, and —N(R$^1$R$^2$),
—Y1 and —Y2 independently are absent or selected from the group consisting of —Cl and —F,
—X is selected from the group consisting of —OH, CH$_3$, —CF$_3$, and —N(R$^1$R$^2$),
wherein R$^1$ and R$^2$ independently are selected from the group consisting of H and C1-C5 alkyl, wherein C1-C5 alkyl may be linear, branched or cyclic and optionally substituted with a hydrophilic moiety;
or a salt thereof.

2. The compound according to claim 1, wherein said compound comprises Chem. 7a:

Chem. 7a

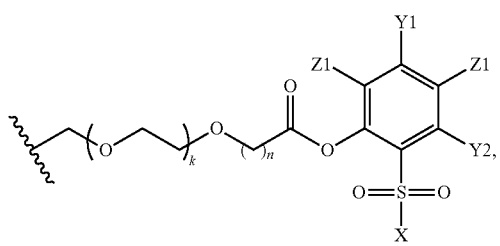

wherein k is an integer in the range of 1-10, and the remaining substituents are as defined in claim 1.

3. A compound according to claim 1, wherein said compound comprises Chem. 7:

Chem. 7

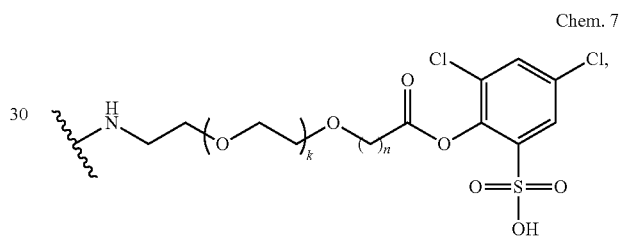

wherein k is an integer in the range of 1-10, and n is an integer in the range of 1-2; or a salt thereof.

4. The compound of claim 3, which comprises Formula I:

(P-L)$_U$-BL-B-A,    Formula I:

wherein
A is an activator of Chem. 1:

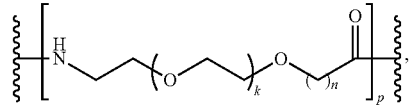

B is a linker element of Chem. 6:

wherein k is an integer in the range of 1-10, n is an integer in the range of 1-2, and p is an integer in the range of 1-5 with the proviso that if k>1 then p is 1;
U represents the number of groups (P-L) in the compound and is 1 or 2;

each group (P-L) comprises a protracting moiety (P) independently selected from Chem. 10, Chem. 11, Chem. 12, Chem. 13, and Chem. 14:

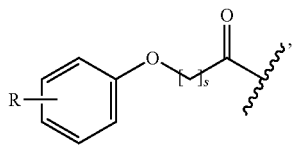

Chem. 10

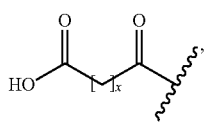

Chem. 11

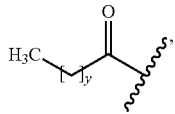

Chem. 12

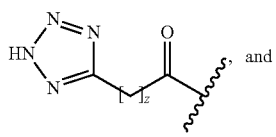

Chem. 13

, and

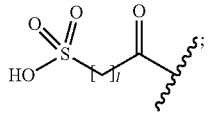

Chem. 14 and a linker (L) comprising at least one linker element selected from Chem. 15, Chem. 16, Chem. 17, and Chem. 18:

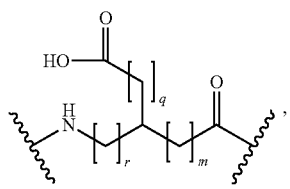

Chem. 15

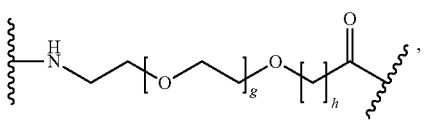

Chem. 16

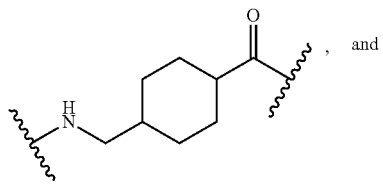

Chem. 17

, and

-continued

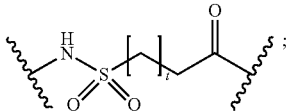

Chem. 18 wherein

R is —COOH; each of s, x, y, z, and l independently represents an integer in the range of 8-20; each of r, m, and q independently represents an integer in the range of 0-4; g is an integer in the range of 1-10; h is an integer in the range of 1-2, and t is an integer in the range of 1-5;

BL is an optional branched linker selected from Chem. 19 and Chem. 20:

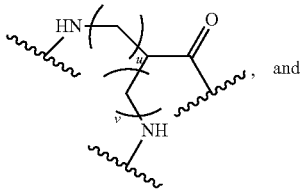

Chem. 19

, and

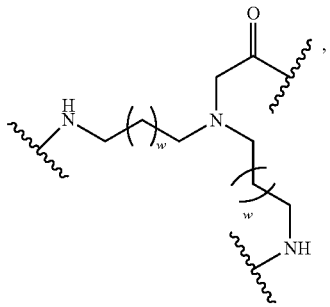

Chem. 20 wherein u and v independently represents an integer in the range of 0-5, with the provisos that when u is 0 v is an integer in the range of 1-5, and when v is 0 u is an integer in the range of 1-5; and each w independently represents an integer in the range of 0-2; and wherein the bond between A and B is an ester bond, the bond between P and L is an amide bond, and if BL is present the bonds between L and BL, and BL and B are amide bonds, or if BL is absent the bond between L and B is an amide bond;

or a salt, amide, or ester thereof.

5. The compound of claim 4, wherein k is 1, n is 1, and/or p is 1, 2, or 4.

6. The compound of claim 4, wherein P is Chem. 10 or Chem. 11.

7. The compound of claim 4, wherein L comprises linker element Chem. 15, linker element Chem. 16, and/or linker element Chem. 17.

8. The compound of claim 4, wherein i) if U is 1 BL is absent, and the compound comprises Formula Ia:

P-L-B-A;   Formula Ia:

or ii) if U is 2 BL is present, and the compound comprises Formula Ib:

(P-L)$_2$-BL-B-A.   Formula Ib:

9. The compound of claim 4, wherein
i) BL is Chem. 19, wherein u is 0 and v is 4; or
ii) BL is Chem. 20, wherein each w is 1.
10. A compound selected from the following:
Chem. 21
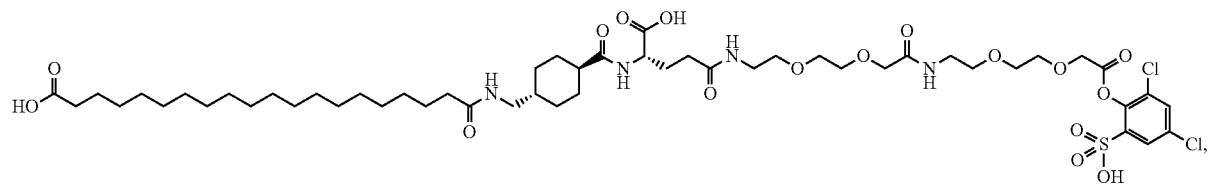
Chem. 22
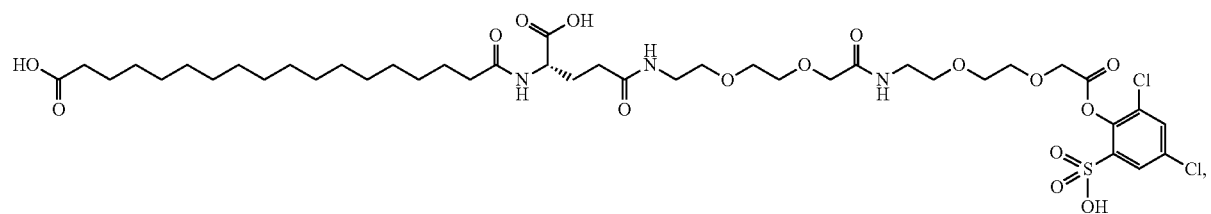
Chem. 23
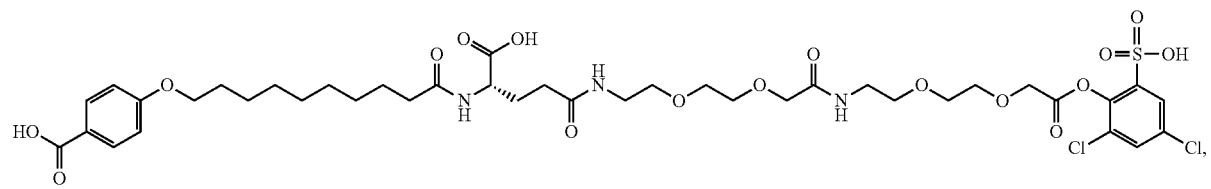
Chem. 24
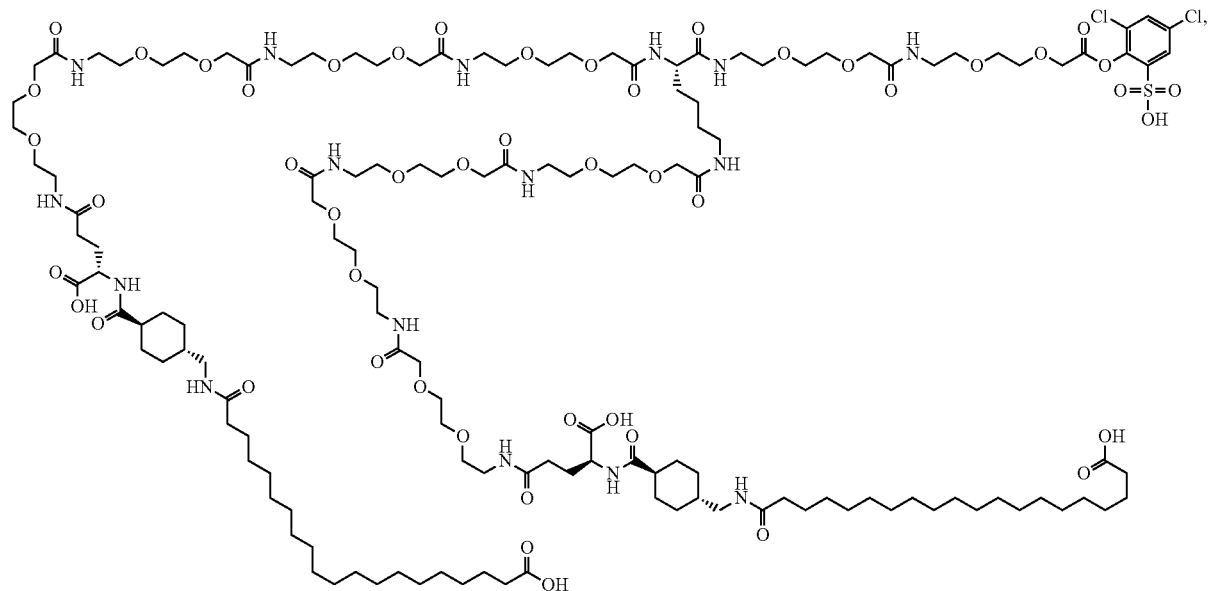

Chem. 25
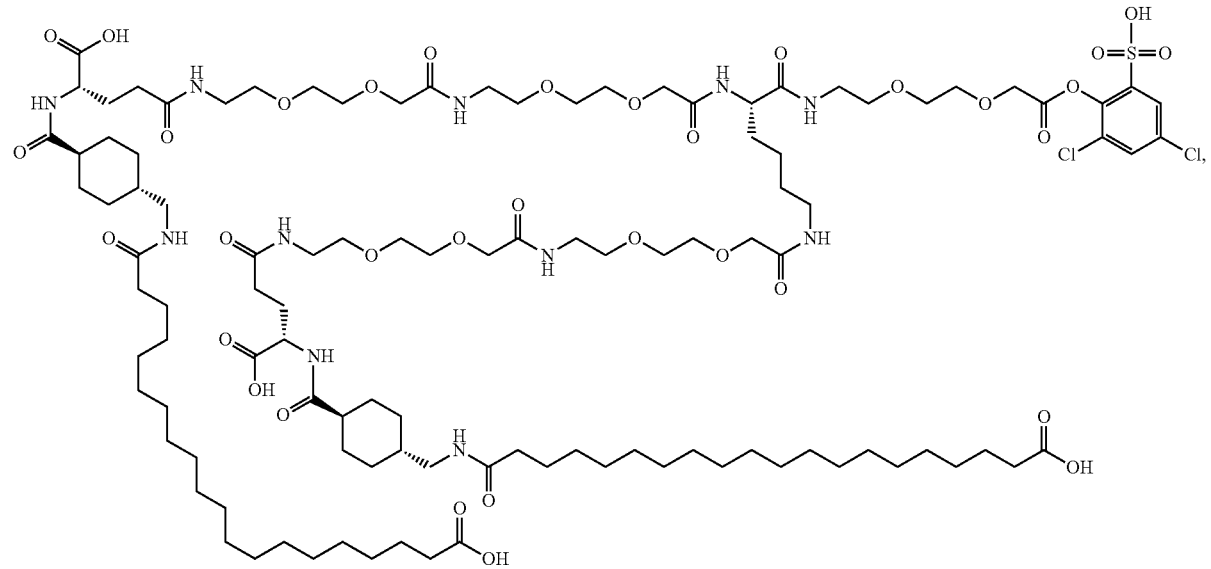
Chem. 26
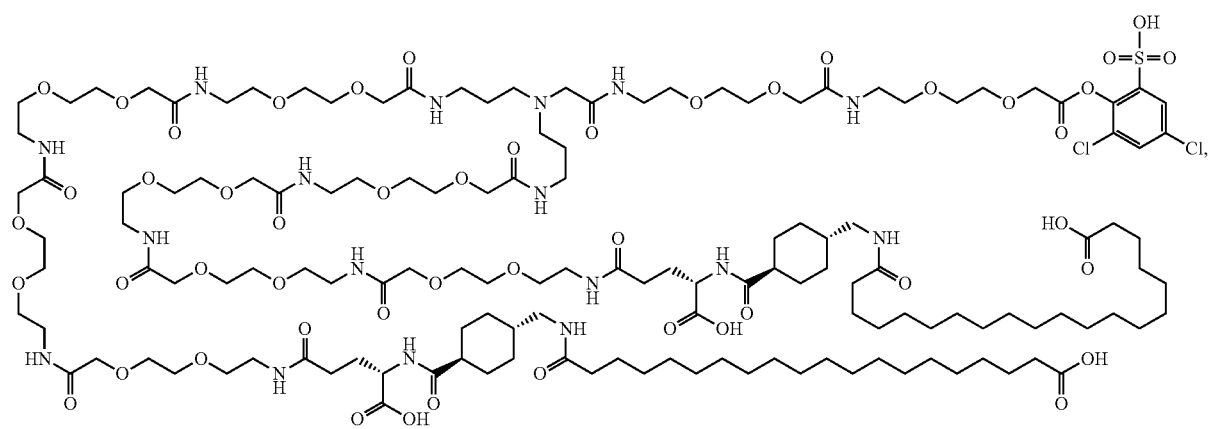
Chem. 27, and
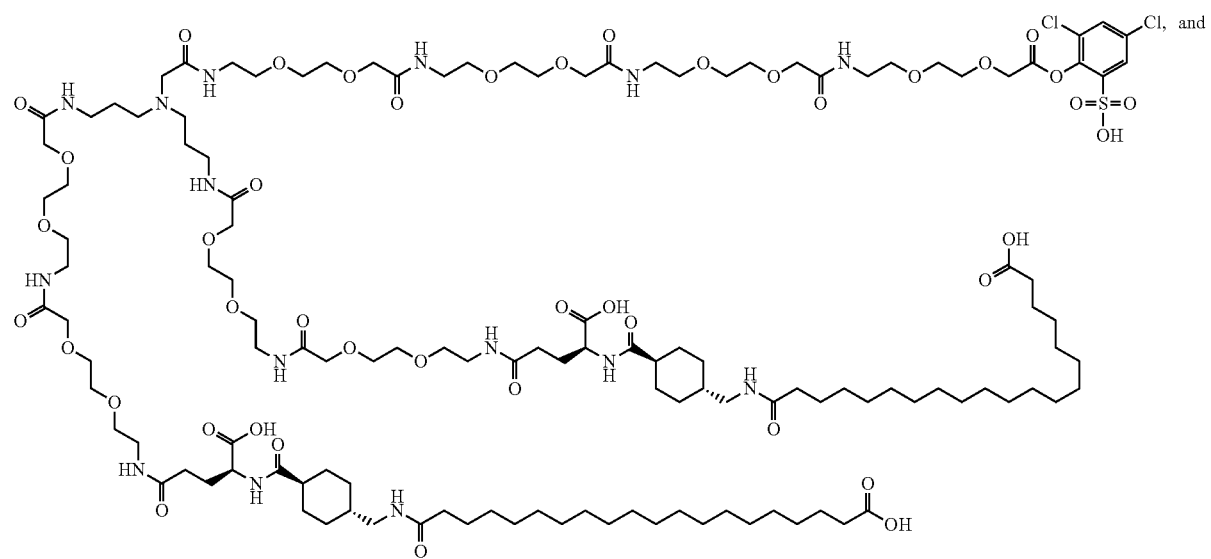

Chem. 28

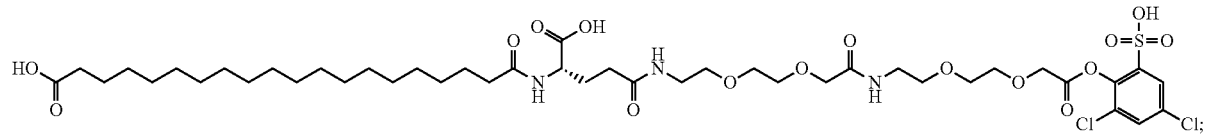

or a pharmaceutically acceptable salt, amide, or ester thereof.

11. A method for acylating one or more amino groups in an amino acid, a peptide, or a protein, the method comprising a step of reacting the amino acid, peptide, or protein with a compound as defined in claim 1.

12. The method of claim 11, which comprises a further step of purifying the desired product of the acylation reaction.

13. The method of claim 11, wherein the desired product of the acylation reaction is selected from the following compounds:

Chem. 41
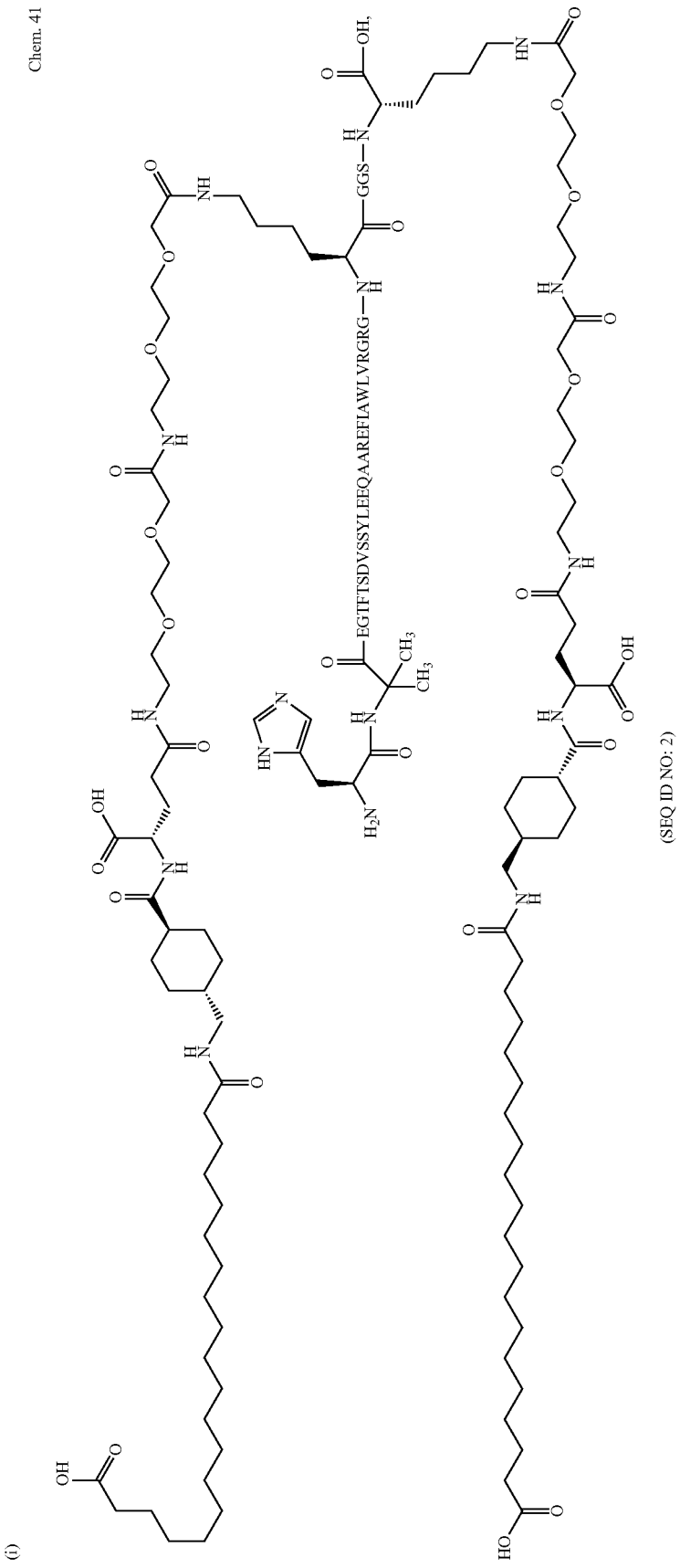
(SEQ ID NO: 2)

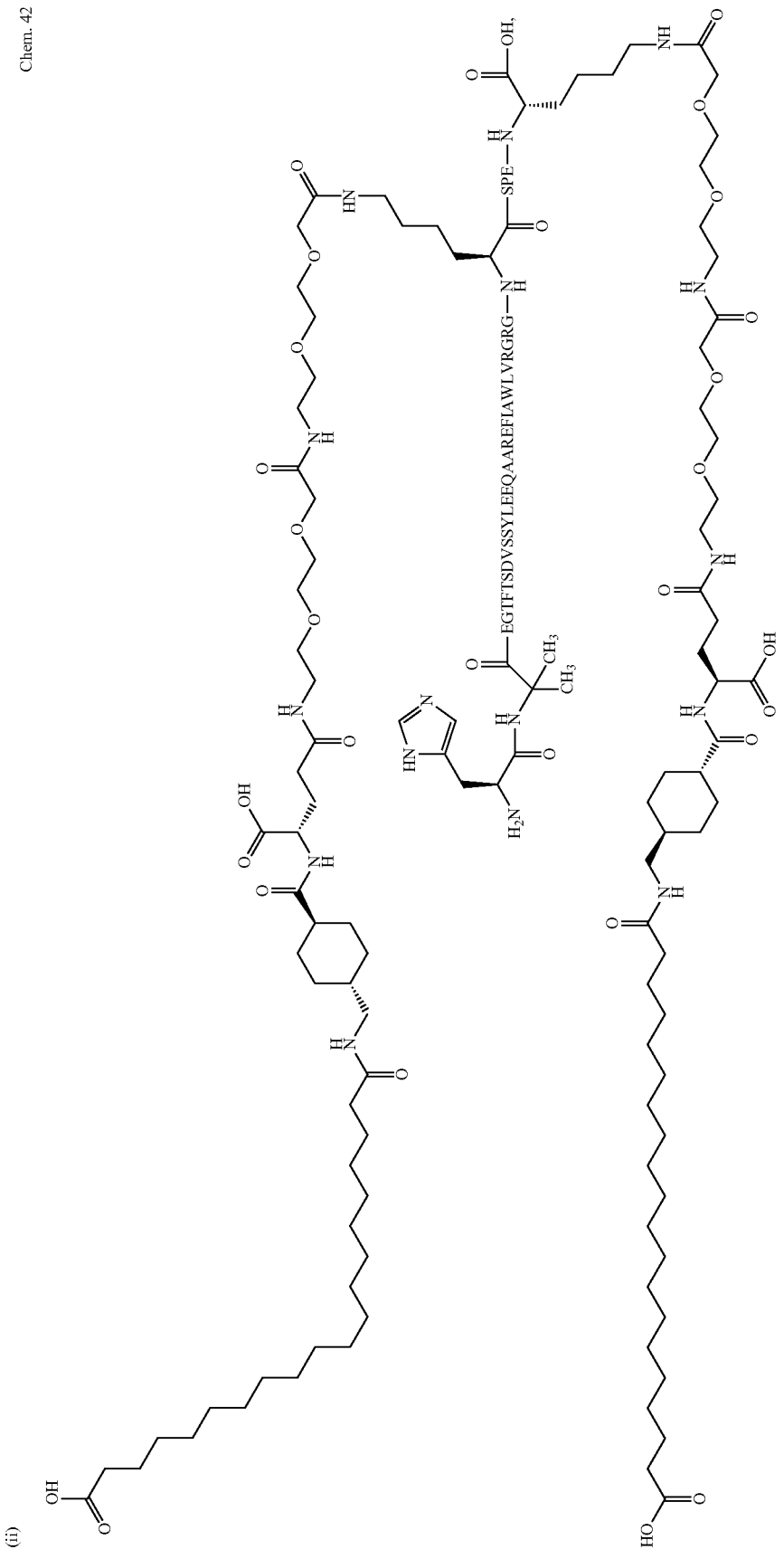
Chem. 42
(SEQ ID NO: 4)

(iii)
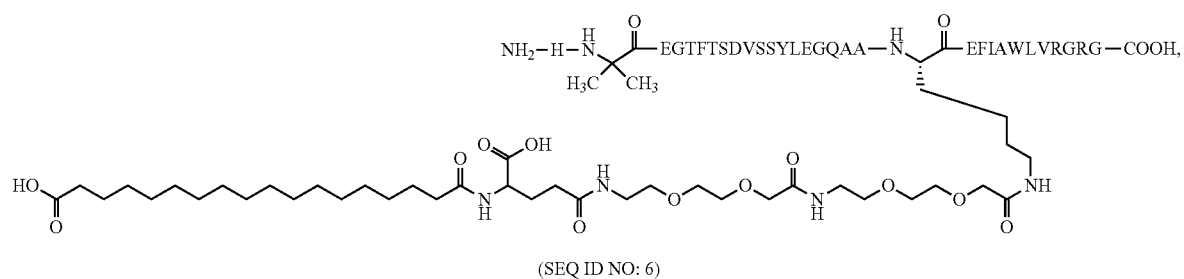
Chem. 43
(SEQ ID NO: 6)
(iv)
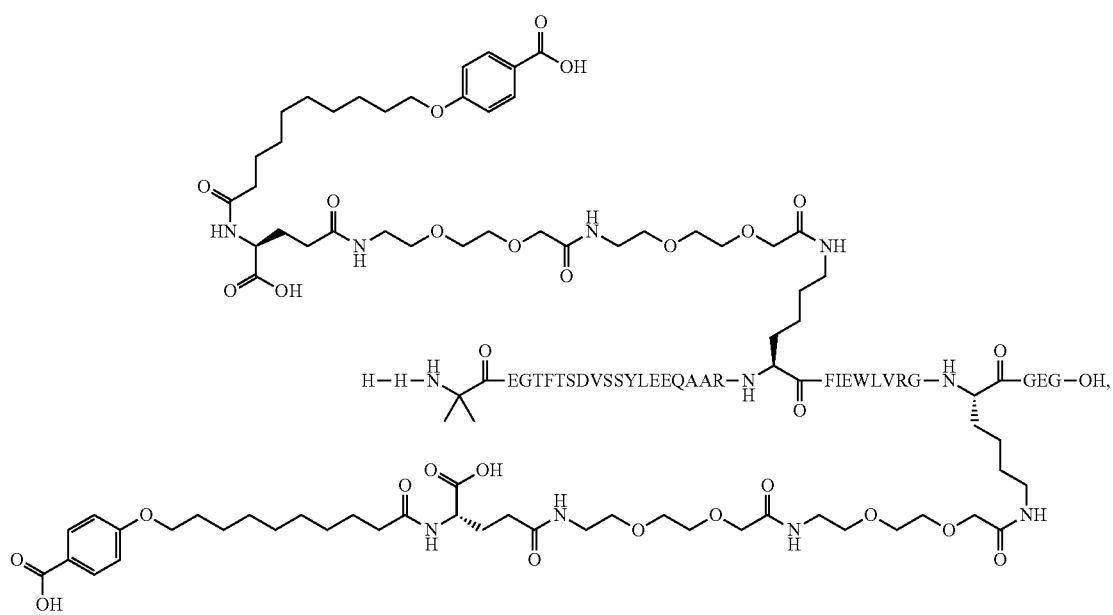
Chem. 44
(SEQ ID NO: 12)

(v) Chem. 45
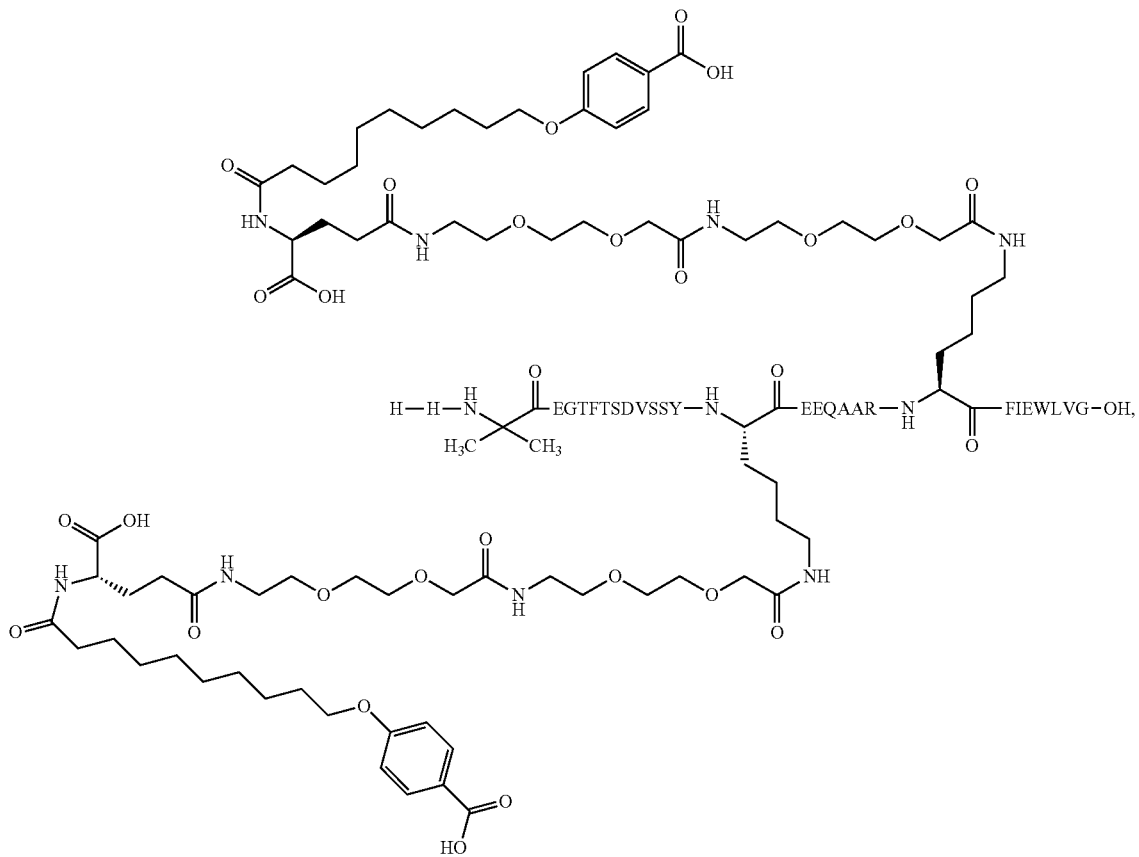
(SEQ ID NO: 14)

Chem. 46
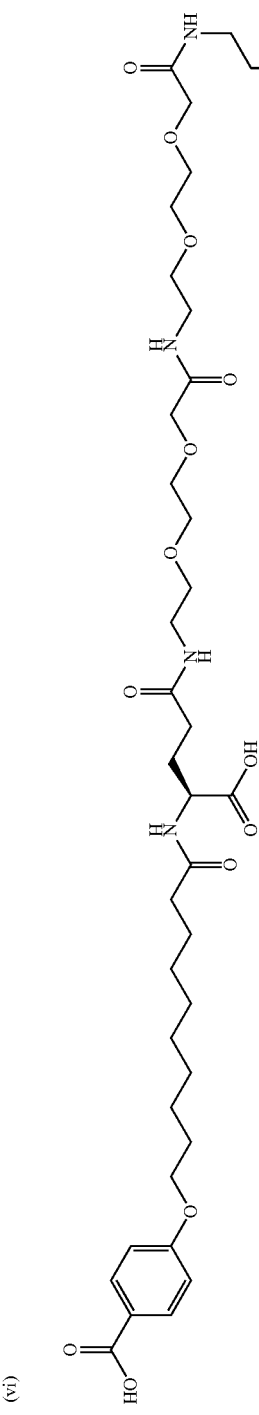
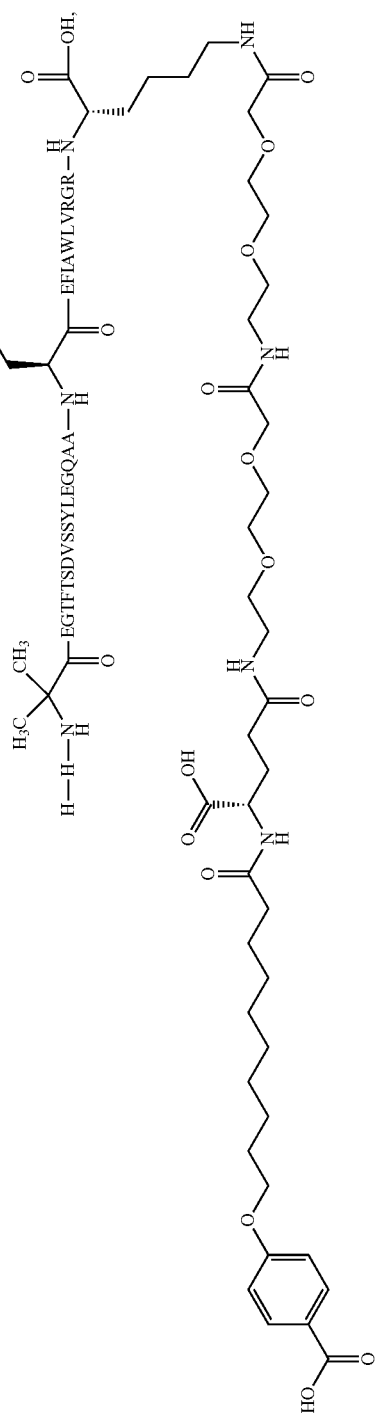
(vi) (SEQ ID NO: 16)

(vii) Chem. 47
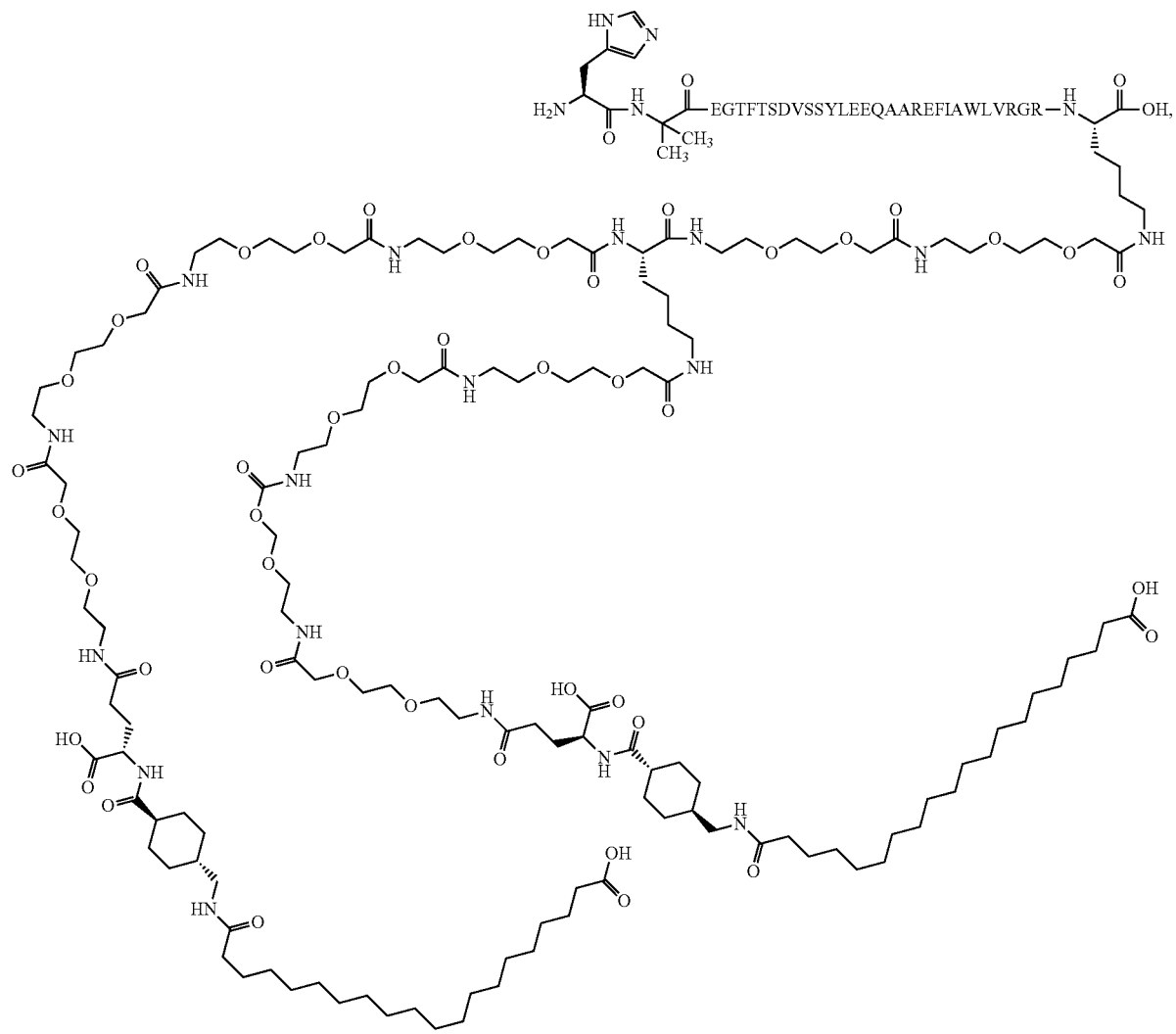
(SEQ ID NO: 18)

(viii)
Chem. 48
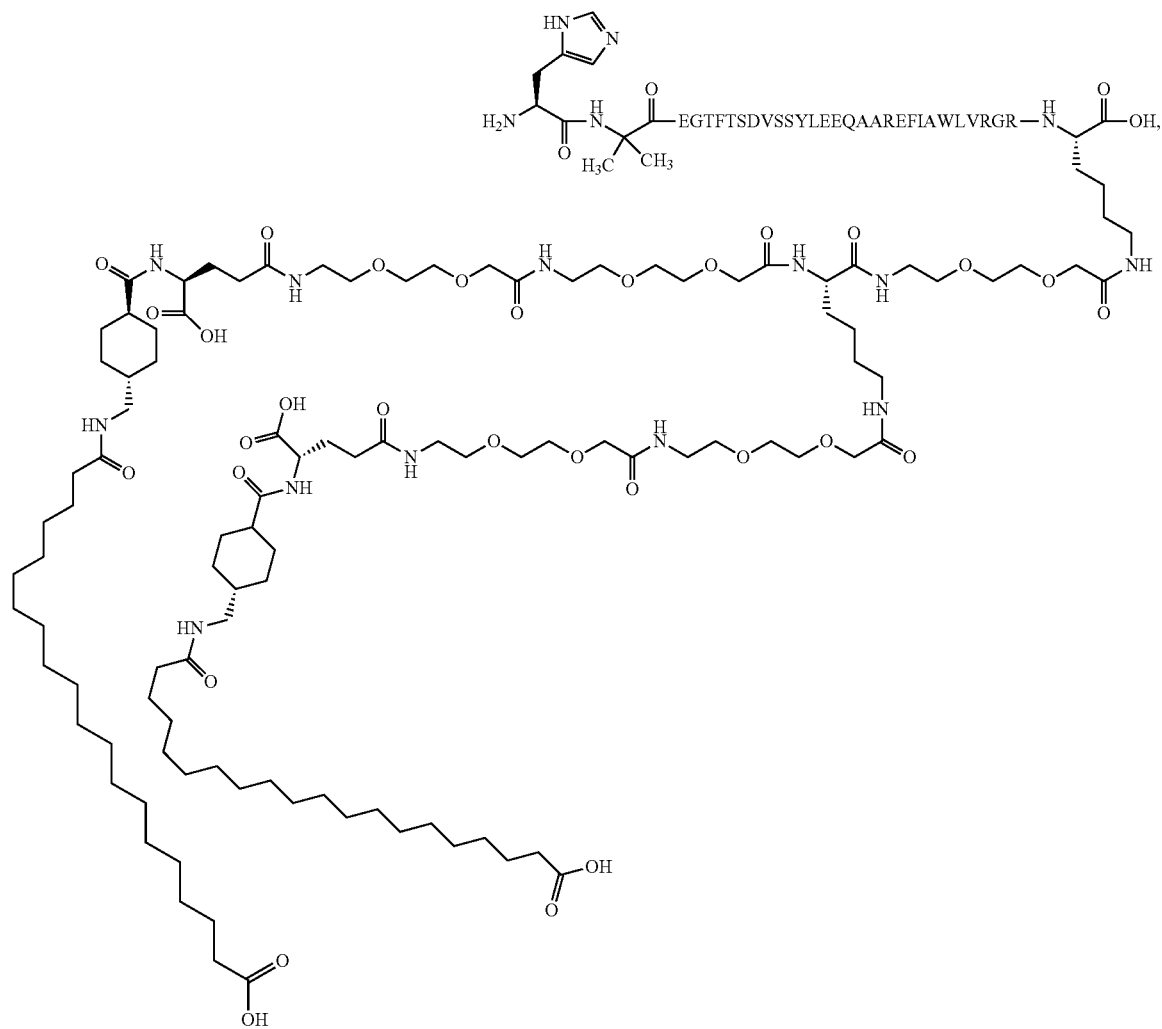
(SEQ ID NO: 18)

Chem. 49
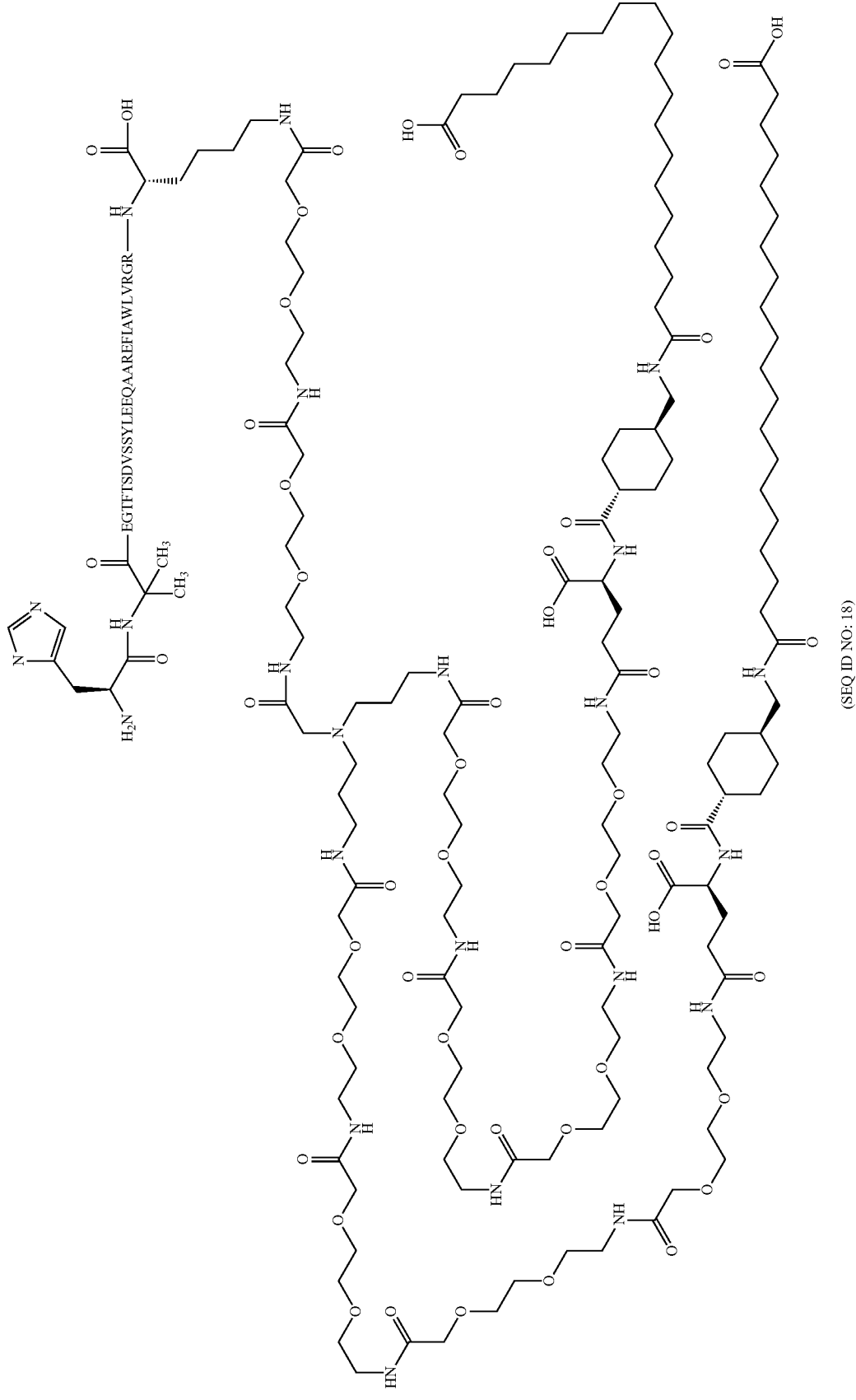
(ix) (SEQ ID NO: 18)

Chem. 50
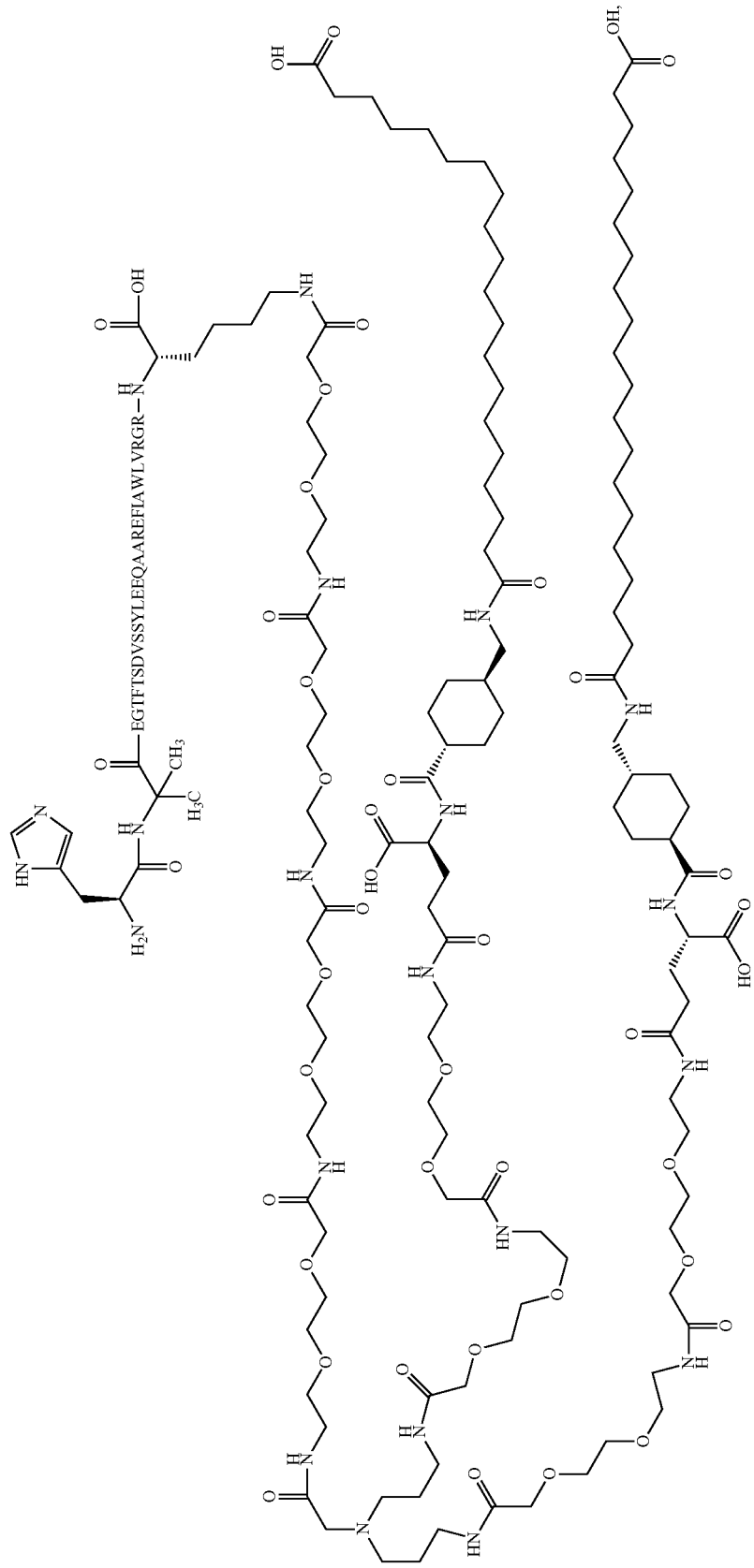
(SEQ ID NO: 18)

(xi): a compound as under (i) above in which the two N-terminal amino acids have been deleted,
(xii): a compound as under (ii) above in which the two N-terminal amino acids have been deleted,
(xiii): a compound as under (iii) above in which the two N-terminal amino acids have been deleted,
(xiv): a compound as under (iv) above in which the two N-terminal amino acids have been deleted,
(xv): a compound as under (v) above in which the two N-terminal amino acids have been deleted,
(xvi): a compound as under (vi) above in which the two N-terminal amino acids have been deleted,
(xvii): a compound as under (vii) above in which the two N-terminal amino acids have been deleted,
(xviii): a compound as under (iix) above in which the two N-terminal amino acids have been deleted,
(xix): a compound as under (ix) above in which the two N-terminal amino acids have been deleted,
(xx): a compound as under (x) above in which the two N-terminal amino acids have been deleted, and (xxiii)

(I) reacting the product of the acylation reaction with a protected di-peptide of Chem. 8:

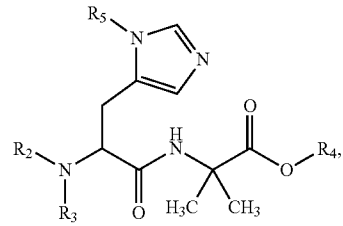

wherein
$R_2$ is H or an amino protecting group, and $R_3$ is an amino protecting group; or
$R_2$ is a removable alkyl group, and $R_3$ is H or a removable alkyl group; or
$R_2$ and $R_3$ are jointly forming a ring;

Chem. 53

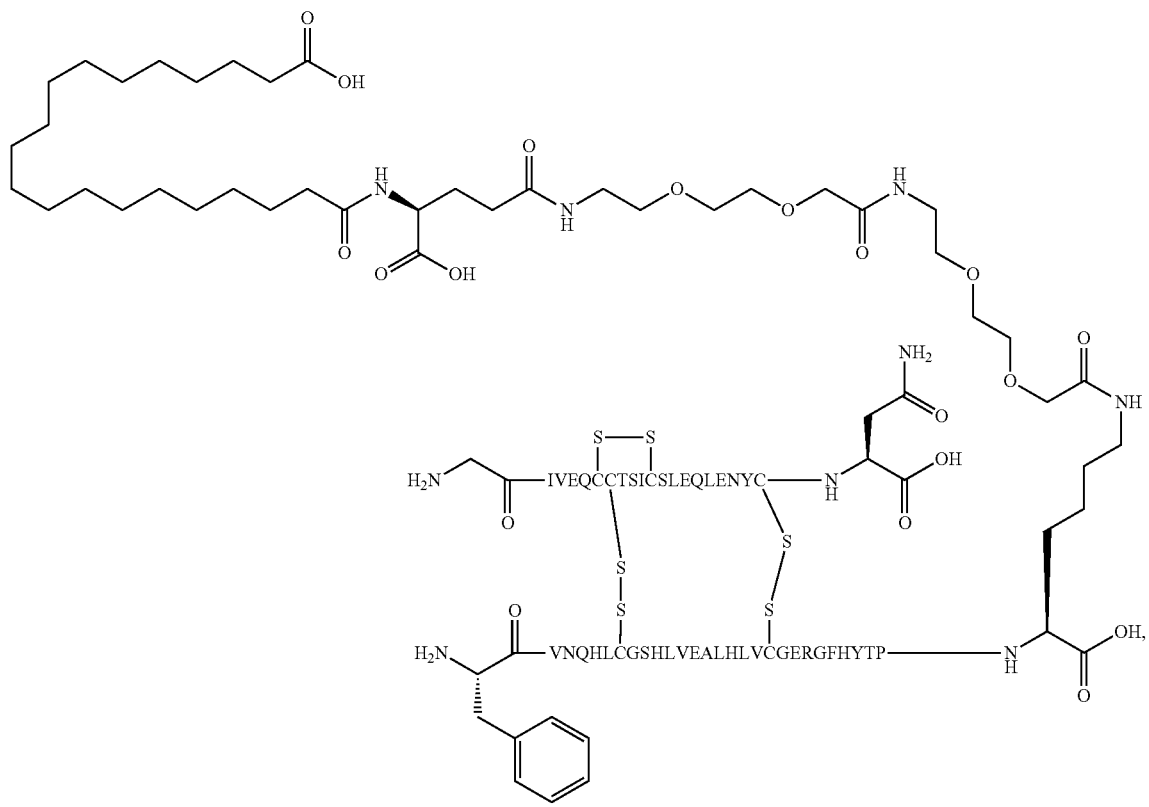

(SEQ ID NO: 8 and SEQ ID NO: 21)

or a pharmaceutically acceptable salt, amide, or ester thereof.

14. The method of claim 13, wherein when the desired product of the B acylation reaction an N-terminally truncated GLP-1 peptide having the sequence selected from (xi), (xii), (xiii), (xiv), (xv), (xvi), (xvii), (xviii), (xix), and (xx), then the method further comprises step (I) of:

$R_4$ is H, or a secondary ammonium cation, a tertiary ammonium cation or a metal cation forming a salt with the carboxylate group; and
$R_5$ is absent or an acidic salt, resulting in the corresponding acylated full-length GLP-1 peptide with protection groups at the N-terminus of the peptide;
and the method further comprises one or more of the following further steps (II) and (III) of:

(II) removing the protecting groups $R_2$ and/or $R_3$; and/or
(III) purifying the acylated full-length GLP-1 peptide;
wherein each of steps (II) and (III) are optional.

15. A compound selected from the compounds of SEQ ID NO: 3, SEQ ID NO: 5, SEQ ID NO: 13, SEQ ID NO: 15, SEQ ID NO: 19, or a pharmaceutically acceptable salt, amide, or ester thereof.

16. The compound according to claim 1, wherein the group —N($R^1R^2$) is N($CH_3$)$_2$, and the hydrophilic moiety is selected from —OH or —COOH.

* * * * *

SEQUENCE LISTING

```
<160> NUMBER OF SEQ ID NOS: 24

<210> SEQ ID NO 1
<211> LENGTH: 31
<212> TYPE: PRT
<213> ORGANISM: Homo sapiens
<220> FEATURE:
<221> NAME/KEY: PEPTIDE
<222> LOCATION: (1)..(31)
<223> OTHER INFORMATION: human GLP-1(7-37)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 36
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(36)
<223> OTHER INFORMATION: GLP-1 analogue
<220> FEATURE:
<221> NAME/KEY: MOD_RES
<222> LOCATION: (2)..(2)
<223> OTHER INFORMATION: Aib
```

<400> SEQUENCE: 2

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Lys
            20                  25                  30

Gly Gly Ser Lys
        35

<210> SEQ ID NO 3
<211> LENGTH: 34
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(34)

<400> SEQUENCE: 3

Glu Gly Thr Phe Thr Ser Asp Val Ser Ser Tyr Leu Glu Glu Gln Ala
1               5                   10                  15

Ala Arg Glu Phe Ile Ala Trp Leu Val Arg Gly Arg Gly Lys Gly Gly
            20                  25                  30

Ser Lys

<210> SEQ ID NO 4
<211> LENGTH: 36
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(36)
<220> FEATURE:
<221> NAME/KEY: MOD_RES
<222> LOCATION: (2)..(2)
<223> OTHER INFORMATION: Aib

<400> SEQUENCE: 4

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Lys
            20                  25                  30

Ser Pro Glu Lys
        35

<210> SEQ ID NO 5
<211> LENGTH: 34
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(34)

<400> SEQUENCE: 5

Glu Gly Thr Phe Thr Ser Asp Val Ser Ser Tyr Leu Glu Glu Gln Ala
1               5                   10                  15

Ala Arg Glu Phe Ile Ala Trp Leu Val Arg Gly Arg Gly Lys Ser Pro
            20                  25                  30

Glu Lys

```
<210> SEQ ID NO 6
<211> LENGTH: 31
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(31)
<220> FEATURE:
<221> NAME/KEY: MOD_RES
<222> LOCATION: (2)..(2)
<223> OTHER INFORMATION: Aib

<400> SEQUENCE: 6

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 7
<211> LENGTH: 29
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(29)

<400> SEQUENCE: 7

Glu Gly Thr Phe Thr Ser Asp Val Ser Ser Tyr Leu Glu Gly Gln Ala
1               5                   10                  15

Ala Lys Glu Phe Ile Ala Trp Leu Val Arg Gly Arg Gly
            20                  25

<210> SEQ ID NO 8
<211> LENGTH: 21
<212> TYPE: PRT
<213> ORGANISM: Artificial
<220> FEATURE:
<223> OTHER INFORMATION: A-chain of insulin analogue
<220> FEATURE:
<221> NAME/KEY: PEPTIDE
<222> LOCATION: (1)..(21)
<223> OTHER INFORMATION: A-chain of A14E, B25H, desB27, desB30 human
      insulin

<400> SEQUENCE: 8

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 9
<211> LENGTH: 28
<212> TYPE: PRT
<213> ORGANISM: Artificial
<220> FEATURE:
<223> OTHER INFORMATION: B-chain of insulin analogue
<220> FEATURE:
<221> NAME/KEY: PEPTIDE
<222> LOCATION: (1)..(28)
<223> OTHER INFORMATION: B-chain of A14E, B25H, desB27, desB30 human
      insulin

<400> SEQUENCE: 9
```

```
Phe Val Asn Gln His Leu Cys Gly Ser His Leu Val Glu Ala Leu Tyr
 1               5                  10                  15

Leu Val Cys Gly Glu Arg Gly Phe Lys Tyr Pro Lys
            20                  25

<210> SEQ ID NO 10
<211> LENGTH: 21
<212> TYPE: PRT
<213> ORGANISM: Artificial
<220> FEATURE:
<223> OTHER INFORMATION: Insulin analogue A chain
<220> FEATURE:
<221> NAME/KEY: PEPTIDE
<222> LOCATION: (1)..(21)
<223> OTHER INFORMATION: A-chain of A14E, B25H, desB30 human insulin

<400> SEQUENCE: 10

Gly Ile Val Glu Gln Cys Cys Thr Ser Ile Cys Ser Leu Glu Gln Leu
 1               5                  10                  15

Glu Asn Tyr Cys Asn
            20

<210> SEQ ID NO 11
<211> LENGTH: 29
<212> TYPE: PRT
<213> ORGANISM: Artificial
<220> FEATURE:
<223> OTHER INFORMATION: Insulin analogue B chain
<220> FEATURE:
<221> NAME/KEY: PEPTIDE
<222> LOCATION: (1)..(29)
<223> OTHER INFORMATION: B-chain of A14E, B25H, B29K, desB30 human
      insulin

<400> SEQUENCE: 11

Phe Val Asn Gln His Leu Cys Gly Ser His Leu Val Glu Ala Leu Tyr
 1               5                  10                  15

Leu Val Cys Gly Glu Arg Gly Phe His Tyr Thr Pro Lys
            20                  25

<210> SEQ ID NO 12
<211> LENGTH: 33
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(33)
<220> FEATURE:
<221> NAME/KEY: MOD_RES
<222> LOCATION: (2)..(2)
<223> OTHER INFORMATION: Aib

<400> SEQUENCE: 12

His Xaa Glu Gly Thr Phe Thr Ser Asp Val Ser Ser Tyr Leu Glu Glu
 1               5                  10                  15

Gln Ala Ala Arg Lys Phe Ile Glu Trp Leu Val Arg Gly Lys Gly Glu
            20                  25                  30

Gly

<210> SEQ ID NO 13
<211> LENGTH: 31
<212> TYPE: PRT
<213> ORGANISM: Artificial
<220> FEATURE:
<223> OTHER INFORMATION: GLP-1 analogue
```

```
<220> FEATURE:
<221> NAME/KEY: MOD_RES
<222> LOCATION: (2)..(2)
<223> OTHER INFORMATION: Aib

<400> SEQUENCE: 13

Glu Gly Thr Phe Thr Ser Asp Val Ser Ser Tyr Leu Glu Glu Gln Ala
1               5                   10                  15

Ala Arg Lys Phe Ile Glu Trp Leu Val Arg Gly Arg Lys Glu Gly
            20                  25                  30

<210> SEQ ID NO 14
<211> LENGTH: 28
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(28)
<220> FEATURE:
<221> NAME/KEY: MOD_RES
<222> LOCATION: (2)..(2)
<223> OTHER INFORMATION: Aib

<400> SEQUENCE: 14

His Xaa Glu Gly Thr Phe Thr Ser Asp Val Ser Ser Tyr Lys Glu Glu
1               5                   10                  15

Gln Ala Ala Arg Lys Phe Ile Glu Trp Leu Val Gly
            20                  25

<210> SEQ ID NO 15
<211> LENGTH: 26
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(26)

<400> SEQUENCE: 15

Glu Gly Thr Phe Thr Ser Asp Val Ser Ser Tyr Lys Glu Glu Gln Ala
1               5                   10                  15

Ala Arg Lys Phe Ile Glu Trp Leu Val Gly
            20                  25

<210> SEQ ID NO 16
<211> LENGTH: 31
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(31)
<220> FEATURE:
<221> NAME/KEY: MOD_RES
<222> LOCATION: (2)..(2)
<223> OTHER INFORMATION: Aib

<400> SEQUENCE: 16

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Lys
            20                  25                  30
```

```
<210> SEQ ID NO 17
<211> LENGTH: 29
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(29)

<400> SEQUENCE: 17

Glu Gly Thr Phe Thr Ser Asp Val Ser Ser Tyr Leu Glu Gly Gln Ala
1               5                   10                  15

Ala Lys Glu Phe Ile Ala Trp Leu Val Arg Gly Arg Gly
            20                  25

<210> SEQ ID NO 18
<211> LENGTH: 31
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(31)
<220> FEATURE:
<221> NAME/KEY: MOD_RES
<222> LOCATION: (1)..(31)
<223> OTHER INFORMATION: Aib

<400> SEQUENCE: 18

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Lys
            20                  25                  30

<210> SEQ ID NO 19
<211> LENGTH: 29
<212> TYPE: PRT
<213> ORGANISM: Artificial
<220> FEATURE:
<223> OTHER INFORMATION: GLP-1 analogue
<220> FEATURE:
<221> NAME/KEY: PEPTIDE
<222> LOCATION: (1)..(29)

<400> SEQUENCE: 19

Glu Gly Thr Phe Thr Ser Asp Val Ser Ser Tyr Leu Glu Glu Gln Ala
1               5                   10                  15

Ala Arg Glu Phe Ile Ala Trp Leu Val Arg Gly Arg Lys
            20                  25

<210> SEQ ID NO 20
<211> LENGTH: 21
<212> TYPE: PRT
<213> ORGANISM: Artificial
<220> FEATURE:
<223> OTHER INFORMATION: A-chain of insulin analogue
<220> FEATURE:
<221> NAME/KEY: PEPTIDE
<222> LOCATION: (1)..(21)
<223> OTHER INFORMATION: A-chain of A14E, B16H, B25H, desB30 human
      insulin

<400> SEQUENCE: 20

Gly Ile Val Glu Gln Cys Cys Thr Ser Ile Cys Ser Leu Glu Gln Leu
1               5                   10                  15

Glu Asn Tyr Cys Asn
```

<210> SEQ ID NO 21
<211> LENGTH: 29
<212> TYPE: PRT
<213> ORGANISM: Artificial
<220> FEATURE:
<223> OTHER INFORMATION: B-chain of insulin analogue
<220> FEATURE:
<221> NAME/KEY: PEPTIDE
<222> LOCATION: (1)..(29)
<223> OTHER INFORMATION: B-chain of A14E, B16E, B25H, desB30 human
      insulin

<400> SEQUENCE: 21

Phe Val Asn Gln His Leu Cys Gly Ser His Leu Val Glu Ala Leu His
1               5                   10                  15

Leu Val Cys Gly Glu Arg Gly Phe His Tyr Thr Pro Lys
            20                  25

<210> SEQ ID NO 22
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = L-histidine, (S)-2-Hydroxy-3-(1H-
      imidazol-4-yl)-propionic acid, D-histidine, deamino-histidine,
      homohistidine, N-alpha-acetyl-histidine, N-alpha-formyl-histidine,
      N-alpha-methyl-histidine, 3-pyridylalanine, 2-pyridylalanine, or
      4-pyridylalanine
<220> FEATURE:
<221> NAME/KEY: MISC_FEATURE
<222> LOCATION: (2)..(2)
<223> OTHER INFORMATION: Xaa = Ala, Gly, Ser, Aib, (1-aminocyclopropyl)
      carboxylic acid, or (1-aminocyclobutyl) carboxylic acid
<220> FEATURE:
<221> NAME/KEY: MISC_FEATURE
<222> LOCATION: (6)..(6)
<223> OTHER INFORMATION: Xaa = Phe or Leu
<220> FEATURE:
<221> NAME/KEY: MISC_FEATURE
<222> LOCATION: (10)..(10)
<223> OTHER INFORMATION: Xaa = Val or Leu
<220> FEATURE:
<221> NAME/KEY: MISC_FEATURE
<222> LOCATION: (12)..(12)
<223> OTHER INFORMATION: Xaa = Ser, Val, Arg, or Leu
<220> FEATURE:
<221> NAME/KEY: MISC_FEATURE
<222> LOCATION: (13)..(13)
<223> OTHER INFORMATION: Xaa = Tyr or Gln
<220> FEATURE:
<221> NAME/KEY: MISC_FEATURE
<222> LOCATION: (14)..(14)
<223> OTHER INFORMATION: Xaa = Leu, Lys, or Met
<220> FEATURE:
<221> NAME/KEY: MISC_FEATURE
<222> LOCATION: (16)..(16)
<223> OTHER INFORMATION: Xaa = Gly or Glu
<220> FEATURE:
<221> NAME/KEY: MISC_FEATURE
<222> LOCATION: (17)..(17)
<223> OTHER INFORMATION: Xaa = Gln, Glu, or Arg
<220> FEATURE:
<221> NAME/KEY: MISC_FEATURE
<222> LOCATION: (19)..(19)
<223> OTHER INFORMATION: Xaa = Ala or Val
<220> FEATURE:
<221> NAME/KEY: MISC_FEATURE
<222> LOCATION: (20)..(20)
<223> OTHER INFORMATION: Xaa = Lys or Arg

```
<220> FEATURE:
<221> NAME/KEY: MISC_FEATURE
<222> LOCATION: (21)..(21)
<223> OTHER INFORMATION: Xaa = Glu, Lys, or Leu
<220> FEATURE:
<221> NAME/KEY: MISC_FEATURE
<222> LOCATION: (24)..(24)
<223> OTHER INFORMATION: Xaa = Ala, Glu, or Arg
<220> FEATURE:
<221> NAME/KEY: MISC_FEATURE
<222> LOCATION: (25)..(25)
<223> OTHER INFORMATION: Xaa = Trp or His
<220> FEATURE:
<221> NAME/KEY: MISC_FEATURE
<222> LOCATION: (27)..(27)
<223> OTHER INFORMATION: Xaa = Val
<220> FEATURE:
<221> NAME/KEY: MISC_FEATURE
<222> LOCATION: (28)..(28)
<223> OTHER INFORMATION: Xaa = Arg, His, Asn, Gly, or Gln
<220> FEATURE:
<221> NAME/KEY: MISC_FEATURE
<222> LOCATION: (29)..(29)
<223> OTHER INFORMATION: Xaa = Gly, Ala, or absent
<220> FEATURE:
<221> NAME/KEY: MISC_FEATURE
<222> LOCATION: (30)..(30)
<223> OTHER INFORMATION: Xaa = Arg, Lys, Gly, or absent
<220> FEATURE:
<221> NAME/KEY: MISC_FEATURE
<222> LOCATION: (31)..(31)
<223> OTHER INFORMATION: Xaa = Gly, Pro, Lys, or absent
<220> FEATURE:
<221> NAME/KEY: MISC_FEATURE
<222> LOCATION: (32)..(32)
<223> OTHER INFORMATION: Xaa = Ser, Gly, Ala, Glu, Pro, Lys, or absent
<220> FEATURE:
<221> NAME/KEY: MISC_FEATURE
<222> LOCATION: (33)..(35)
<223> OTHER INFORMATION: Xaa = Ser, Gly, Ala, Glu, Pro, or absent
<220> FEATURE:
<221> NAME/KEY: MISC_FEATURE
<222> LOCATION: (36)..(36)
<223> OTHER INFORMATION: Xaa = Lys or absent

<400> SEQUENCE: 22

Xaa Xaa Glu Gly Thr Xaa Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Xaa Xaa Xaa
            20                  25                  30

Xaa Xaa Xaa Xaa
        35

<210> SEQ ID NO 23
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa = Phe or Leu
<220> FEATURE:
<221> NAME/KEY: MISC_FEATURE
<222> LOCATION: (8)..(8)
<223> OTHER INFORMATION: Xaa = Val or Leu
<220> FEATURE:
<221> NAME/KEY: MISC_FEATURE
<222> LOCATION: (10)..(10)
<223> OTHER INFORMATION: Xaa = Ser, Val, Arg, or Leu
<220> FEATURE:
<221> NAME/KEY: MISC_FEATURE
<222> LOCATION: (11)..(11)
<223> OTHER INFORMATION: Xaa = Tyr or Gln
```

```
<220> FEATURE:
<221> NAME/KEY: MISC_FEATURE
<222> LOCATION: (12)..(12)
<223> OTHER INFORMATION: Xaa = Leu, Lys, or Met
<220> FEATURE:
<221> NAME/KEY: MISC_FEATURE
<222> LOCATION: (14)..(14)
<223> OTHER INFORMATION: Xaa = Gly or Glu
<220> FEATURE:
<221> NAME/KEY: MISC_FEATURE
<222> LOCATION: (15)..(15)
<223> OTHER INFORMATION: Xaa = Gln, Glu, or Arg
<220> FEATURE:
<221> NAME/KEY: MISC_FEATURE
<222> LOCATION: (17)..(17)
<223> OTHER INFORMATION: Xaa = Ala or Val
<220> FEATURE:
<221> NAME/KEY: MISC_FEATURE
<222> LOCATION: (18)..(18)
<223> OTHER INFORMATION: Xaa = Lys or Arg
<220> FEATURE:
<221> NAME/KEY: MISC_FEATURE
<222> LOCATION: (19)..(19)
<223> OTHER INFORMATION: Xaa = Glu, Lys, or Leu
<220> FEATURE:
<221> NAME/KEY: MISC_FEATURE
<222> LOCATION: (22)..(22)
<223> OTHER INFORMATION: Xaa = Ala, Glu, or Arg
<220> FEATURE:
<221> NAME/KEY: MISC_FEATURE
<222> LOCATION: (23)..(23)
<223> OTHER INFORMATION: Xaa = Trp or His
<220> FEATURE:
<221> NAME/KEY: MISC_FEATURE
<222> LOCATION: (25)..(25)
<223> OTHER INFORMATION: Xaa = Val
<220> FEATURE:
<221> NAME/KEY: MISC_FEATURE
<222> LOCATION: (26)..(26)
<223> OTHER INFORMATION: Xaa = Arg, His, Asn, Gly, or Gln
<220> FEATURE:
<221> NAME/KEY: MISC_FEATURE
<222> LOCATION: (27)..(27)
<223> OTHER INFORMATION: Xaa = Gly, Ala, or absent
<220> FEATURE:
<221> NAME/KEY: MISC_FEATURE
<222> LOCATION: (28)..(28)
<223> OTHER INFORMATION: Xaa = Arg, Lys, Gly, or absent
<220> FEATURE:
<221> NAME/KEY: MISC_FEATURE
<222> LOCATION: (29)..(29)
<223> OTHER INFORMATION: Xaa = Gly, Pro, Lys, or absent
<220> FEATURE:
<221> NAME/KEY: MISC_FEATURE
<222> LOCATION: (30)..(30)
<223> OTHER INFORMATION: Xaa = Ser, Gly, Ala, Glu, Pro, Lys, or absent
<220> FEATURE:
<221> NAME/KEY: MISC_FEATURE
<222> LOCATION: (31)..(33)
<223> OTHER INFORMATION: Xaa = Ser, Gly, Ala, Glu, Pro, or absent
<220> FEATURE:
<221> NAME/KEY: MISC_FEATURE
<222> LOCATION: (34)..(34)
<223> OTHER INFORMATION: Xaa = Lys or absent

<400> SEQUENCE: 23

Glu Gly Thr Xaa Thr Ser Asp Xaa Ser Xaa Xaa Xaa Glu Xaa Xaa Ala
1               5                   10                  15

Xaa Xaa Xaa Phe Ile Xaa Xaa Leu Xaa Xaa Xaa Xaa Xaa Xaa Xaa
            20                  25                  30

Xaa Xaa

<210> SEQ ID NO 24
<211> LENGTH: 31
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = N-alpha-formyl-histidine
<220> FEATURE:
<221> NAME/KEY: MISC_FEATURE
<222> LOCATION: (20)..(20)
<223> OTHER INFORMATION: Modified Lysine

<400> SEQUENCE: 24

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```